(12) United States Patent
Rodriguez-Franco et al.

(10) Patent No.: US 7,834,167 B2
(45) Date of Patent: Nov. 16, 2010

(54) MOSS EXPRESSING PROMOTION REGIONS

(75) Inventors: Marta Rodriguez-Franco, Freiburg (DE); Wolfgang Jost, Freiburg (DE); Andreas Weise, Freiburg (DE); Gilbert Gorr, Freiburg (DE)

(73) Assignee: Greenovation Biotech GmbH, Freiburg (DE)

( * ) Notice: Subject to any disclaimer, the term of this patent is extended or adjusted under 35 U.S.C. 154(b) by 0 days.

(21) Appl. No.: 12/134,665

(22) Filed: Jun. 6, 2008

(65) Prior Publication Data

US 2009/0111187 A1    Apr. 30, 2009

Related U.S. Application Data

(63) Continuation of application No. 10/568,156, filed as application No. PCT/EP2004/008580 on Jul. 30, 2004, now Pat. No. 7,538,259.

(30) Foreign Application Priority Data

Aug. 11, 2003    (EP)    ................................. 03450184

(51) Int. Cl.
  C12N 15/82    (2006.01)
  C12N 15/00    (2006.01)
  C12N 15/11    (2006.01)
  C07H 21/04    (2006.01)
(52) U.S. Cl. .................. 536/24.1; 536/23.1; 435/320.1; 435/468; 800/278; 800/295
(58) Field of Classification Search ........................ None
  See application file for complete search history.

(56) References Cited

U.S. PATENT DOCUMENTS 4,710,461 A  *  12/1987  Komano et al. ............. 435/488

FOREIGN PATENT DOCUMENTS

| CA | 2381995 | 4/2001 |
|----|---------|--------|
| DE | 19947290 | 4/2001 |
| EP | 1206561 | 2/2003 |
| WO | WO 00/49153 | 8/2000 |
| WO | WO 01/64901 | 4/2001 |
| WO | WO 01/25456 | 9/2001 |

OTHER PUBLICATIONS

Henschel et al 2002 Mol. Biol. Evol. 19:801-814.*
Kim et al 1994, Plant Molecular Biology 24:105-117, provided in Applicants IDS.*
Donald et al 1990, EMBO J. 9:1717-1726, provided in Applicants IDS.*
Dolferus et al 1994, Plant Physiology 105:1075-1087.*
Henschel et al 2002 Mol. Biol. Evol. 19:801-814, provided in Applicants IDS.*
Berlin et al., "Genetic modification of plant secondary metabolism: Alteration of product levels by overexpression of amino acid decarboxylases," In: Advances in Plant Biology, Studies in Plant Science, Elsevier, Amsterdam (Ryu and Furasaki, eds.) 4:57-81, 1994.
Cove et al., "Mosses as model systems," *Trends Plant Sci.*, 2:99-105, 1997.
Database EMBL, "*Physcomitrella patens* subsp. *patens* cDNA clone:pphb18g10, 5' end, single read," Database accession No. BJ176671, 2002.
Database EMBL, "*Physcomitrella patens* subsp. *patens* cDNA clone:pph18g08, 5' end, single read," Database accession No. BJ160219, 2002.
Database EMBL, "*Physcomitrella patens* subsp. *patens* cDNA clone:pphb19d05, 5' end, single read," Database accession No. BJ176917, 2002.
Dolferus et al., "Differential interactions of promoter elements in stress responses of the *Arabidopsis* Adh gene," *Plant Physiology*, 105:1075-1087, 1994.
Donald et al., "Mutation of either G box or I box sequences profoundly affects expression from the *Arabidopsis* rbcS-1A promoter," *EMBO J.*, 9:1717-1726, 1990.
Henschel et al., "Two ancient classes of MIKC-type MADS-box genes are present in the moss *Physcomitrella patens*," *Mol. Biol. Evol.*, 19:801-814, 2002.
Hiwatashi et al., "Establishment of gene-trap and enhancer-trap systems in the moss *Physcomitrella patens*," *Plant J.*, 28:105-116, 2001.
Holtdorf et al., "Promoter subfragments of the sugar beet V-type H+-ATPase subunit isoform drive the expression of trangenes in the moss *Physcomitrella patens*," *Plant Cell Rep.*, 21:341-346, 2002.
Jost et al., "Isolation and characterization of three moss-derived beta-tubulin promoters suitable for recombinant expression," *Current Genetics*, 47:111-120, 2005.
Kasten et al., "The plastome-encoded zfp A gene of a moss contains procaryotics as well as eucaryotic promoter consensus sequences and its RNA abundance is modulated by cytokinin," 22:327-333, 1992.
Kim et al., "A 20 nucleotide upstream element is essential for the nopaline synthase (nos) promoter activity," *Plant Molecular Biology*, 24:105-117, 1994.
Kohara et al., "*P. patens* cDNA," Database EMBL, Database accession No. BJ190411, 2002.
Kohara et al., "*Physcomitrella patens* subsp. *patens* cDNA," Database EMBL, Database accession No. BJ176671, 2002.
Office Action issued in U.S. Appl. No. 10/568,156, mailed Apr. 23, 2007.
Office Action issued in U.S. Appl. No. 10/568,156, mailed Oct. 5, 2007.
Reski, "Development, Genetics and Molecular Biology of Mosses," *Botanica Acta*, 111:1-15, 1998.
Reski, "Molecular genetics of *Physcomitrella*," *Planta*, 208:301-309, 1999.
Schaefer, "A New Moss Genetics: Targeted Mutagenesis in *Physcomitrella patens*," *Annu. Rev. Plant Biol.*, 53:477-501, 2002.
Zeidler et al., "Transgene Expression in the Moss *Ceratodon purpureus*," *J. Plant Physiol.*, 154:641-650, 1999.

* cited by examiner

*Primary Examiner*—Anne Marie Grunberg
*Assistant Examiner*—Brent Page
(74) *Attorney, Agent, or Firm*—Fulbright & Jaworski LLP

(57) ABSTRACT

Disclosed are isolated nucleic acid molecules encoding wild type nucleus derived moss expression promoting regions (MEPRs) as well as a method for producing recombinant polypeptides using such MEPRs.

16 Claims, 19 Drawing Sheets

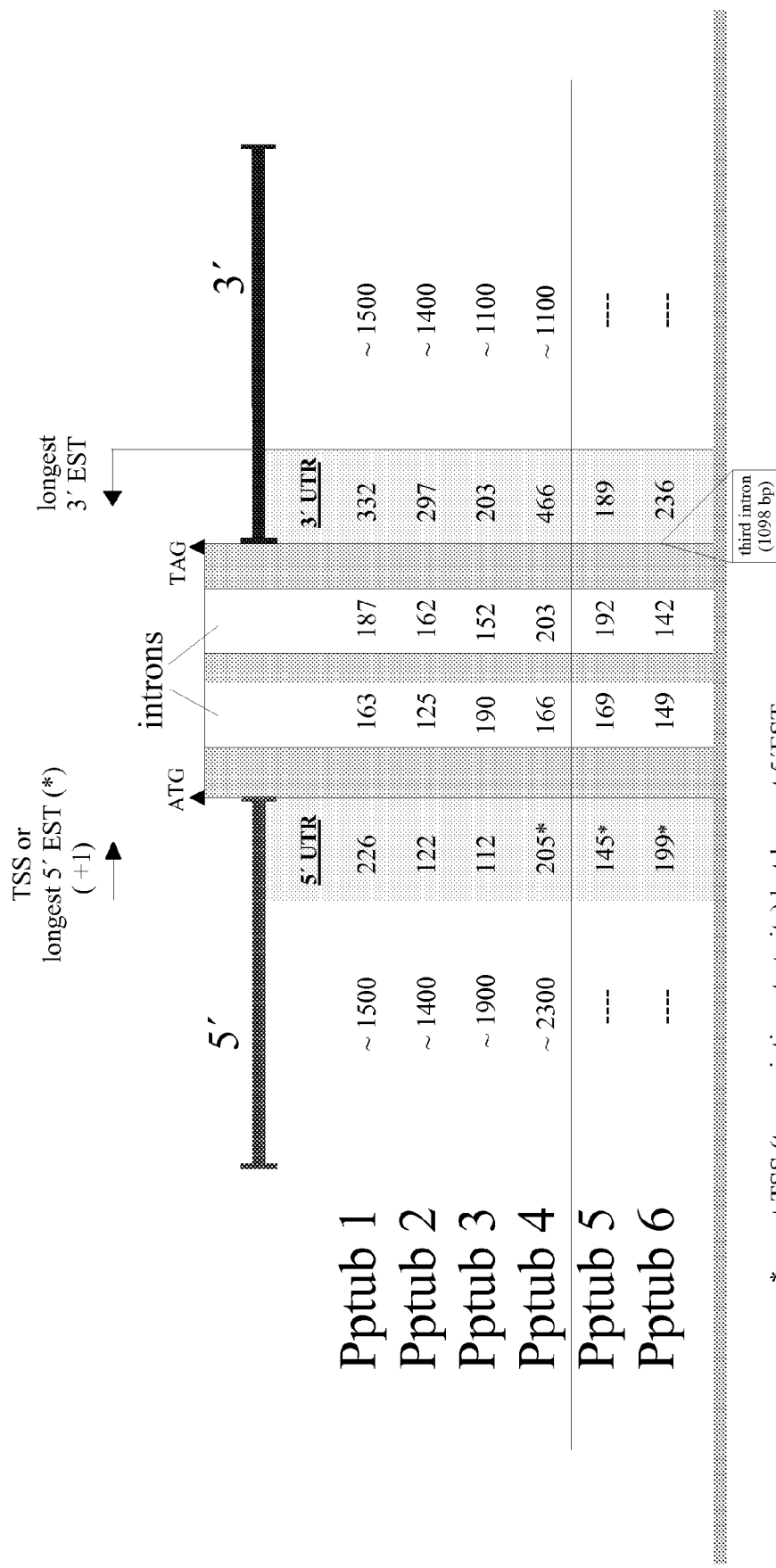
Fig. 1: ß-tubulin genes in Physcomitrella patens

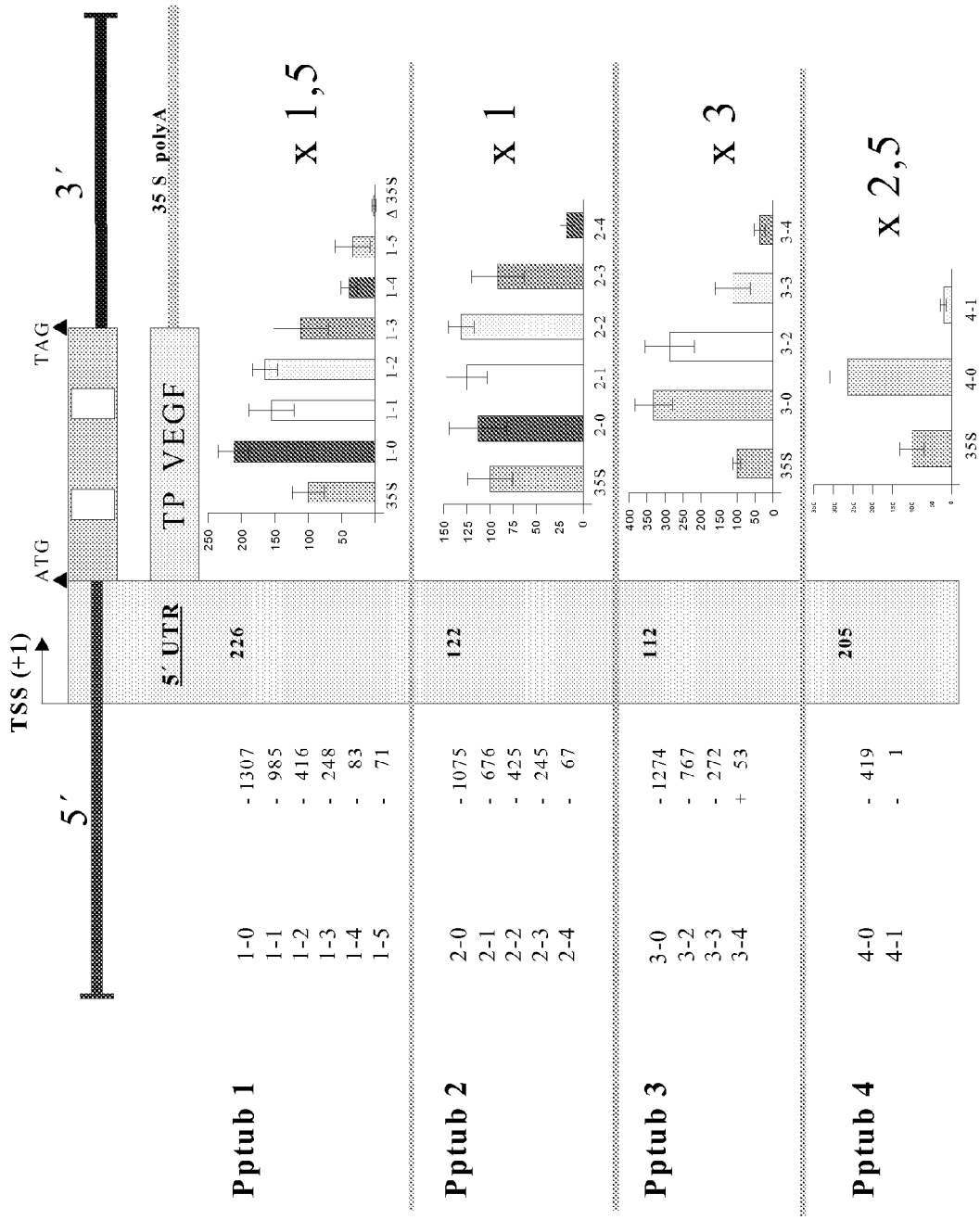
Fig. 2: Analysis of expression promoting regions of β-tubulins in Physcomitrella patens

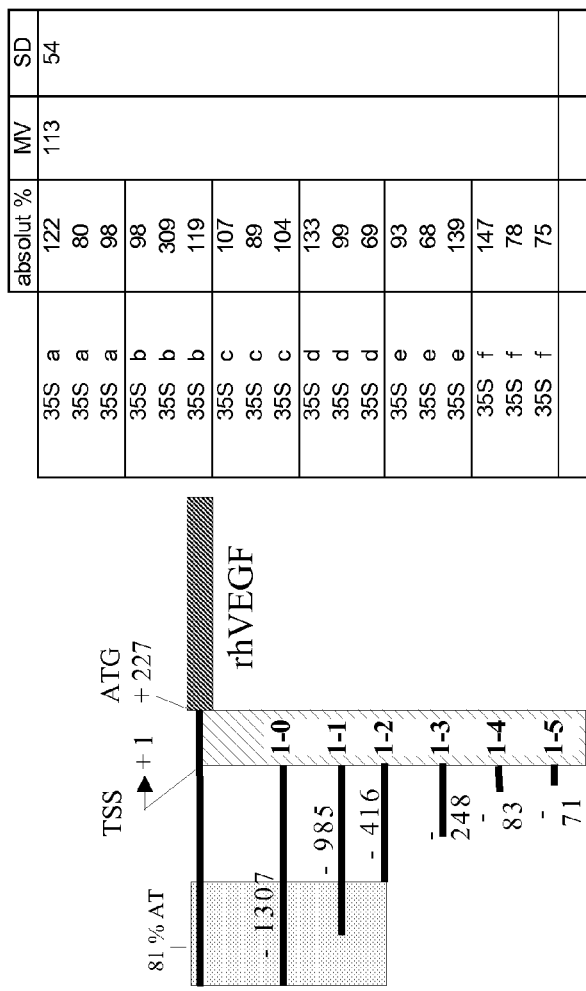
Fig. 3: Analysis of expression promoting regions of Pptub 1 by transient transformation of rhVEGF constructs

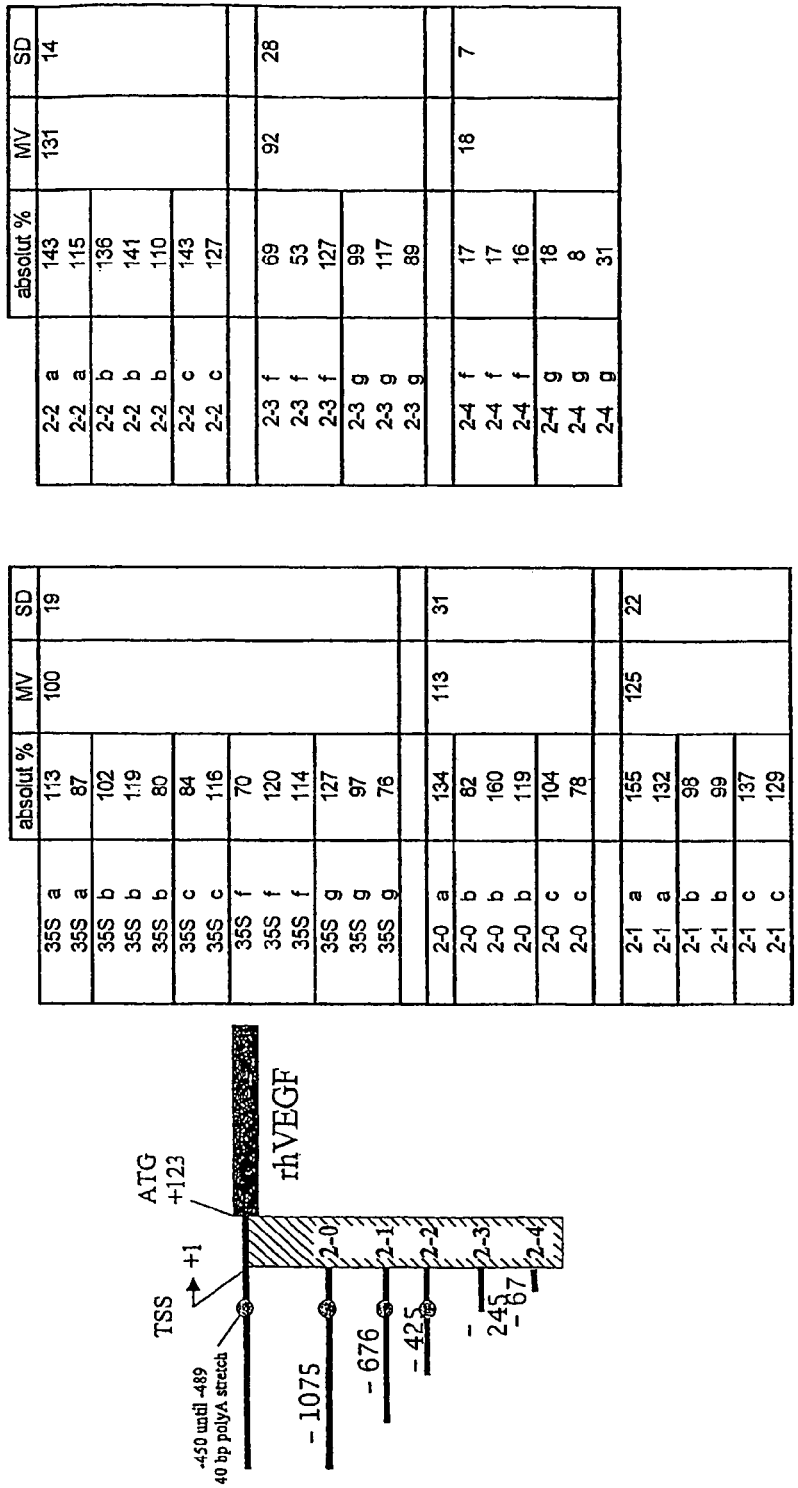
Fig. 4: Analysis of expression promoting regions of Pptub 2 by transient transformation of rhVEGF constructs

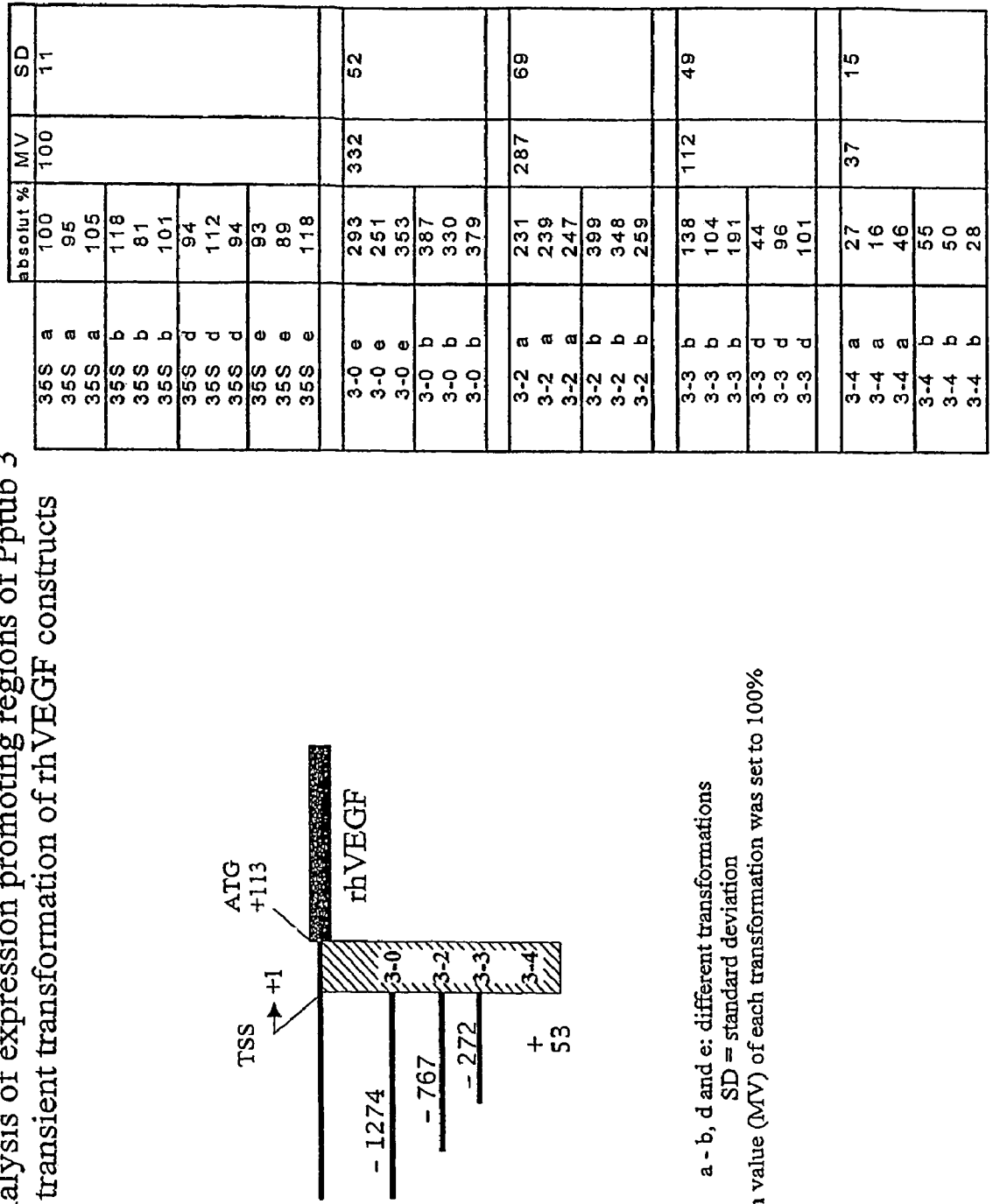
Fig. 5: Analysis of expression promoting regions of Pptub 3 by transient transformation of rhVEGF constructs Fig. 6: Analysis of expression promoting regions of Pptub 4 by transient transformation of rhVEGF constructs
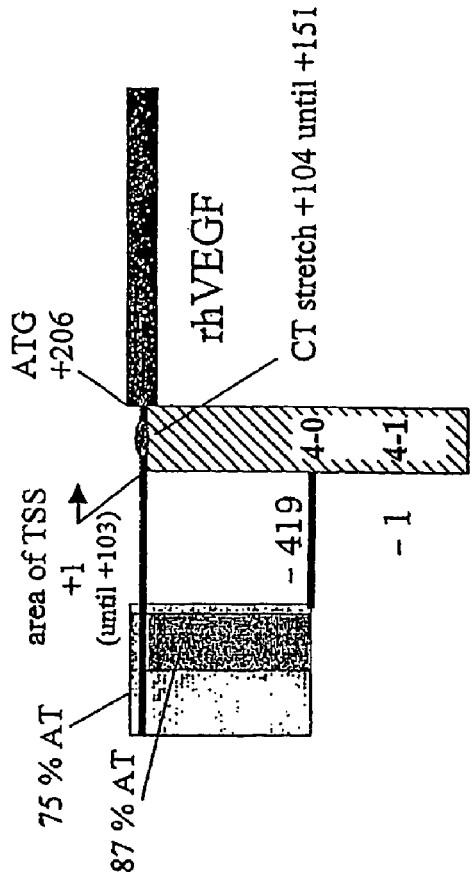
a and c: different transformations
SD = standard deviation
35S mean value (MV) of each transformation was set to 100%

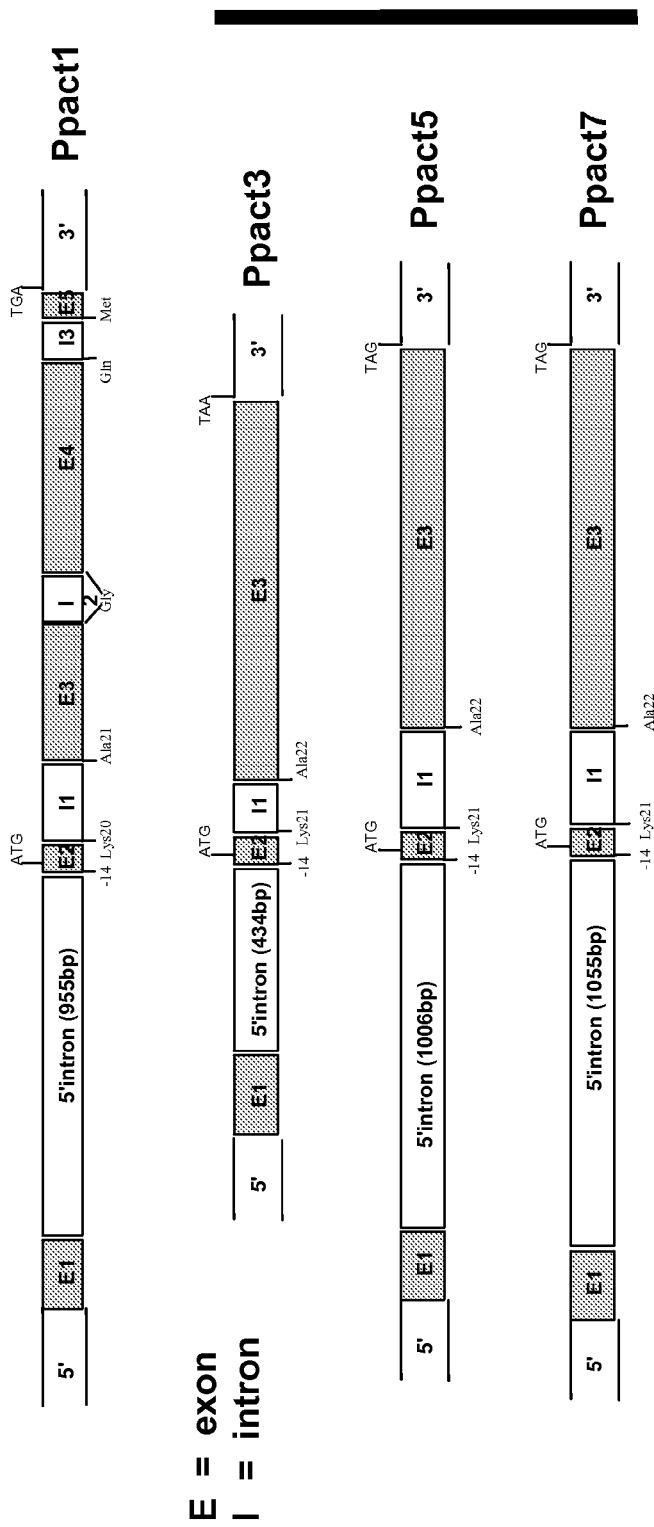
Fig. 7: Genomic structure of *Physcomitrella patens* actin genes.

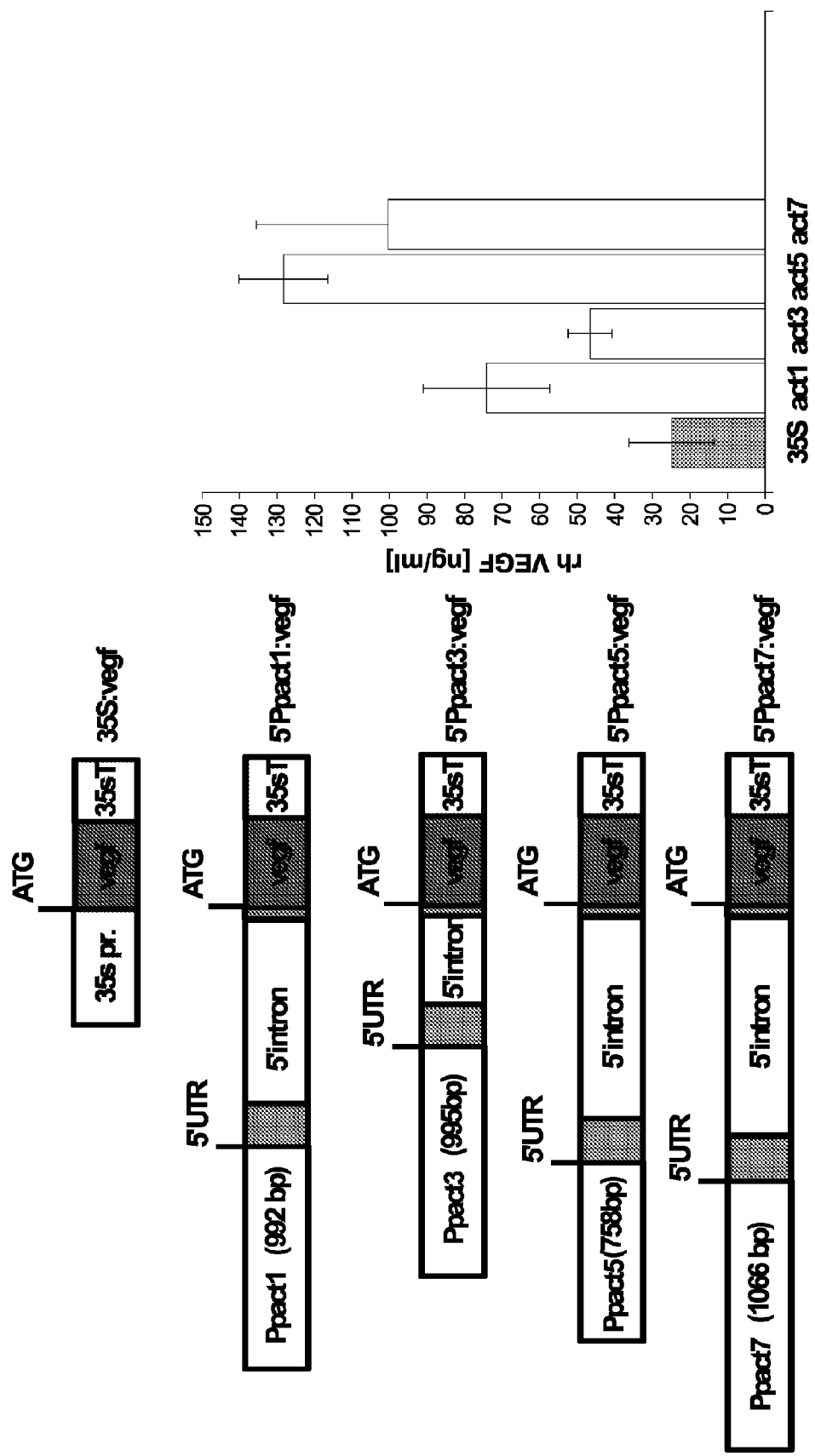
Fig. 8: Comparison of the expression activity of the different 5' actin regions.

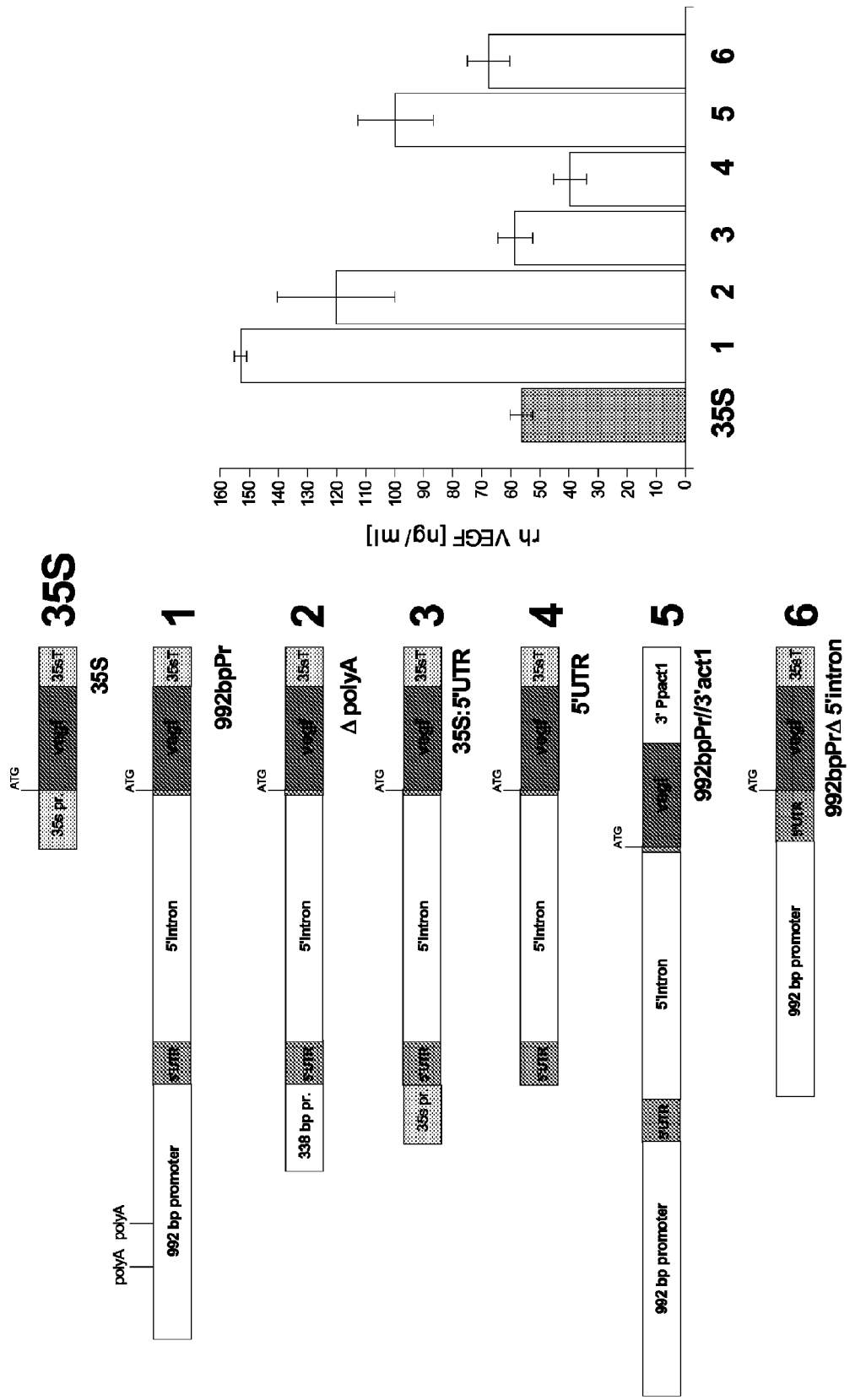
Fig. 9: Ppact1 contructs.

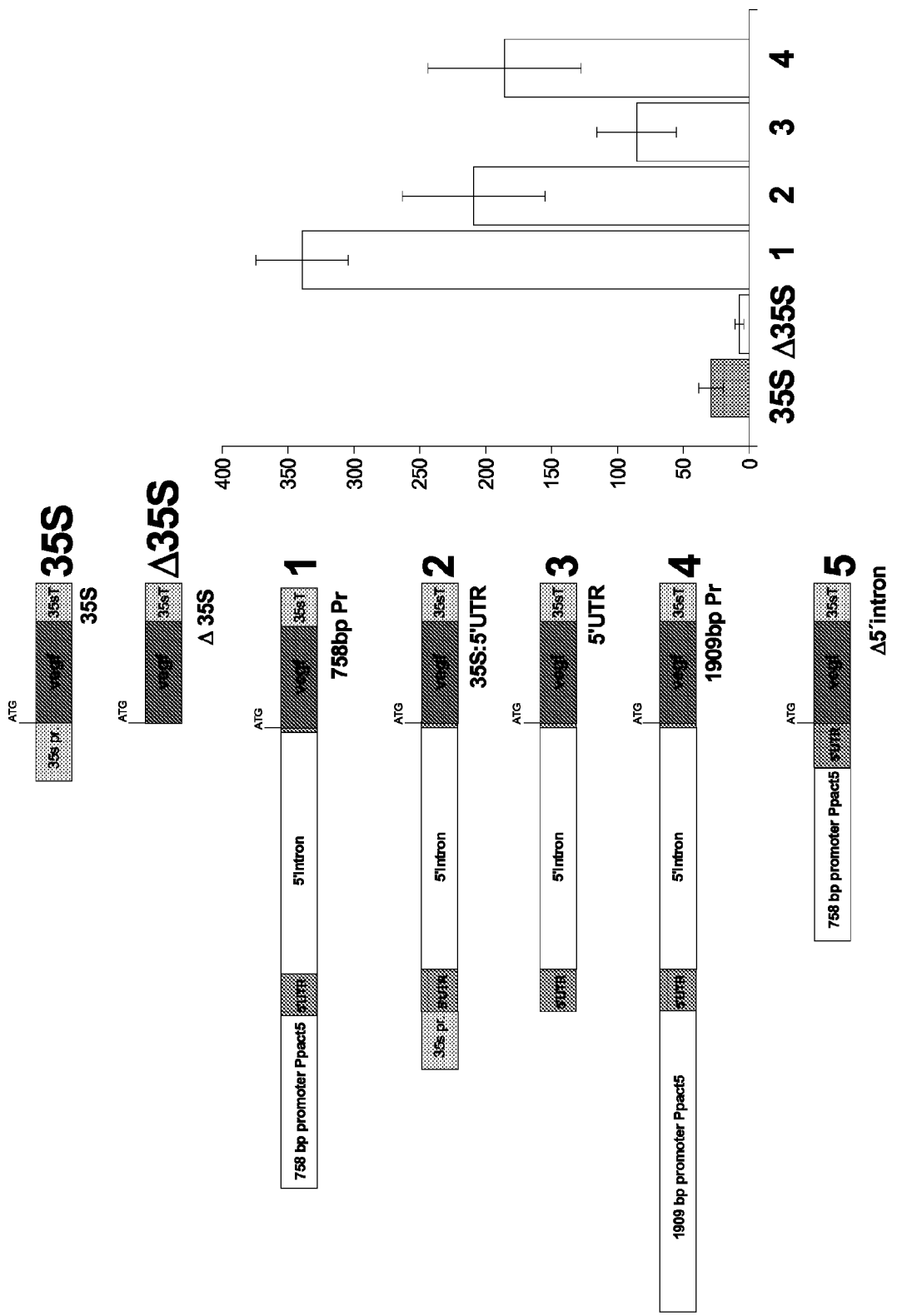
Fig. 10: Ppact 5 constructs.

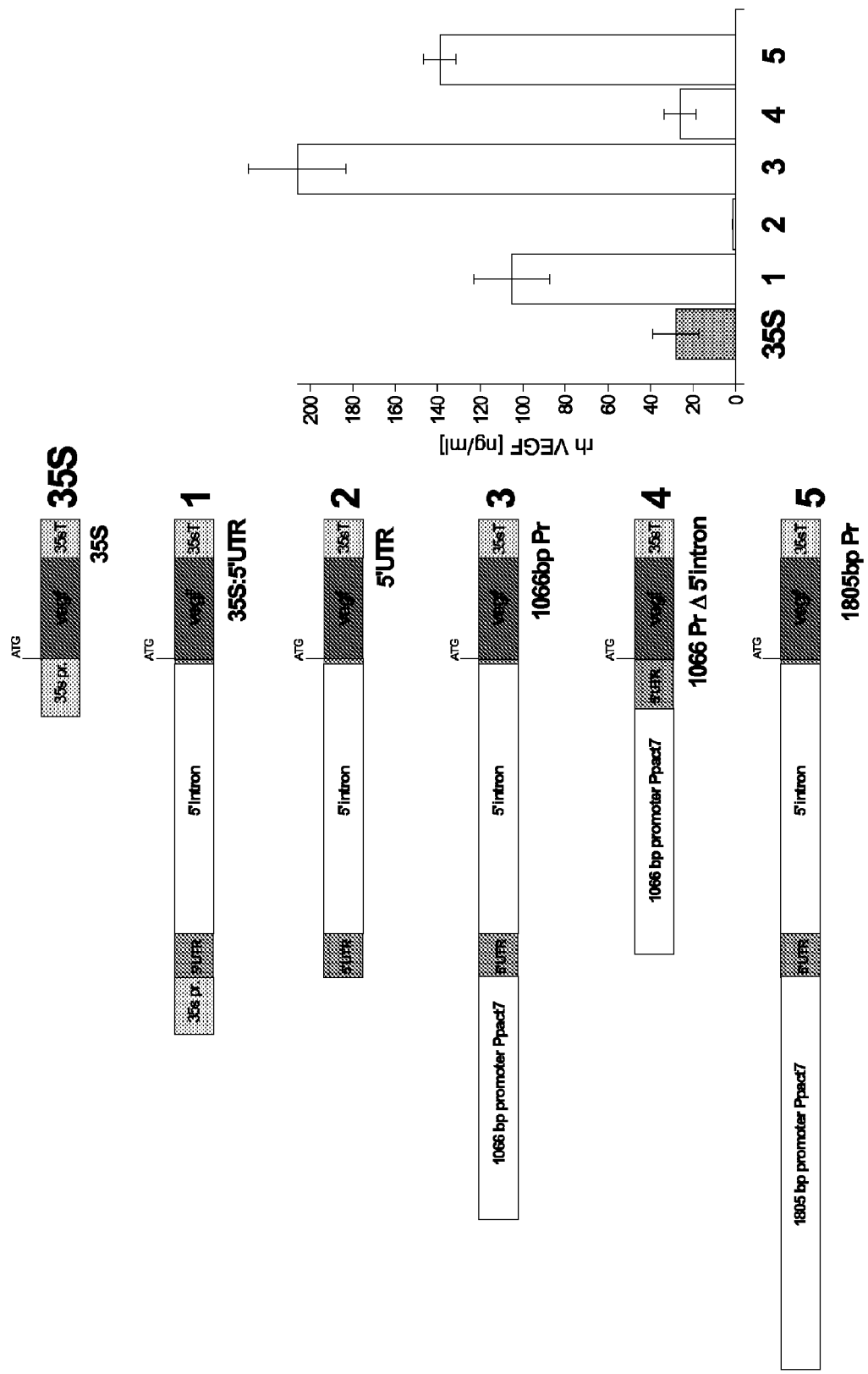
Fig. 11: Ppact 7 constructs.

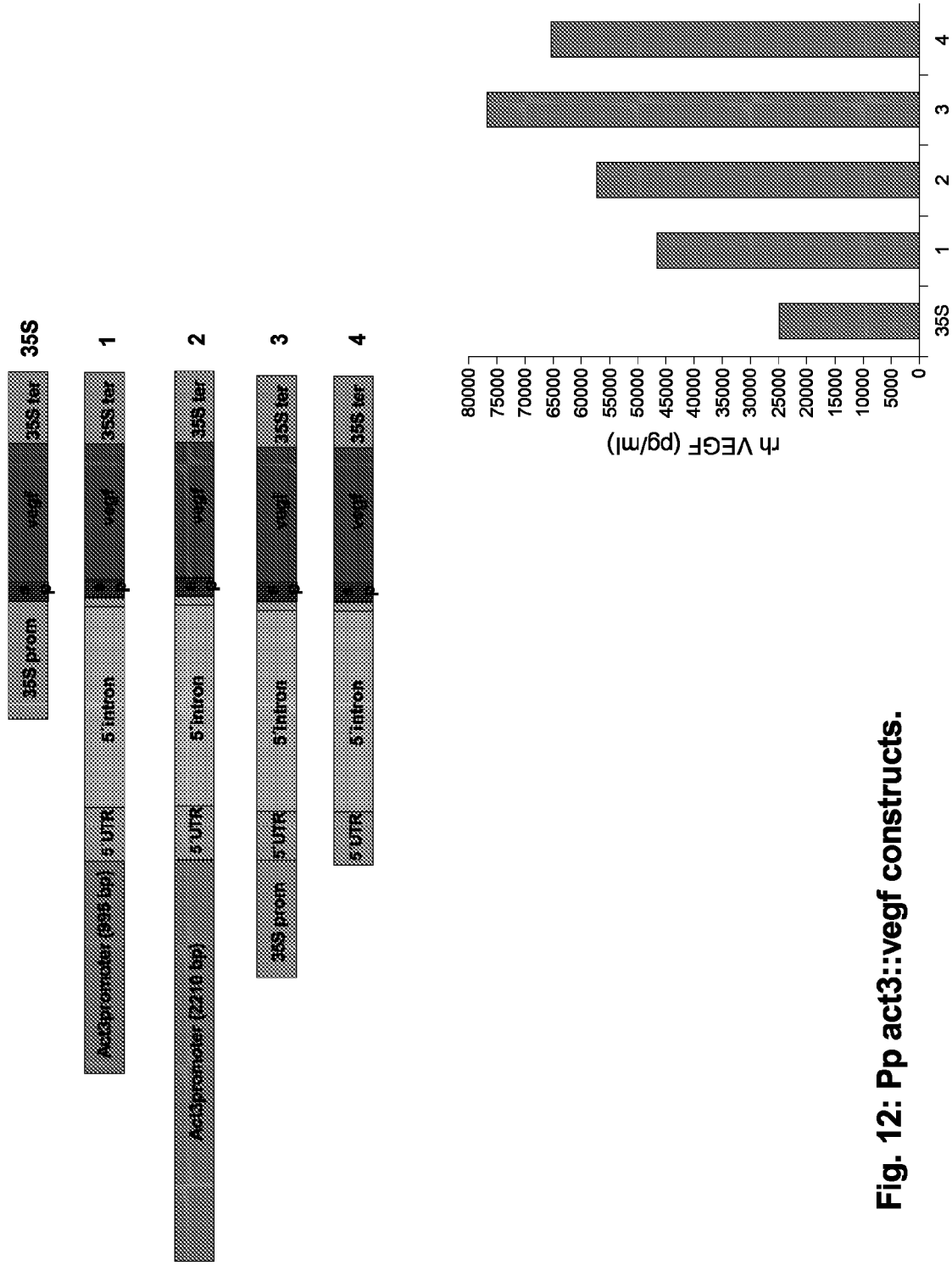
Fig. 12: Pp act3::vegf constructs.

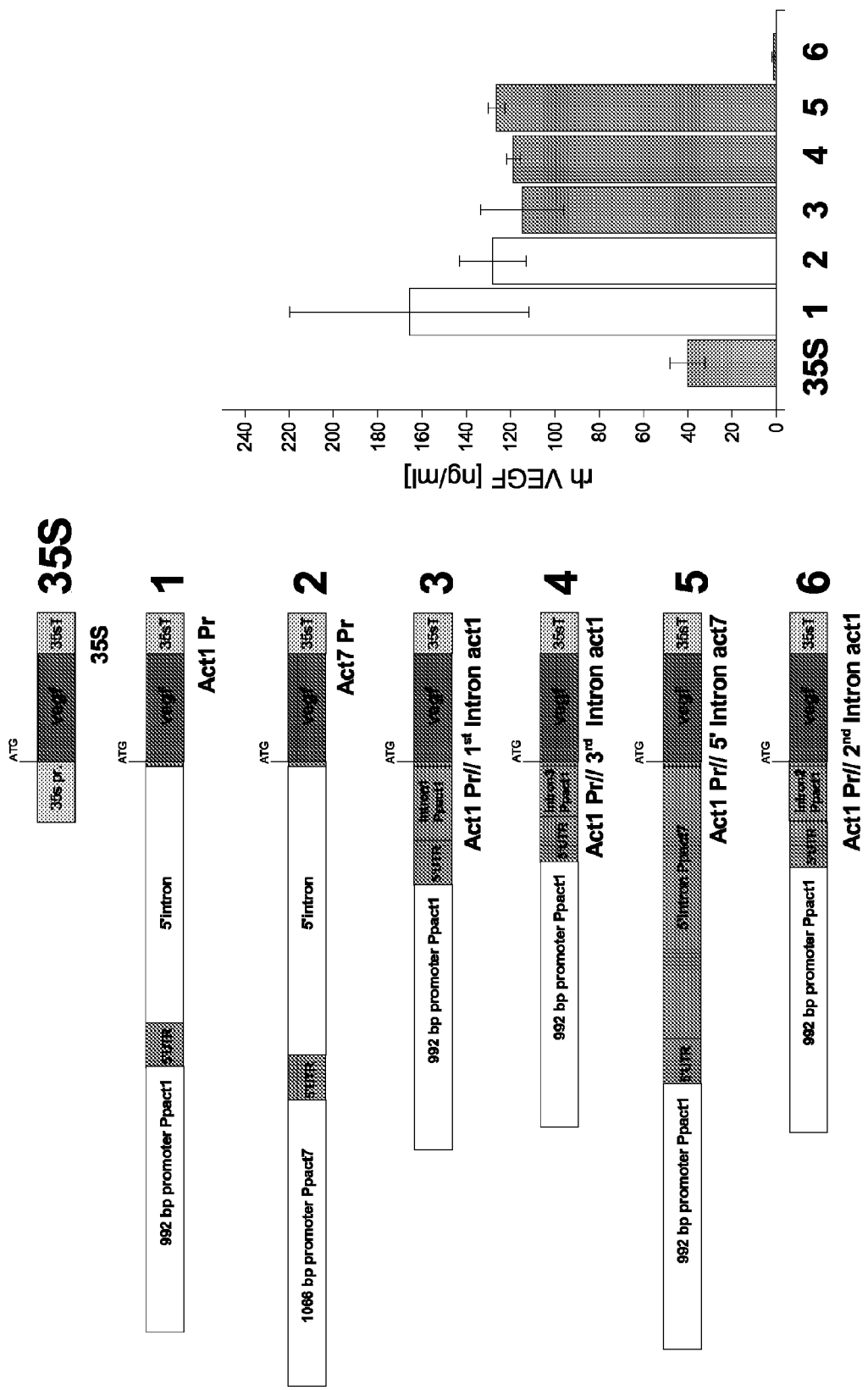
Fig. 13: Ppact1 promoter:5′ intron substitutions.

Fig. 14: Ppact1 promoter:vegf deletion constructs.
1. 5'Ppact1-1821:vegf
2. 5'Ppact1-992:vegf
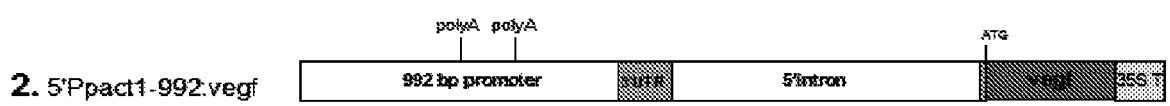
3. 5'Ppact1-790:vegf
4. 5'Ppact1-569:vegf
5. 5'Ppact1-383:vegf
6. 5'Ppact1-237:vegf
7. 5'Ppact1-82:vegf
8. 5'UTR:vegf
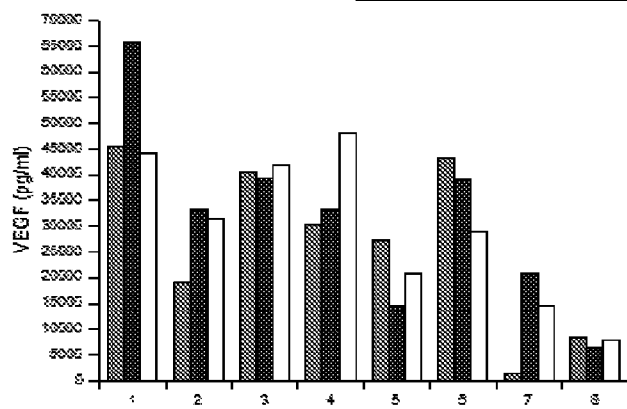

Fig. 15: Ppact3 promoter:vegf deletion constructs.
1. 5'Ppact3-2208:vegf
2. 5'Ppact3-992:vegf
3. 5'Ppact3-821:vegf
4. 5'Ppact3-523:vegf
5. 5'Ppact3-323:vegf
6. 5'Ppact3-182:vegf
7. 5'Ppact3-81:vegf
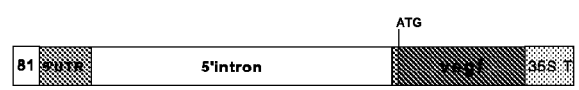
8. 5'UTR:vegf
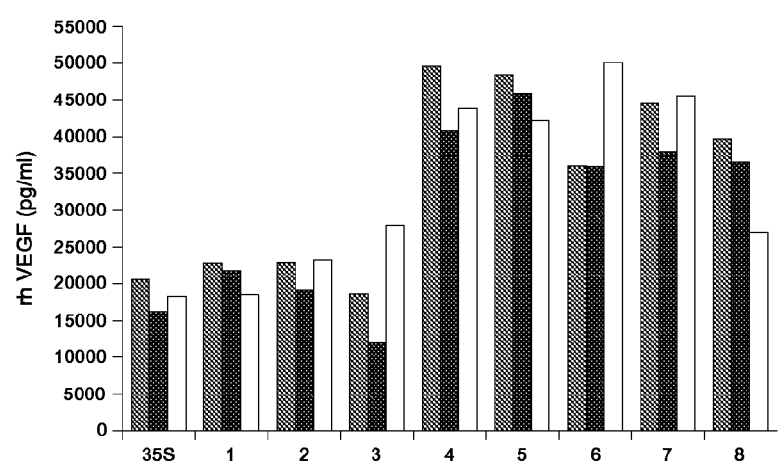

Fig. 16: Ppact5 promoter:vegf deletion constructs.
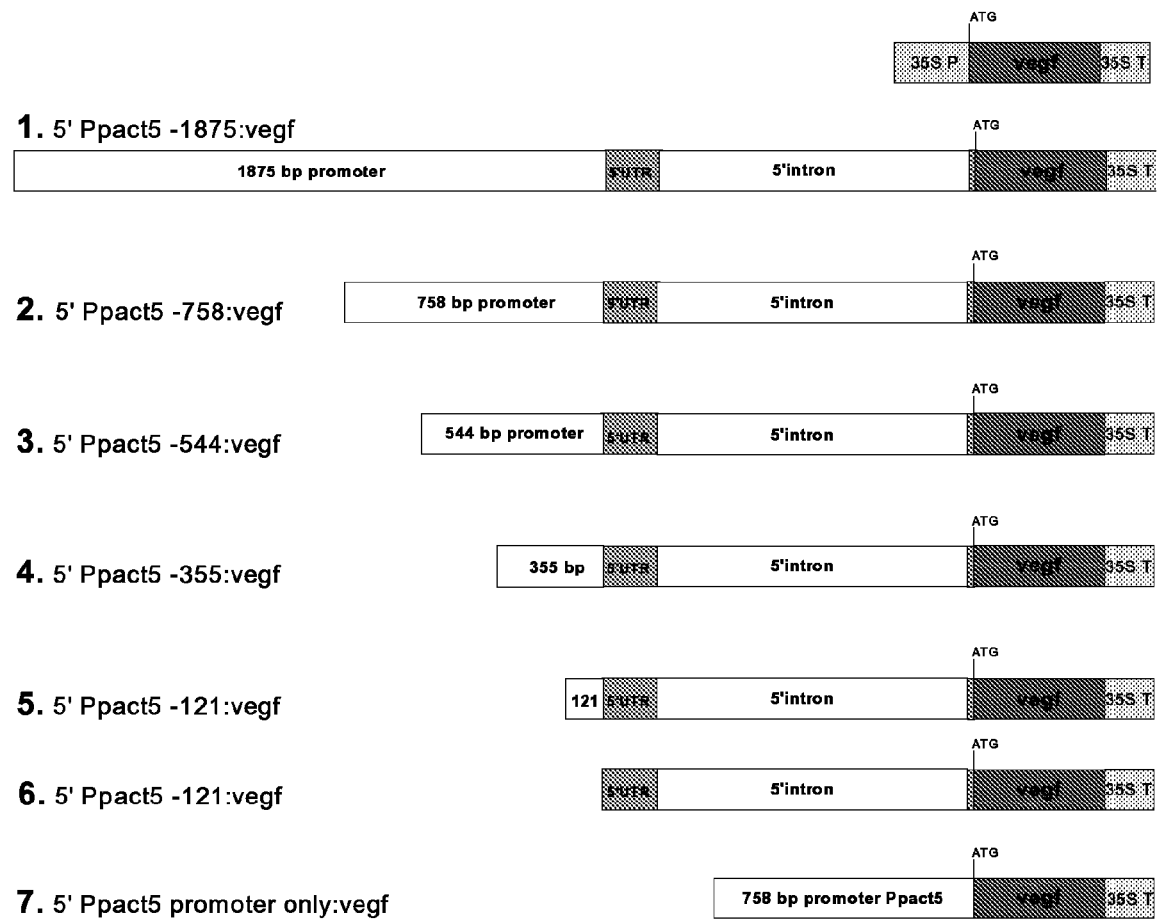
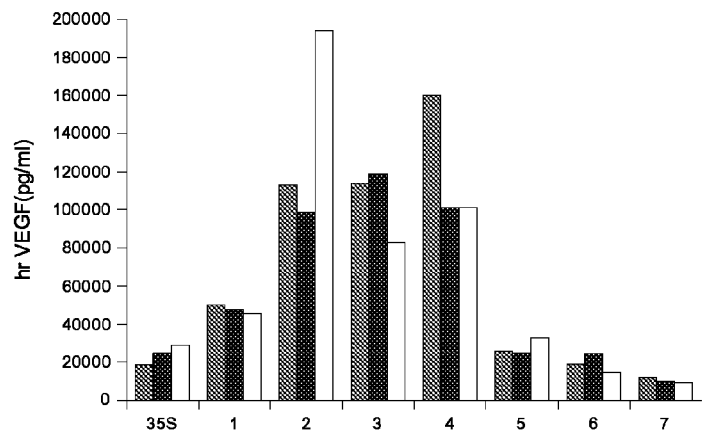

Fig. 17: Ppact7 promoter:vegf deletion constructs.
1. 5' Ppact7 -1790:vegf
2. 5' Ppact7 -1070:vegf
3. 5' Ppact7 -854:vegf
4. 5' Ppact7 -659:vegf
5. 5' Ppact7 -484:vegf
6. 5' Ppact7 -299:vegf
7. 5' Ppact7 -66:vegf
8. 5' UTRact7:vegf
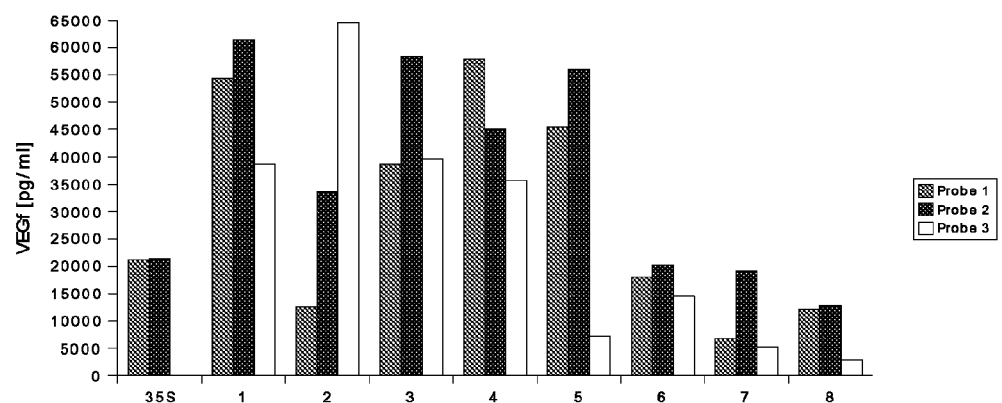

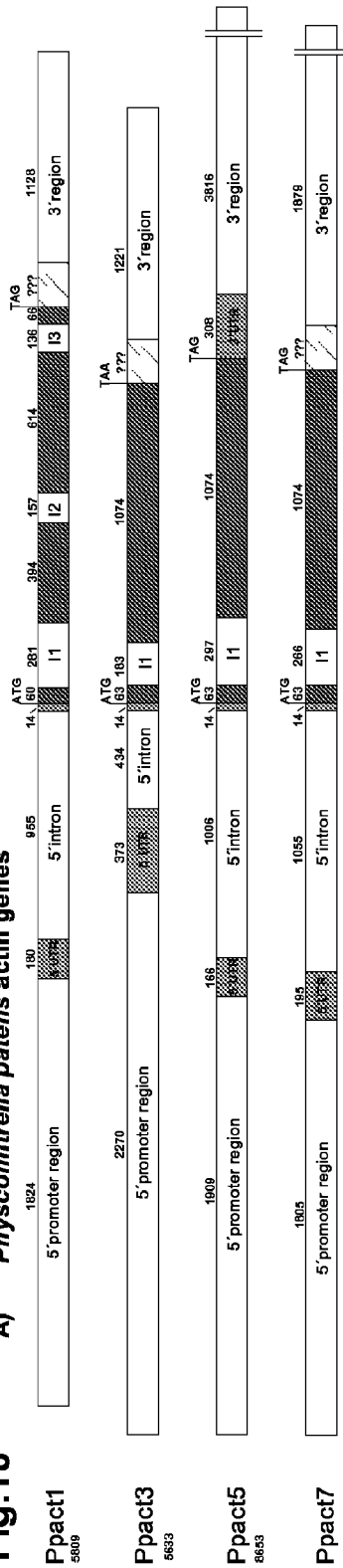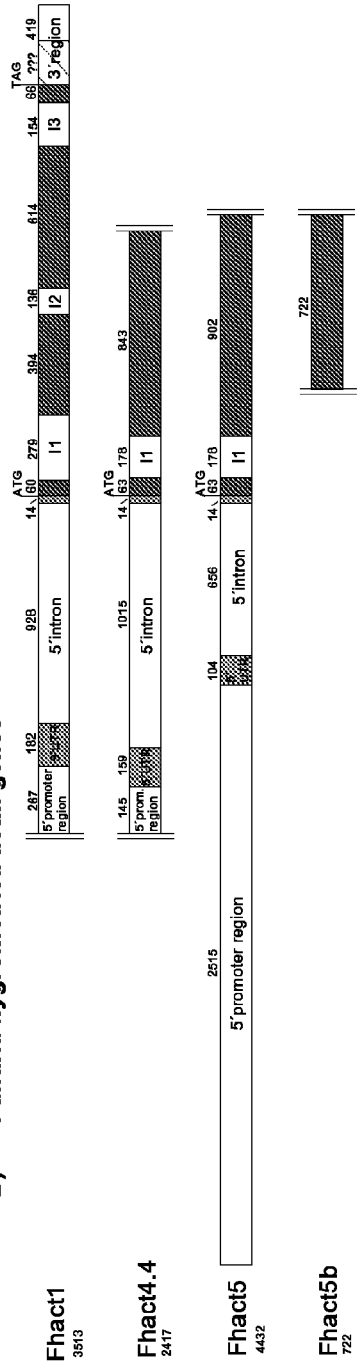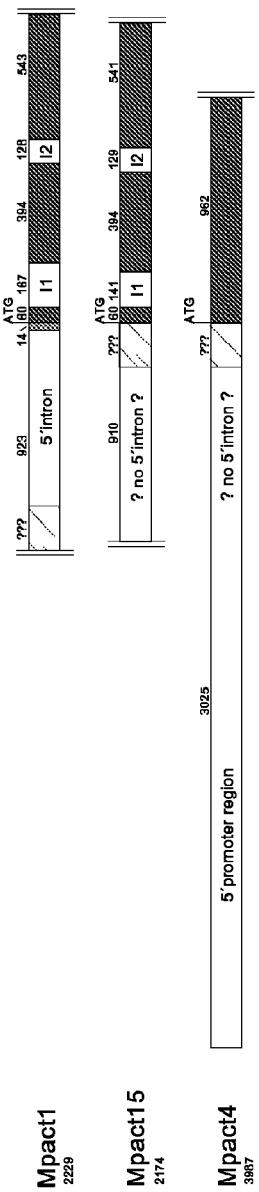
Fig. 18

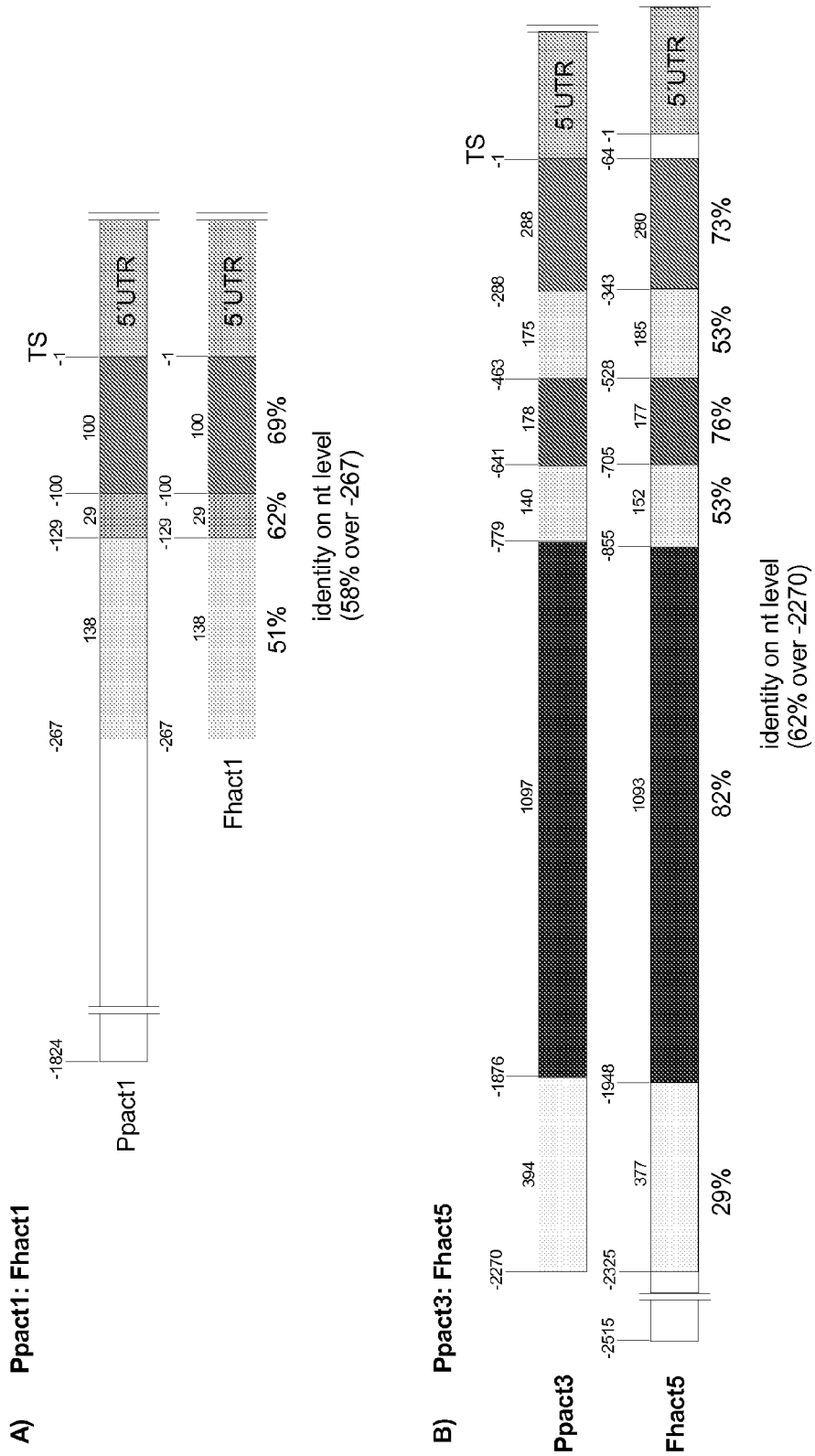
Fig.: 19 Comparison of promoter sequences of homologous actin genes from *Physcomitrella patens* and *Funaria hygrometrica*

MOSS EXPRESSING PROMOTION REGIONS

This application is a continuation of U.S. application Ser. No. 10/568,156, filed on Feb. 13, 2006, now U.S. Pat. No. 7,538,259 which is a U.S. national phase application under 35 U.S.C. §371 of International Application No. PCT/EP2004/008580 filed Jul. 30, 2004, which claims priority to European Application No. 03450184.1 filed Aug. 11, 2003. The entire text of each of the above-referenced disclosures is specifically incorporated by reference herein without disclaimer.

The invention relates to isolated nucleic acid molecules promoting expression of polypeptides in genetically modified eukaryotic host cells.

The expression of proteinaceous substances (proteins, peptides, polypeptides, fragments thereof, as well as posttranslationally modified forms of these molecules are hereinafter referred to as "polypeptides" (synonymously used together with "protein", e.g. in the example part) in genetically modified cells is a major source for providing preparations of such often rare and valuable substances. For expressing such polypeptides in genetically modified host cells, the presence of a DNA region is necessary which positively controls ("activates", "promotes") this expression. Promoters are important examples for such regions allowing RNA polymerases to bind to the DNA for initiating transcription into mRNA (Watson et al., "Recombinant DNA" (1992), Chapter I.1 and 2).

Mosses have gained increasing attention as useful objects for research for plant physiology and development, since their simple nature (mosses are situated at the base of higher-plant-evolution) provides insights into the complex biology of higher plants. The simple morphology of mosses and the advantageous culturing possibilities has made them popular model organisms for studies of plant physiology and developmental biology: Moss species may be cultured without difficulty under controlled conditions, using in vitro techniques including axenic culture, not only in petri dishes, but also in liquid culture e.g. in bioreactors. The haploid gametophyte can be grown photoautotrophically in sterile culture and easily observed at the cellular level.

Another major advantage of mosses is their transformation capacity: Despite numerous studies, the ratio of targeted integration events in plants hardly reaches $10^{-4}$, which prevents the general use of gene targeting approaches for plant functional genomics. In contrast to all other plants having been tested so far, integration of homologous DNA sequences in the genome of mosses (especially the established moss model organisms such as *Physcomitrella patens* (for a review of its molecular genetics: Reski, 1999)) occurs predominantly at targeted locations by homologous recombination. Transformation of mosses is usually and easily performed via PEG-mediated uptake of plasmid DNA by protoplasts, DNA transfer by microprojectile bombardment, electroporation and microinjection (Cove et al., 1997). Depending on the design of the transforming construct predominantly random or targeted integration occurs.

Despite the use of mosses as scientific tools for plant physiology research, the use of mosses for producing recombinant heterologous polypeptides in moss cells has been rather limited so far, although efficient production methods have become available (e.g. culturing protonema moss tissue as described in EP 1 206 561 A).

A major limitation of transformation technologies in eukaryotic host cells, especially in animal cells or cells of higher plants, has always been the lack of an efficient promoter for high constitutive expression of foreign genes in such transgenic host cells. The cauliflower mosaic virus (CaMV) 35S promoter has been widely used for this purpose in a number of plant transformation systems (see e.g. WO 01/25456 A), however, the CaMV 35S promoter has shown low activity in some plant species (specially monocots, such as rice (McElroy et al., 1991)). For monocot transformation the rice actin 1 5' region has been used for heterologous expression of proteins (McElroy et al., 1991). Nevertheless, the continuing need to provide novel expression promoting means for the expression of recombinant (foreign) polypeptides in genetically modified eukaryotic host cells still exists.

For mosses, especially for *Physcomitrella patens*, up to now, no homologous (in this case homologous is defined as: moss derived) suitable nucleus derived expression promoters or other nucleus derived expression promoting sequences have been published so far (Holtdorf et al., 2002). Researchers have therefore used heterologous (in this case heterologous is defined as: not moss derived) promoters for the expression of selection marker genes and other genes of interest. However, only a few of such promoters have been reported to function reliably in certain mosses (e.g. the CaMV 35S-promoter; summarised in Holtdorf et al., 2002; CaMV 35S-promoter does not work in certain other species (Zeidler et al., 1999); TET-promoter (reviewed in Reski (1998)). Therefore, other means for genetically manipulating mosses have been developed in the art, e.g. gene-trap and enhancer trap systems (Hiwatashi et al., 2001; however, also using (a shortened version of the) CaMV 35S promoter; the authors showed in transient expression experiments that also this shortened version of the 35 S promoter was functioning as a weak promoter; in fact, this paper relates to the expression of a reporter gene in enhancer-trap strains but does not reveal any correlation of this expression to any regulatory element of mosses).

Whereas in the above mentioned research in mosses using homologous recombination the use of heterologous promoters is necessary (and therefore homologous promoters are not needed, moreover they are in most cases not useful), the need for a suitable moss derived expression promoting means for industrially using mosses for the production of recombinant polypeptides or for the overexpression of homologous polypeptides is present and yet unsolved. Such expression promoting means should allow a stable and constitutive expression under the applied culturing conditions and should preferably enable a comparable or even higher expression performance as the CaMV 35S promoter.

Therefore, the present invention provides an isolated nucleic acid molecule encoding a moss expression promoting region (MEPR), i.e. an expression promoting region from a wild type moss. With the present invention moss derived expression regions (i.e. nucleus derived regions originating from wild type mosses) are provided which allow a constitutive expression in genetically modified host cells, especially mosses, thereby addressing the needs for such tools raised in the prior art (Holtdorf et al., 2002; Schaefer et al., 2002).

An essential feature of the MEPRs according to the present invention is also that the expression promoting activity of the MEPRs is at least 30%, preferably at least 50%, of the expression promoting activity of a working heterologous promoter in the specific host cell (e.g. CaMV 35S for the expression of a recombinant polypeptide in *Physcomitrella patens*), because moss promoters which do not have such an expression promoting activity cannot be properly used for solving the objects of the present invention and are therefore not regarded as MEPRs.

The MEPRs according to the present invention are therefore isolated from the nucleus of wild type mosses, i.e. mosses which have not been genetically modified by the introduction of promoters from non-moss species (e.g. promoters of higher plants or (plant) pathogens, such as the CaMV 35S promoter, or the TET promoter). It is also clear that MEPRs with minor sequence variation (e.g. exchange of 1, 2, 3, 4 or 5 bases in regions which do not negatively affect (abolish) the expression promoting activity), which may occur e.g. due to natural strain sequence variability or due to events during isolation of the MEPRs are also regarded as MEPRs according to the present invention. Methods for analysing the expression promoting activity or for analysing the effect of such minor sequence variation on this activity are available to the skilled man (e.g. by comparison with the known CaMV 35S constructs) and also described in the example section below.

According to the present invention MEPRs promoting expression which is not sphorophyte specific, are defined as constitutive MEPRs, preferably MEPRs promote expression in gametophyte derived cells, more preferably MEPRs promote expression in protonema cells.

According to the present invention constitutive expression is preferably defined as the expression of a protein resulting in detectable amounts of this protein under liquid culture conditions generally used for photoautotrophically grown mosses, e.g. flask cultures, bioreactor cultures (EP 1 206 561 A), conditions used for the transient expression system described beneath. Therefore, constitutive expression has to be given for the MEPRs according to the present invention preferably without the need of specific culturing additives, preferably also without the need of added sugars, phytohormones or mixtures of such sub-stances in the culture medium. The constitutive expression has to be performed in a steady mode; yet it can be transient.

The terms "moss" or "mosses" as used in the present specification encompasses all bryophytes (hepatics or liverworts, hornworts and mosses). Characteristic for mosses is their heteromorphic Generationswechsel, the alternation of two generations which are distinct from each other in terms of nuclear DNA amounts and morphology. The diploid sporophyte is photosynthetically active only in its youth and requires supply from the dominating, green, haploid gametophyte. The gametophyte exists in two morphologically distinct forms: the juvenile gametophyte, called protonema and the adult gametophyte, called gametophor. In contrast to the protonema, the adult gametophyte (gametophore) bears the sex organs.

In the context of the presented invention transient expression is defined as introduction of an episomal nucleic acid-based construct (e.g. MEPRs and gene of interest) as described below into a moss protoplast and causing or allowing transient expression from the vector that results preferably in turn to the secretion of extracellular protein into the medium. Protoplasts are derived from moss cells, preferably, from gametophytic cells, more preferably from protonema cells.

Although the MEPRs according to the present invention may be taken from any moss species, the MEPRs are preferably isolated from common model moss species. The MEPRs are therefore preferably isolated from *Physcomitrella, Funaria, Sphagnum, Ceratodon, Marchantia* and *Sphaerocarpos*, especially of *Physcomitrella patens, Funaria hygrometrica* and *Marchantia polymorpha*.

Suitable MEPRs according to the present invention are selected from the Seq. ID Nos. 1 to 27 or expression promoting fragments thereof. An "expression promoting fragment" is a fragment of an MEPR which has an expression promoting activity of the MEPRs of at least 30%, preferably at least 50%, of the expression promoting activity of a working heterologous promoter in the specific host cell (e.g. CaMV 35S for the expression of a recombinant polypeptide in *Physcomitrella patens*).

The MEPRs according to the present invention may comprise specific regions, such as a promoter region ("promoter"), 5' untranslated regions ("5'-UTRs"), 5'-introns or 3'-UTRs. For some MEPRs, expression promoting fragments exist which only contain the 5'-intron. Usually the promoter is always active alone as an expression promoting fragment. Therefore, the MEPR according to the present invention preferably comprises a moss promoter and preferably a 5'-UTR region and/or a 5'-intron and/or a 3'-UTR.

Although it is often sufficient, if a certain constitutive expression is reached, it is in many cases preferred to achieve a high expression rate, especially for industrially producing recombinant polypeptides. Most of the MEPRs according to the present invention have proven to allow significantly higher expression rates for a given recombinant polypeptide than the CaMV 35S promoter, especially in homologous systems (e.g. a *Physcomitrella* MEPR for expression of a polypeptide in *Physcomitrella*). Therefore, preferred MEPRs according to the present invention have an expression promoting activity being at least equal to the expression promoting activity of cauliflower mosaic virus (CaMV) 35S promoter, especially, but not limited, in the moss species from which the MEPR was isolated. Even more preferred MEPRs have an expression promoting activity being at least 200%, preferably being at least 500%, especially being at least 1000%, of the expression promoting activity of cauliflower mosaic virus (CaMV) 35S promoter, especially, but not limited, in the moss species from which the MEPR was isolated.

The isolated nucleic acid molecules according to the present invention are preferably used to transform a specific host cell for producing a recombinant transgenic polypeptide, preferably, but not limited to, in an industrial scale. Therefore the nucleic acid molecule is provided as a suitable vector allowing transformation and expression of the transgene in the host cell. Among the possibility that an MEPR according to the present invention is used for replacing a natural promoter in mosses, thereby bringing the expression of a homologous moss polypeptide under the control of a MEPR being located at a position in the genome of the moss, where it is normally not present in wild type strains, the prevalent industrial applicability of the present MEPRs is the control of expression of a heterologous ("foreign") gene in a production host cell, specifically a plant cell, especially a moss cell. Therefore, the nucleic acid molecule according to the present invention further comprises a coding region for a recombinant polypeptide product, said coding region being under the control of the MEPR.

It is also advantageous, if the isolated nucleic acid molecules according to the present invention further comprises a selection marker and/or further regions necessary for enabling the appropriate transformation method chosen (see e.g. Cove et al., 1997; Schaefer, 2002). For example, if targeted integration is preferred, the nucleic acid molecule according to the present invention should further comprise sequences which are homologous to genomic sequences of the species to be transformed. Thus, allowing targeted integration of the isolated nucleic acid molecule via homologous recombination into the genome of the species to be transformed.

Moreover, the isolated nucleic acid molecules according to the present invention can be used for screening and defining consensus sequences for expression promoting regions. Finding and screening for such consensus sequences (regions, boxes) which are important and/or essential for expression promoting activity is a valuable asset in recombinant DNA technology, especially with respect to industrial biotechnology using mosses.

According to another aspect, the present invention also relates to a process for the expression of a recombinant polypeptide product in an eukaryotic host cell comprising the following steps:
  providing a recombinant DNA cloning vehicle comprising an isolated nucleic acid molecule encoding an MEPR according to the present invention and optionally a coding region for said recombinant polypeptide product, said coding sequence being under the control of the MEPR of said nucleic acid molecule in said host,
  transforming said eukaryotic host cell which does not naturally harbour said coding sequence in a way that it is under the control of said MEPR,
  culturing the transformed eukaryotic host cell in a suitable culture medium,
  allowing expression of said recombinant polypeptide and isolating the expressed recombinant polypeptide.

As mentioned above, MEPRs according to the present invention in principle have the capability to achieve constitutive expression in various cell types, the eukaryotic host cell is preferably selected from plant cells, preferably moss cells, especially *Physcomitrella patens* cells.

A system which is specifically preferred for the present invention is the culturing in moss protonema cultures (protonema moss tissue). In doing so the method described in the EP 1 206 561 A and the preferred embodiments thereof are explicitly incorporated by reference herein and are immediately applicable to the present invention.

The constitutive expression of the polypeptide with the means according to the present invention is possible without the need for various additives in the culture medium, specifically without additives for specific differentiation or promoting different tissue growth. Therefore, besides electrolytes, selection agents and medium stabilisers, the culture medium preferably does not contain any further additives for cell supply. The culture medium for stably transformed plants is preferably free from added sugars, phytohormones or mixtures thereof. The culture medium for transiently transformed protoplasts is preferably free from added phytohormones.

Preferred moss cells are moss cells of the group *Physcomitrella, Funaria, Sphagnum, Ceratodon, Marchantia* and *Sphaerocarpos*, especially in protonema cultures.

According to another aspect, the present invention also provides the use of an isolated nucleic acid molecule encoding an MEPR for industrially producing a polypeptide, especially for providing recombinant cells producing said polypeptide. The industrial production allows a large scale preparation of a given polypeptide of interest in bioreactors, e.g. in gram amounts or even higher (commercial yields). This in contrast to the production sufficient for research use (mg amounts) or analytical purposes (µg amounts), which may, of course also be performed by the present invention. In transient expression systems, protein amounts sufficient for such analytical purposes can easily be obtained with the present DNA molecules.

Accordingly, the present invention also encompasses the use of an isolated nucleic acid molecule encoding a MEPR for expression of a moss polypeptide, the expression of said moss polypeptide being not naturally controlled by said MEPR, especially for providing recombinant moss cells expressing said polypeptide. This use may be reduced to practice both, for research purposes and for industrial scale production of moss polypeptides.

According to another aspect, the present invention also provides the use of an isolated nucleic acid molecule encoding a MEPR for expression of proteins involved in specific posttranslational modifications (e.g. glycosyltransferases), especially for providing recombinant moss cells expressing polypeptides with posttranslational modifications normally not existing or normally existing in another ratio in untransformed moss cells.

According to another aspect, the present invention also provides the use of an isolated nucleic acid molecule encoding a MEPR for expression of proteins involved in metabolic pathways, especially for providing recombinant moss cells altered in their contents of metabolites e.g. secondary metabolites.

According to another aspect, the present invention also provides the use of an isolated nucleic acid molecule encoding a MEPR for expression of antisense molecules, siRNA molecules or ribozymes especially for providing recombinant moss cells with reduced amounts of specific proteins resulting in altered phenotypes e.g. morphologically, biochemically.

According to another preferred aspect, the present invention also relates to the use of an isolated nucleic acid molecule encoding an MEPR according to the present invention for recombinant expression of posttranslationally modifying proteins, especially for the production of posttranslationally modified proteins. With such a technology, it is possible to produce proteins which are specifically modified posttranslationally (differently than in the native host cell, thereby enabling e.g. plant cells or moss cultures to allow the production of proteins with e.g. mammal or even human glycosylation patterns. Examples wherein such techniques are applied with specific glycosyltransferases are described e.g. in WO 00/49153 A and WO 01/64901 A.

Another preferred use of the isolated nucleic acid molecule encoding an MEPR according to the present invention relates to the in vitro expression of recombinant proteins. The technique of in vitro translation allows a more controlled production of the recombinant product without the need to accept the uncertainties being connected with host cells.

Another preferred use of the nucleic acid molecule according to the present invention is their use for recombinant expression of metabolism modifying proteins, e.g. proteins which modify the (posttranslational) modification of a translated amino acid chain (see e.g. Berlin et al, 1994).

The present invention is further illustrated by the following examples and the figures, yet without being restricted thereto.

FIGURES

FIG. 1 β-tubulin genes in *Physcomitrella patens*,

FIG. 2 Analysis of expression promoting regions of β-tubulins in *Physcomitrella patens*, FIG. 3 Analysis of expression promoting regions of Pptub 1 by transient transformation of rhVEGF constructs, FIG. 4 Analysis of expression promoting regions of Pptub 2 by transient transformation of rhVEGF constructs, FIG. 5 Analysis of expression promoting regions of Pptub 3 by transient transformation of rhVEGF constructs, FIG. 6 Analysis of expression promoting regions of Pptub 4 by transient transformation of rhVEGF constructs, FIG. 7 Genomic structure of *Physcomitrella patens* actin genes, FIG. 8 Comparison of the expression activity of the different 5'actin regions, FIG. 9 Ppact1 constructs, FIG. 10 Ppact 5 constructs, FIG. 11 Ppact 7 constructs,
FIG. 12 Ppact3::vegf constructs,
FIG. 13 Ppact1 promoter:5' intron substitutions,
FIG. 14 Ppact1 promoter:vegf deletion constructs,
FIG. 15 Ppact3 promoter:vegf deletion constructs,
FIG. 16 Ppact5 promoter:vegf deletion constructs,
FIG. 17 Ppact7 promoter:vegf deletion constructs,
FIG. 18 Actin genes in various moss species, and
FIG. 19 Comparison of promoter sequences of homologous actin genes from *Physcomitrella patens* and *Funaria hygrometrica*

MATERIAL AND METHODS

Plant Material

*Physcomitrella patens* (Hedw.) B.S.G. has been characterised previously (Reski et al. 1994)). It is a subculture of strain 16/14 which was collected by H. L. K. Whitehouse in Gransden Wood, Huntingdonshire, UK and was propagated by Engel (1968; Am J Bot 55, 438-446).

Standard Culture Conditions

Plants were grown axenically under sterile conditions in plain inorganic liquid modified Knop medium (1000 mg/l Ca(NO$_3$)$_2$×4H$_2$O 250 mg/l KCl, 250 mg/l KH$_2$PO$_4$, 250 mg/l MgSO$_4$×7H$_2$O and 12.5 mg/l FeSO$_4$×7H$_2$O; pH 5.8 (Reski and Abel (1985) Planta 165, 354-358). Plants were grown in 500 ml Erlenmeyer flasks containing 200 ml of culture medium or on 9 cm Petri dishes with solidified Knop medium (10 g/l agar). Flasks were shaken on a Certomat R shaker (B. Braun Biotech International, Germany) set at 120 rpm. Conditions in the growth chamber were 25+/−3° C. and a light-dark regime of 16:8 h. Cultures were illuminated from above by two fluorescent tubes (Osram L 58 W/25) providing 35 micromol/m$^{-2}$s$^{-1}$. Subculturing of liquid cultures was done once a week by disintegration using an Ultra-Turrax homogenizer (IKA, Staufen, Germany) and inoculation of two new 500 ml Erlenmeyer flasks containing 100 ml fresh Knop medium. Additionally, cultures were filtered 3 or 4 days after disintegration and were transferred into fresh Knop medium.

Bioreactor cultures were grown in Knop medium or in 1/10 Knop medium, respectively, in stirred tank glass bioreactors (Aplikon, Schiedam, The Netherlands) with a working volume of 5 liters (as described in Hohe and Reski, Plant Sci. 2002, 163, 69-74). Stirring was performed with a marine impeller running with a speed of 500 rpm, the cultures were aerated with 0.3 vvm [(aeration volume)/(medium volume)/min] air. The culture temperature of 25° C. in the vessel was controlled by a double jacket cooling system. Light intensity was 50 micromol/m$^{-2}$s$^{-1}$ provided by fluorescent tubes (Osram L 8W/25) with a light/dark rhythm of 16/8 h. The pH-value in the cultures (pH 6.5-7.0) was not adjusted.

Protoplast Isolation

Different protocols for the isolation of protoplasts (Grimsley et al. 1977; Schaefer et al. 1991; Rother et al. 1994; Zeidler et al. 1999; Hohe and Reski 2002; Schaefer 2001) have been described for *Physcomitrella patens*. For the work presented herein, a modification/combination of the previously described methods was used:

Moss tissue was cultivated for 7 days in Knop medium with reduced (10%) Ca(NO$_3$)$_2$ content. Cultures were filtered 3 or 4 days after disintegration and were transferred into fresh Knop medium with reduced (10%) Ca(NO$_3$)$_2$ content. After filtration the moss protonemata were preincubated in 0.5 M mannitol. After 30 min, 4% Driselase (Sigma, Deisenhofen, Germany) was added to the suspension. Driselase was dissolved in 0.5 M mannitol (pH 5.6-5.8), centrifuged at 3600 rpm for 10 min and sterilised by passage through a 0.22 µm filter (Millex GP, Millipore Corporation, USA). The suspension, containing 1% Driselase (final concentration), was incubated in the dark at RT and agitated gently (best yields of protoplasts were achieved after 2 hours of incubation). The suspension was passed through sieves (Wilson, CLF, Germany) with pore sizes of 100 micrometer and 50 micrometer. The suspension was centrifuged in sterile centrifuge tubes and protoplasts were sedimented at RT for 10 min at 55 g (acceleration of 3; slow down at 3; Multifuge 3 S-R, Kendro, Germany). Protoplasts were gently resuspended in W5 medium (125 mM CaCl$_2$×2H$_2$O; 137 mM NaCl; 5.5 mM glucose; 10 mM KCl; pH 5.6; 660-680 mOsm; sterile filtered; Menczel et al. 1981). The suspension was centrifuged again at RT for 10 min at 55 g (acceleration of 3; slow down at 3; Multifuge 3 S-R, Kendro, Germany). Protoplasts were gently resuspended in W5 medium. For counting protoplasts a small volume of the suspension was transferred to a Fuchs-Rosenthal-chamber.

Transient Transformation

Different protocols for transformation (Schaefer et al. 1991; Reutter and Reski 1996, Schaefer 2001) have been described for *Physcomitrella patens*. For the work presented herein, a modification/combination of the previously described methods was used:

For transformation protoplasts were incubated on ice in the dark for 30 minutes. Subsequently, protoplasts were sedimented by centrifugation at RT for 10 min at 55 g (acceleration of 3; slow down at 3; Multifuge 3 S-R, Kendro). Protoplasts were resuspended in 3M medium (15 mM CaCl$_2$× 2H$_2$O; 0.1% MES; 0.48 M mannitol; pH 5.6; 540 mOsm; sterile filtered, Schaefer et al. (1991) Mol Gen Genet 226, 418-424) at a concentration of 1.2×10$^6$ protoplasts/ml. 250 microliter of this protoplast suspension were dispensed into a new sterile centrifuge tube, 50 microliter DNA solution (column purified DNA in H$_2$O (Qiagen, Hilden, Germany, Hilden, Germany); 10-100 microliter optimal DNA amount of 60 microgram was added and finally 250 microliter PEG-solution (40% PEG 4000; 0.4 M mannitol; 0.1 M Ca(NO$_3$)$_2$; pH 6 after autoclaving) was added. The suspension was immediately but gently mixed and then incubated for 6 min at RT with occasional gentle mixing. The suspension was diluted progressively by adding 1, 2, 3 and 4 ml of 3M medium. The suspension was centrifuged at 20° C. for 10 minutes at 55 g (acceleration of 3; slow down at 3; Multifuge 3 S-R, Kendro). The pellet was resuspended in 400 microliters 3M medium. Cultivation of transformed protoplasts was performed in 48 well plates (Cellstar, greiner bio-one, Frickenhausen, Germany).

Transient transformations were incubated in dim light (4.6 micromols-1 m-2) at 25° C. Samples were taken after 24 h and 48 h, respectively, by carefully replacing half of the medium (200 microliters) by fresh medium. The medium was not replaced completely since the protoplasts have to be kept in liquid. The removed medium (including recombinant protein) was stored at −20° C. The 48 h samples were measured in an ELISA.

Stable Transformation

Different protocols for transformation (Schaefer et al. 1991; Reutter and Reski 1996, Protocol Schaefer 2001) have been described for *Physcomitrella patens*. For the work presented herein, a modification/combination of the previously described methods was used:

For transformation protoplasts were incubated on ice in the dark for 30 minutes. Subsequently, protoplasts were sedimented by centrifugation at RT for 10 min at 55 g (acceleration of 3; slow down at 3; Multifuge 3 S-R, Kendro). Protoplasts were resuspended in 3M medium (15 mM $CaCl_2 \times 2H_2O$; 0.1% MES; 0.48 M mannitol; pH 5.6; 540 mOsm; sterile filtered, Schaefer et al. (1991) Mol Gen Genet 226, 418-424) at a concentration of $1.2 \times 10^6$ protoplasts/ml. 250 microliter of this protoplast suspension were dispensed into a new sterile centrifuge tube, 50 microliter DNA solution (column purified DNA in $H_2O$ (Qiagen, Hilden, Germany, Hilden, Germany); 10-100 microliter optimal DNA amount of 60 microgram was added and finally 250 microliter PEG-solution (40% PEG 4000; 0.4 M mannitol; 0.1 M $Ca(NO_3)_2$; pH 6 after autoclaving) was added. The suspension was immediately but gently mixed and then incubated for 6 min at RT with occasional gentle mixing. The suspension was diluted progressively by adding 1, 2, 3 and 4 ml of 3M medium. The suspension was centrifuged at 20° C. for 10 minutes at 55 g (acceleration of 3; slow down at 3; Multifuge 3 S-R, Kendro). The pellet was re-suspended in 3 ml regeneration medium. Selection procedure was performed as described by Strepp et al. (1998).

ELISA

Recombinant VEGF121 expressed by transient transformed moss protoplasts was quantified by ELISA (R&D Systems, Wiesbaden, Germany). The ELISA was performed according to the instructions of the manufacturer. The samples were diluted for quantification.

Bacterial Strains and Cloning Vectors

For all cloning and propagation experiments *Escherichia coli* strain Top10 (Invitrogen, Karlsruhe, Germany) was used. For cloning of DNA-fragments pCR2.1-TOPO (Invitrogen, Karlsruhe, Germany), pCR4-TOPO (Invitrogen, Karlsruhe, Germany), pZErO-2 (Invitrogen, Karlsruhe, Germany) or pRT101 (Töpfet al. (1987), NAR, 15, p 5890) were used as vectors.

Genomic DNA: Preparation, Digestion, Ligation

*Physcomitrella patens* genomic DNA was isolated from 13 days old protonemata following the CTAB protocol (Schlink and Reski, 2002).

Genomic DNA (3-5 micrograms) was digested with 30 units of various restriction endonucleases (e.g. BamHI, EcoRI, HindIII, KpnI, NcoI, NdeI, PaeI, PagI, XbaI; all MBI Fermentas, St. Leon-Rot, Germany) in a total volume of 30 microliters for two hours at 370° C., using one endonuclease per digest. Digested DNA was purified using PCR Purification Columns (Qiagen, Hilden, Germany), following the suppliers manual (30 microliters digest+200 microliters buffer PB). Elution was done in 50 microliters Elution Buffer (EB; Qiagen, Hilden, Germany). Prior further treatment, 10 microliters of the eluate were analysed on an agarose gel (0.5%).

The remaining DNA was religated with 5 units T4 Ligase (MBI Fermentas, St. Leon-Rot, Germany) in a total volume of 300 microliters for two hours at RT and additional two days at 4° C. Prior addition of the enzyme ligation mixtures were put for five minutes at 50° C. and then on ice, in order to melt sticky end basepairing. After ethanol precipitation with 0.3 M Na-acetat (pH 4.8) and two washes with 70% ethanol the religated DNA was resuspended in 200 microliters EB. One to three microliters of this religated genomic DNA were used for I-PCR.

RNA Preparation

*Physcomitrella patens* total RNA was prepared by grinding tissue under liquid nitrogen and by the usage of E.Z.N.A. Plant RNA Kit (PeqLab) or RNeasy Plant Mini Kit (Qiagen, Hilden, Germany) following the suppliers manuals. Total RNAs were gel analysed, quantified (OD260), and stored at –20° C. or –80° C., respectively.

DNase Treatment and First Strand cDNA Synthesis 1 microgram of total RNAs was DNase (GIBCO BRL) digested in a total volume of 11 microliters, following the suppliers manual. 4.5 microliters of this DNase treated total RNA (~400 ng) was used with Oligo dT(12-18) primers and SUPERSCRIPT II RNase H Reverse Transcriptase (GIBCO BRL) to prepare first strand cDNA, following the suppliers manual. The resulting cDNA was 10 times diluted with sterile dd$H_2O$ and stored at –20° C.

PCR in General

If not indicated in particular PCRs were done with Advantage cDNA Polymerase Mix (BD Biosciences Clontech, Heidelberg, Germany). For all other PCR-approaches the following DNA polymerases were used: Taq recombinant polymerase (MBI Fermentas, St. Leon-Rot, Germany), Pfu native polymerase (MBI Fermentas, St. Leon-Rot, Germany), Platinum Pfx DNA polymerase (Invitrogen, Karlsruhe, Germany) or TripleMaster PCR System (Eppendorf, Hamburg, Germany). Licenced Thermo-cyclers were Mastercycler gradient (Eppendorf, Hamburg, Germany). All primers were synthesised by MWG Biotech AG, Ebersberg, Germany. For PCR product purification or gel elution GFX PCR DNA and Gel Band Purification Kit (Amersham Bioscience, Freiburg, Germany) was used, following the suppliers manual.

Construction and Cloning of Recombinant Plasmids

Conventional molecular biology protocols were essentially as described by Sambrook et al. (1989), Molecular Cloning: A Laboratory Manual, 2nd edn. Cold Spring Harbor, N.Y.: Cold Spring Harbor Laboratory Press.

Inverse PCR (I-PCR) & Nested PCR

I-PCR was done with 0.25 microliters Advantage cDNA Polymerase Mix and buffer (including 3.5 mM $Mg(OAc)_2$, both BD Biosciences Clontech, Heidelberg, Germany), 0.2 mM each primer, 0.2 mM dNTPs and one to three microliters of genomic religations (see above) in a total volume of 25 microliters. Cycling conditions were: an initial step of 2 minutes at 96° C., then 20 seconds 96° C., 10 seconds initially 67° C. (touchdown: –0.15° C./cycle) and 10 minutes 68° C. as a second step, with 35 to 40 repetitions, followed by a terminal step of 20 minutes at 68° C. and cooling to 4° C. at the end of the program. PCR products were eluted from agarose gels. Elution was done in 30 microliters. Eluted PCR products were either cloned directly in TOPO TA vectors (pCR4-TOPO, Invitrogen, Karlsruhe, Germany) or used as template for reconfirmation in nested PCRs. In the latter case gel eluted, nested PCR products were cloned in TOPO TA vectors (pCR4-TOPO, Invitrogen, Karlsruhe, Germany). Cycling conditions for nested PCRs were: an initial step of 1 minutes at 96° C., then 20 seconds 94° C., 10 seconds 56° C. and 4 minutes 68° C. as a second step, with 25 repetitions, followed by a terminal step of 10 minutes at 68° C.

Generation of pRT101new for Cloning of Amplified Promoter Fragments pRT101p21 (Gorr 1999) was reamplified with Pfu native polymerase (MBI Fermentas, St. Leon-Rot, Germany) using primer 320 and 321 (for this and all subsequent primers see Table 1). Primer 320 (forward) starts at the 2nd codon (5'-(atg)aac . . . ) of the VEGF signal peptide. Primer 321 (reverse) starts in the middle of the HincII site within the multiple cloning site in front of the 35S promoter (5'-gac . . . ). An additional XhoI site was introduced with primer 321. Religation of the PCR product resulted in loss of the 35S promoter and the reconstitution of a HincII site. The sequence of the VEGF gene was verified by sequencing. This new vector was called pRT101new and used for cloning of expression promoting regions via the XhoI or HincII site, respectively, in front of the reporter gene.

Sequencing

All sequencing reactions were performed by SEQLAB Sequence Laboratories, Göttingen, Germany Software Sci Ed Central, Clone Manager Suite were used for primer design, pairwise and multiple sequence alignments. Lasergene, DNASTAR (Version 5) Megalign and SeqMan was used for analysing sequencing data. Homology searches were carried out by BLAST 2 (Altschul et al., 1997).

EXAMPLES

The present invention is illustrated by four examples for moss expression promoting regions: first, the isolation and analysis of various members of a family of tubulin expression promoting regions of Physcomitrella patens. In the second example expression promoting regions for the actin gene family from a variety of different mosses are provided. The third and fourth example deals with ubiquitin expression promoting regions and with RBCS expression promoting regions.

Example 1

Cloning and Analysis of Physcomitrella patens β-Tubulin Genes and their Expression Promoting Regions Overview In order to get β-tubulin (tub) regulatory/promoter sequences from Physcomitrella patens (Pp) in a first step coding sequences of β-tubulin homologues were isolated by polymerase chain reaction (PCR). Therefor an alignment of all nine published β-tubulin genomic sequences from Arabidopsis thaliana (Attub 1-9) were used to design primers within highly conserved coding regions (8F, 9F and 10R; for this and all subsequent primers see Table 1). In addition, sequence information of public EST data from Physcomitrella patens were used, but only three did show homologies to β-tubulins. One of which was used to design a gene-specific primer (F7) upstream of the predicted coding region. Sequence comparison of all cloned PCR products, generated with the primers mentioned and EST data lead to 3 groups of clones with identical DNA within but differences between groups, mainly, but not exclusively, due to differences within introns. This β-tubulin orthologues were named Pptub 1, Pptub 2 and Pptub 3, respectively.

Furthermore, since during the running project, more EST data were available (more than 50000 new entries in NCBI/dbEST with beginning of 2002), a detailed analysis of all 121 Physcomitrella patens ESTs with high similarity to β-tubulin lead to three additional new upstream and three downstream groups of ESTs, being identical within a group but neither identical to any other group nor to Pptub 1-3. PCR with primers derived from predicted noncoding upstream and downstream regions (see below) from each new group and permuting all primer combinations helped to correlate corresponding upstream and downstream groups to a particular locus, named Pptub 4, Pptub 5 and Pptub 6, respectively. Both, genomic and cDNA amplificates of all three new loci were cloned and sequenced, raising the number of β-tubulin orthologues in Physcomitrella patens to six.

Pptub 1 to 4 (in contrast to Pptub 5 and 6) are much more frequently represented in EST databases. Corresponding cDNA libraries were produced using RNA mainly from protonema and young gametophore. So, for this four genes only, based on the gained sequence data, an inverse PCR approach (I-PCR) was performed in order to walk into flanking genomic regions.

Pptub 1

As already mentioned in a first step, Taq (MBI Fermentas, St. Leon-Rot, Germany) PCR fragments from two independent PCRs on Physcomitrella patens genomic DNA using primers 8F and 10R were cloned. One clone (2-1) and two clones (8-1, 8-2), respectively, from each PCR were sequenced partially and turned out to be identical. The corresponding locus was named Pptub 1.

This preliminary sequence information was used to design primers in order to perform a genomic walk into flanking regions of Pptub 1, using an I-PCR approach on religated EcoR I and Hind III genomic digests (primers 35, 36). Reconfirmation of products was done by nested PCR (primers 40, 38). Two clones generated by nested PCR products (E#1 and H 1.7) were sequenced completely.

The Hind III clone H 1.7 did not harbour an internal Hind III site, most likely due to star activity of the enzyme or ligation of a random ds breakage. However, sequences upstream of the first EcoR I site were confirmed by two independent PCRs on genomic DNA (primers 113, 67 and 113, 90). In addition, an additional cDNA (89, 91; Pfu native (MBI Fermentas, St. Leon-Rot, Germany)) PCR product was cloned.

All mentioned clones helped to generate and reconfirm sequence data. In total ~1500 bp upstream of the startcodon and ~1500 bp downstream of the stopcodon were gained.

Pptub 2

As already described above sequence information of published ESTs from Physcomitrella patens was used to design a gene-specific primer (F7) upstream of the predicted coding region. PCR on Physcomitrella patens genomic DNA (primers F7, 10R) and subsequent cloning and sequencing of the PCR product proofed that it, together with all three so far published Pptub ESTs (Pptub EST 1-3) belong to one locus, named Pptub 2. Intron positions could be verified by comparing EST with genomic sequences. This preliminary sequence information was used to design gene-specific primers within introns (primers 95 and 71) in order to perform a genomic walk into adjacent genomic regions of Pptub 2, using an I-PCR approach on religated Pag I, BamH I and Nde I genomic digests. PCR products were reconfirmed by nested PCR (primers 38, 35). Two clones generated by nested PCR products (C#2 Pag and D#2Nde) were sequenced completely. The Nde I clone D#2 did not harbour an internal Nde I site, most likely due to star activity of the enzyme or ligation of a random ds breakage. However, sequence data were confirmed by C#2 Pag and a third I-PCR clone (95#8BamHI; primer 149 and 71). In addition two independent PCRs on genomic DNA (primers 205, 149; Taq (MBI Fermentas, St. Leon-Rot, Germany) and primers 205, 206) confirmed product length. The 205-206 PCR product and an additional genomic downstream PCR product (primers 71, 206; Pfu native (MBI Fermentas, St. Leon-Rot, Germany)) were cloned and helped to verify sequence data.

All mentioned clones helped to generate and reconfirm sequence data. In total ~1400 bp upstream of the startcodon and ~1400 bp downstream of the stopcodon were gained.

Pptub 3

As already mentioned in a first step, Taq (MBI Fermentas, St. Leon-Rot, Germany) PCR fragments from two independent PCRs on *Physcomitrella patens* genomic and cDNA using primers 9F and 10R were cloned. Clones from each PCR (#3-3 genomic, #4-3 cDNA) were sequenced partially and turned out to be identical. The corresponding locus was named Pptub 3.

This preliminary sequence information was used to design gene-specific primers within introns (primers 69, 70) in order to perform a genomic walk into adjacent regions of Pptub 3, using an I-PCR approach on religated Pag I and Nco I genomic digests. Reconfirmation of PCR products was done by nested PCR (primers 38, 35). Two clones (A#1Nco and #4-1Pag) were sequenced completely. A#1Nco is a clone generated by a nested PCR product (38, 35) whereas #4-1PagI was generated by the original I-PCR product (69, 70). In addition a genomic PCR product (primers 203, 204) was cloned and helped to verify sequence data.

All mentioned clones helped to generate and reconfirm sequence data. In total ~1900 bp upstream of the startcodon and ~1100 bp downstream of the stopcodon were gained.

Pptub 4

As already mentioned, in case of Pptub 4, EST data were used to design gene-specific downstream and upstream primers (297, 299) in order to generate genomic and cDNA clones. Additional genomic clones using native Pfu polymerase (MBI Fermentas, St. Leon-Rot, Germany) helped to verify sequence data.

Primer 297 and 299 were inverted (337, 383) and used to perform a walk into adjacent genomic regions of Pptub 4, using an I-PCR approach on religated Nde I and Nco I genomic digests. Two clones (48#2Nco and A02#3Nde) and additional genomic clones (primers 547 and 374; Advantage cDNA Polymerase Mix (BD Biosciences Clontech, Heidelberg, Germany) and Triple Master (Eppendorf, Hamburg, Germany)) were generated.

All mentioned clones helped to generate and reconfirm sequence data. In total ~2300 bp upstream of the startcodon and ~1100 bp downstream of the stopcodon were gained.

Pptub 5 and 6

As already mentioned, in case of Pptub 5 and 6, EST data were used to design gene-specific downstream and upstream primers (Pptub 5: 298, 300 and Pptub 6: 296, 336) in order to generate genomic and cDNA clones of each gene. In case of Pptub 5, additional genomic clones using native Pfu polymerase (MBI Fermentas, St. Leon-Rot, Germany) helped to verify sequence data.

All mentioned clones helped to generate and reconfirm sequence data. In total 2031 bp genomic sequence for Pptub 5 and 3161 bp genomic sequence for Pptub 6 were gained.

Cloning Strategies

Preliminary Pptub 1 (2-1, 8-1, 8-1; all genomic) and Pptub 3 (3-3 genomic, 4-3 cDNA) clones were generated with Taq recombinant polymerase. PCR products were ligated into TOPO TA vectors (pCR4-TOPO, Invitrogen, Karlsruhe, Germany). PCR conditions were: 2.5 unit Taq recombinant polymerase, enzyme buffer, 3.3 mM $MgCl_2$ (all MBI Fermentas, St. Leon-Rot, Germany), 0.4 mM each primer, 100 nanograms of cDNA or genomic DNA as template in a total volume of 25 microliters. Cycling conditions were: an initial step of 5 minutes at 95° C., then 45 seconds 95° C., 10 seconds 60° C. (primer 8F) or 65° C. (primer 9F) and 1 minute 72° C. as a second step, with 30 to 35 repetitions, followed by a terminal step of 5 minutes at 72° C. and cooling to 4° C. at the end of the program.

All other genomic and cDNA clones were

Pptub 1: 113-67, 113-90, 89-90, 89-91 cDNA

Pptub 2: F7/R10, 205-206, 71-206

Pptub 3: 203-204

Pptub 4: 547-374 (+TrippleMaster), 297-299 cDNA+genomic (+Pfu)

Pptub 5: 298-300 cDNA+genomic (+Pfu)

Pptub 6: 296-336 cDNA+genomic

Underlined clones above were generated with Advantage cDNA Polymerase Mix, using 0.25 microliters enzyme mix, buffer (including 3.5 mM $Mg(OAc)_2$, both BD Biosciences Clontech, Heidelberg, Germany), 0.25 mM each primer, 0.25 mM dNTPs and 10-20 nanograms of template per 20 microliter PCR. Cycling conditions were: an initial step of 2 minutes at 96° C., then 20 seconds 96° C., 10 seconds 60° C. and 2 minutes/kb 68° C. as a second step, with 35 to 40 repetitions, followed by a terminal step of 15 minutes at 68° C. and cooling to 4° C. at the end of the program. PCR products of appropriate length were eluted from agarose gels. Elution was done in 30-50 microliters, depending on amount of amplificate. Eluted PCR products were cloned in TOPO TA vectors (pCR4-TOPO, Invitrogen, Karlsruhe, Germany).

All other clones were generated with Pfu native polymerase, as were the two additional genomic clones 297-299 and 298-300, using 0.3 microliters polymerase (=0.75 units), buffer, 2-4 mM $MgSO_4$ (all MBI Fermentas, St. Leon-Rot, Germany), 0.25 mM each primer, 0.2 mM dNTPs and 10-20 nanograms of template per 20 microliter PCR. Cycling conditions were: an initial step of 2 minutes at 96° C., then 20 seconds 96° C., 10 seconds 60° C. and 2 minutes/kb 72° C. as a second step, with 35 to 40 repetitions, followed by a terminal step of 10 minutes at 72° C. and cooling to 4° C. at the end of the program. PCR products of appropriate length were eluted from agarose gels. Elution was done in 30-50 microliters, depending on amount of amplificate. Eluted PCR products were cloned in pZErO-2 (Invitrogen, Karlsruhe, Germany) linearised with EcoRV.

An additional clone of 547-374 was generated with the TripleMaster PCR System, using 0.25 microliters polymerase mix (=1.25 units), tuning buffer (including 2.5 mM $Mg^{2+}$, both Eppendorf, Hamburg, Germany), 0.2 mM each primer, 0.2 mM dNTPs and 10-20 nanograms of template per 20 microliter PCR. Cycling conditions were: an initial step of 2 minutes at 96° C., then 20 seconds 96° C., 20 seconds 60° C. and 3 minutes 72° C. as a second step, with 40 repetitions, followed by a terminal step of 10 minutes at 72° C. and cooling to 4° C. at the end of the program. PCR products of appropriate length were eluted from agarose gels. Elution was done in 30-50 microliters, depending on amount of amplificate. Eluted PCR products were cloned in TOPO TA vectors (pCR4-TOPO, Invitrogen, Karlsruhe, Germany).

In summary, PCR on genomic DNA of *Physcomitrella patens* and cloning of PCR products lead to sequence information of six transcribed *Physcomitrella patens* β-tubulin genes. Additionally, EST and cDNA data were used to confirm genomic sequence data and intron/exon borders. In case of Pptub 1 to 4 inverse PCR lead to non transcribed flanking 5' and 3' genomic sequences. A general overview of all six genomic regions is given in FIG. 1.

Gene Structure & Conservation

As already stressed, Pptub 1 to 4 are most abundantly represented in EST databases. In addition the great majority of their corresponding ESTs were raised from full length cDNA libraries. This two facts helped to determine the transcriptional start site (TSS) of Pptub 1 to 4 in silico. A multiple alignment of 5' ESTs against corresponding upstream genomic regions showed that Pptub 1 to 3 do have a precise transcriptional initiation: 20 out of 27 5' ESTs for Pptub 1, 16 out of 20 5' ESTs for Pptub 2 and 9 out of 14 5' ESTs for Pptub 3, do start at the same, most upstream position, marked with +1 (FIG. 3-6). In addition all three TSSs are surrounded by a consensus sequence (see below). In case of Pptub 4 the 23 5' ESTs indicate multiple TSSs within 100 bp. The start site of the most upstream 5' EST was defined as +1.

An analogous multiple alignment of 3' ESTs against corresponding downstream genomic regions reconfirmed that plant genes almost always come with more than one poly(A) site and that consensus sequences are much less sharply defined than in e.g. mammalian genes, in which the sequence AAUAAA is nearly ubiquitous (for review see: Rothnie et al., 1996).

The six cloned loci of *Physcomitrella patens* did not show any nonsense stop-codons and proper proteins with high similarities to known β-tubulins could be predicted. Outside the coding regions generally, the similarity drops immediately and significantly. Concerning 5' putative regulatory elements, a detailed comparison of all four upstream regions revealed no overall conservation within the gene family or to 5' regions of other known plant β-tubulin genes. However, some interesting matches of conservation within the gene family could be detected:

a) The determined TSSs of Pptub 1 to 3 in all three cases fall within the consensus sequence T/C C A(+1) G/C T G T G C and are embedded in C/T-rich regions (compare consensus of 171 unrelated TATA plant promoters: T/C C A(+1) N M N in plantProm Database available on the world wide web at mendel.cs.rhul.ac.uk/mendel.php?topic=plantprom).

b) 22-24 bp upstream of the TSS—which is within the typical distance for plant TATA promoters (see plantprom DB)—a weak 8 bp TATA box embedded in a conserved stretch of 20-25 bp can be found in Pptub 1 to 3. The TATA box consensus from 171 unrelated plant promoters is: $T_{96}$ $A_{95}$ $T_{96}$ $A_{100}$ $A_{62}/T_{38}$ $A_{97}$ $T_{61}/A_{38}$ $A_{73}$ (see plantProm DB) and for Pptub 1-3 is: T t T A T c T c/t/A, with capitals indicating correlation to consensus.

c) all four genes do have a very low degree of Adenosine (9-16%) in their 5'UTRs.

d) The 5' UTR of Pptub 4 has an overall C/T content of 74%, which—in addition—harbours a C/T stretch (~50 bp), directly behind the start point of the shortest, most downstream 5' EST.

e) Pptub 2 harbours a 40 bp polyA stretch around 450 bp upstream of the TSS (−450 until −489).

f) In Pptub 1 and 4 upstream of app. position −420 long very A/T-rich regions begin (Pptub 1 over 80% A/T for nearly 900 bp and Pptub 4 75% A/T for 1750 bp, rendering open the possibility for the location scaffold/matrix attached regions (S/MARs; (Liebich et al., 2002) upstream of this genes.

Functional Characterization & Quantification of β-Tubulin Promoters

Definition of minimal promoter-fragments giving a maximum of promoter activity was done by functional quantification of putative 5' regulatory sequences of Pptub 1 to 4 in a transient expression system, using nonregenerating *Physcomitrella patens* protoplasts as expression system. For each promoter several constructs of different lengths including upstream regions and 5' UTRs, were brought precisely in front of the startcodon of the reporter gene. As reporter gene a human protein (recombinant human vascular endothelial growth factor 121: rhVEGF121; Gorr 1999) was secreted into the medium via its own signal peptide. The amount of rhVEGF121 in the supernatant of the moss culture was quantified by an ELISA and reflected the strength of the promoter or promoter fragment in the system. Values were related to values obtained by the 35S promoter. Each construct was transformed a minimum of six times in two to three different transformation experiments. Samples were taken after 24 and 48 hours, respectively, with 48 hour samples measured twice in appropriate dilutions in an ELISA. An overview of the results is given in FIG. 2.

The expression promoting regions of Pptub 1 to 4 are disclosed as Seq. ID. Nos. 1 to 8.

Cloning of Amplified Promoter Fragments of Pptub 1 and 4 into pRT101new

Pptub 1:
    1-0 (primer 364XhoI, 363cat)
    1-1 (primer 219XhoI, 363cat)
    1-3 (primer 549XhoI, 363cat)
    1-4 (primer 226XhoI, 363cat)
    1-5 (primer 550XhoI, 363cat)

Pptub 2:
    2-0 (primer 291, 225cat)

Pptub 3:
    3-0 (primer 292, 223cat)

Pptub 4:
    4-0 (primer 373XhoI, 374cat)
    4-1 (primer 548XhoI, 374cat)

The promoter fragments given above were amplified with Pfu native polymerase (MBI Fermentas, St. Leon-Rot, Germany) on genomic DNA using reverse primers starting with the reverse complement sequence of the ATG start codon (cat . . . ) and, in part, forward primers containing XhoI sites. PCR products were cut XhoI and ligated into XhoI/HincII or not cut at all and ligated into HincII opened pRT101new, respectively. Generated clones were verified by sequencing. Clone 1-2 (XhoI/EcoRI), 2-1 (BglII), 2-2 (SalI), 2-3 (EcoRI/SalI), 2-4 (EcoRI/SalI), 3-2 (SalI), 3-3 (Eco147I/HincII), 3-4 (XhoI/SalI) were generated by internal deletions of longer clones. The remaining vectors were gel-eluted and religated. In case single strand overhangs did not fit, ligation was performed after filling-in of recessed 3'-termini with Klenow Fragment (MBI Fermentas, St. Leon-Rot, Germany), following the suppliers manual.

Pptub 1

Six different promoter lengths were cloned into the transformation vector pRT101p21 in front of the reporter gene. The data of all constructs are given in FIG. 3. (5' UTR=+1 (TSS) until +226, +227=ATG)

1-0 −1307 bp (1533 bp 5' region of Pptub 1)

1-1 −985 bp (1211 bp 5' region of Pptub 1)

1-2 −416 bp (642 bp 5' region of Pptub 1)

1-3 −248 bp (474 bp 5' region of Pptub 1)

1-4 −83 bp (309 bp 5' region of Pptub 1)

1-5 −71 bp (297 bp 5' region of Pptub 1)

Promoter fragment 1-2 can be defined as the shortest promoter fragment giving high expression rates. The rates are app. 150% compared to values generated with the 35S promoter, which was set to 100%. Note that upstream of the minimal promoter fragment 1-2 a long, very A/T rich region starts (over 80% A/T for nearly 900 bp).

Pptub 2

Five different promoter lengths were cloned into the transformation vector pRT101p21 in front of the reporter gene. The data of all constructs are given in FIG. 4. (5' UTR=+1 (TSS) until +122, +123=ATG)

2-0 −1075 bp (1197 bp 5' region of Pptub 2)

2-1 −676 bp (798 bp 5' region of Pptub 2)

2-2 −425 bp (547 bp 5' region of Pptub 2)

2-3 −245 bp (367 bp 5' region of Pptub 2)

2-4 −67 bp (189 bp 5' region of Pptub 2)

Promoter fragment 2-2 can be defined as the shortest promoter fragment giving high expression rates. The rates are comparable to values generated with the 35S promoter (100%).

Pptub 3

Different promoter lengths were cloned into the transformation vector pRT101p21 in front of the reporter gene. The data of four constructs are given in FIG. 5. (5' UTR=+1 (TSS) until +112, +113=ATG)

3-0 −1274 bp (1386 bp 5' region of Pptub 3)

3-2 −765 bp (879 bp 5' region of Pptub 3)

3-3 −272 bp (384 bp 5' region of Pptub 3)

3-4 +52 bp (60 bp 5' UTR of Pptub 3)

Promoter fragment 3-2 can be defined as the shortest promoter fragment giving high expression rates. The rates are app. 300% compared to values generated with the 35S promoter, which was set to 100%.

Pptub 4

Two different promoter lengths were cloned into the transformation vector pRT101p21 in front of the reporter gene. The data are given in FIG. 6.

(5' UTR=TSSs (+1 until +103) until +205, +206=ATG)

4-0 −419 bp (624 bp 5' region of Pptub 4)

4-1 −1 bp (206 bp 5' region of Pptub 4)

Promoter fragment 4-1 gives expression rates that are app. 250% compared to values generated with the 35S promoter, which was set to 100%. Note that upstream of this minimal promoter fragment (4-0) a long, very A/T rich region starts (75% A/T for 1750 bp).

In summary transient promoter activity of Pptub 1 to 4 genomic upstream regions were characterised. Minimal promoter fragments showing a maximum of promoter activity were defined and gave yields of up to 3 times the 35S promoter activity.

Pptub-Constructs Summary (See Also: Sequence Listing)

Pptub1 Upstream

−1533 until −1 (+1=start codon)

−1533 until −644=81% AT

−1533 VEGF 1-0 (primer 364)

−1211 VEGF 1-1 (primer 219)

−642 VEGF 1-2 (EcoRI/XhoI)

−474 VEGF 1-3 (primer 549)

−309 VEGF 1-4 (primer 226)

−297 VEGF 1-5 (primer 550; without putative TATA box: −304 until −295)

−226 TSS (start of 5'UTR)

Pptub1 Downstream 1 until 1539 (1=directly behind stop codon)

332 end of longest EST (3'UTR)

1539 start of primer 90

Pptub2 Upstream

−1197 until −1 (+1=start codon)

−1197 VEGF 2-0 (primer 291)

−798 VEGF 2-1 (BglII)

−547 VEGF 2-2 (SalI)

−450 until −489=poly A stretch

−367 VEGF 2-3 (EcoRI/SalI)

−189 VEGF 2-4 (XhoI/SalI)

−122 TSS (start of 5'UTR)

Pptub2 Downstream 1 until 1012 (1=directly behind stop codon)

297 end of longest EST (3'UTR)

1012 start of primer 206

Pptub3 Upstream

−1386 until −1 (+1=start codon)

−1386 VEGF 3-0 (primer 292)

−879 VEGF 3-2 (SalI)

−384 VEGF 3-3 (Eco147I/HincII)

−112 TSS (start of 5'UTR)

−60 VEGF 2-4 (XhoI/SalI)

Pptub3 Downstream 1 until 997 (1=directly behind stop codon)

203 end of longest EST (3'UTR)

1012 start of primer 204

Pptub4 Upstream

−624 until −1 (+1=start codon)

−624 VEGF 4-1 (primer 373)

−206 VEGF 4-2 (primer 548)

−205 until −103 area of TSS (start of 5'UTR)

−55 until −93 CT stretch

Pptub4 Downstream 1 until 1146 (1=directly behind stop codon)

466 end of longest EST (3'UTR)

1141 until 1164 NcoI

Example 2

Cloning and Analysis of Actin Genes from Different Moss Species and their Expression Promoting Regions 2.1. Genomic Structure of *Physcomitrella patens* Actin Genes.

Four actin genes and promoter regions of the moss *Physcomitrella patens* and three from *Funaria hygrometrica* and the liverwort *Marchantia polymorpha* have been isolated in order to construct expression vectors for their use in moss.

Using specific oligos designed from *Physcomitrella* EST sequences that are present in the public databases, four actin genes (Ppact1, Ppact3, Ppact5 and Ppact7) were isolated in several rounds of iPCR from genomic DNA and sequenced.

In *Physcomitrella* the structure of the isolated genes resembles in one case (Ppact1) the conserved structural organisation of actin genes of higher plants. The un-translated leader is disrupted by a relatively long (955 bp) intron located 14 nt upstream the initiator ATG. The coding region presents three smaller introns which are situated at the same positions as the introns of actin genes of other plant species. The first one is located between codons 20 (lys) and 21 (ala), the second is splitting codon 152 (gly) and the third is between codon 356 (gln) and 357 (met). This general structure appear to be different for the three other *Physcomitrella* actin genes isolated (Ppact3, Ppact5, and Ppact7). In those cases the 5'UTR intron (434 bp, 1006 bp and 1055 bp respectively) is also located 14 nt before the ATG but the coding region is disrupted only by one intron positioned between codons 21 (lys) and 22 (ala) (FIG. 7).

2.2. Activity Studies of the Expression Promoting Regions of Actin Genes.

To study the activity of the different *Physcomitrella* actin expression promoting regions (Seq. ID Nos. 5 to 8) as well as the effect of the 5'UTR of the different genes, different vectors were designed for expression of the hVEGF protein under the control of the 5' regions under study.

Around 2 kb genomic regions upstream the transcription initiation site were isolated by iPCR from genomic DNA and sequenced, and vectors containing the cDNA of the human VEGF driven by the promoters and containing the exact leader sequences including the 5'intron were constructed for transient transfection of moss protoplasts. The complete 5'promoting expression regions were amplified by proof reading PCR using primer 395 and 332 for Ppact1, 408 and 333 for Ppact3, 511 and 334 for Ppact5, and 413 and 335 for Ppact7.

Transformation of protoplasts was performed using the same number of molecules for each construct to be tested and in parallel to a construct carrying the hVEGF cDNA under the control of the CaMV 35S promoter. The hVEGF protein contains at the N-terminal part a 26 aa signal peptide that permits secretion of the recombinant protein to the medium. Analysis of the transformations was carried out by ELISA, taking different dilutions of the medium where the protoplasts were incubated 48 hours after transformation.

The capacity to drive expression of the different *Physcomitrella* 5' actin regions was compared to the activity of the constitutive 35S promoter.

In all cases analysed, the 5'regions of the actin genes were reaching higher activity than the 35S promoter. However the level of expression varied for the different actin regulatory sequences. Thus, the 5'sequence of Ppact3 was only promoting around a 2 fold higher expression of VEGF than the 35S promoter. Higher levels of VEGF were measured when vectors containing the 5'regions of Ppact1 and Ppact7 were used for transformation. In those cases values between 4 and 8 folds the 35S values were obtained. Nevertheless the most dramatic differences were observed in the case of the 5'Ppact5 gene, where up to 11 fold higher expression values compared to the 35S were in some cases obtained (FIG. 8).

To further investigate on the role of the 5' UTR region of the high activity *Physcomitrella* actin genes, vectors containing deletions, combinations and substitutions of the 5'UTR intron were made and used for transient assays in moss protoplasts.

Deletion of the Ppact1 5'intron dramatically decreased the levels of transient expression in comparison to those obtained when the intact 5'region of Ppact1 was used. In this case the amount of secreted VEGF protein that could be detected in the protoplasts medium was very similar to the obtained by the CaMV 35S promoter. This would indicate that the 5'intron of the Ppact1 is essential for efficient gene expression from the Ppact1 promoter. Same results were obtained when the 5'UTR including the leader intron was fused downstream the 35S promoter. This construct yielded the same amount of secreted protein as the intact 35S promoter indicating that the 5'UTR region is not having any dramatic influence on the activity of promoters other than the Ppact1 promoter. It is important to indicate that a construct carrying just the 5'UTR Ppact1 region was able to promote protein production only in a 30% lower amount than the 35S promoter alone. This could suggest a small promoter activity in this region of the gene, or a rest of promoter activity present in the backbone sequence of the vector (FIG. 9).

The same approach was used to investigate the influence on the promoter activities of the 5'UTR introns contained in the Ppact5 and Ppact7 genes. Constructs in which the 5' intron was deleted were analysed and similar results as in the case of Ppact1 were obtained, ie. the amount of protein reached was approximately the same as with the 35S promoter in the case of Ppact5 and slightly lower in the case of Ppact7, indicating that the presence of the intron in the 5'UTR is essential for the efficient activity of the promoters. Again some residual promoting activity was observed when the transformation was performed with constructs containing only the 5'transcribed region up to the ATG. Furthermore, in the case of these two genes, the fusion of the 5'UTR downstream the 35S promoter yielded higher rates (2 to 7 folds) of expression of the VEGF protein when compared to the 35S promoter alone (FIGS. 10, 11). Similar results were observed in the case of Ppact3, where the 5'UTR alone or fused downstream the CaMV 35S, yielded around 2 and 3 folds respectively in comparison to the 35S (FIG. 12). These indications would suggest the presence of enhancer activity in the 5'transcribed regions for these three genes even when they are positioned under a different promoter.

To further investigate the role of the 5'intron present in the Ppact1, Ppact5 and Ppact7 genes, substitutions of the leader intron of the Ppact1 gene with the 5'intron of Ppact5 and Ppact7 were engineered in vectors for transient transformation. In parallel substitutions of the Ppact1 5'intron with the ppact1 introns present in the coding region of the gene, were performed.

Substitutions of the Ppact1 5'intron, by the Ppact 1 coding region introns 1 and 3 resulted in a decrease of the expression levels of around 25%. Still the amount of protein detected was around 2-3 fold higher than the obtained with the CaMV 35S promoter. The substitution of the 5'intron by the intron 2 of the coding region surprisingly resulted in no activity of the promoter (FIG. 13). The construct was however checked, and the sequence showed that the splicing site for the intron was not correct. A new construct carrying the correct splicing sequence was made and the results after moss transformation indicated that the effect of the intron 2 is the same as for the other substitutions.

A reduction of protein expression was also observed when the substitution was done with the 5'introns corresponding to the Ppact5 and Ppact7 genes, but in this case the reduction was slightly smaller.

2.3. Deletion Constructs of the Expression Promoting Regions of Actin Genes.

A further characterisation of the different actin genes promoters was carried out by making deletion constructs of the 5'untranscribed regions and analysing them through transient transformation of moss protoplasts.

Thus for the Ppact1 constructs carrying different genomic region lengths (−1823 bp, −992 bp, −790 bp, −569 bp, −383 bp, −237 bp, and −82 bp) upstream the initiation of transcription (+1) were made. In principle all the constructs except the −82 bp, could have full promoter activity. However the −383 bp construct shows a reduction of activity and reaches similar levels as the −82 bp construct (FIG. 14).

Analysis of deletion constructs of the promoter region of Ppact3 revealed some interesting features. As it was described, this promoter presented a lower activity compared to the other actin genes promoters, although in relation to the CaMV 35S, it was slightly more active. In this case the following 5'untranscribed regions were tested: −2210 bp, −995 bp, −821 bp, −523 bp, −323 bp, −182 bp and −81 bp. Surprisingly the activity of the promoter was approximately the same as the CaMV 35S for the constructs containing up to −821 bp of the promoter region. However the constructs containing from bp −523 and shorter regions towards the transcription start, yielded two folds more amount of recombinant protein. This could indicate cis-acting regions located upstream the −523 bp region that down regulate the transcription of this gene during the transient transformation assay (FIG. 15).

In the case of Ppact5, constructs containing the −1872 bp, −758 bp, −544 bp, −355 bp, and −121 bp fragments upstream the transcription start of the gene were generated. The results obtained from the transient assays indicate that the full activity of the promoter resides in a region between −758 and −121 from the start of transcription (+1) (FIG. 16).

The following deletion constructs for the 5'untranscribed region of Ppact7 were analysed: −1790 bp, −1070 bp, −854 bp, −659 bp, −484 bp, −299 bp, and −66 bp. The results obtained indicate that the region comprised in between −484 bp and −299 bp is essential for the full activity of the promoter during the transient experiment assays. (FIG. 17).

In order to obtain a set of heterologous promoters of the *Physcomitrella* actin genes, other two species, the moss *Funaria hygrometrica* and the liverwort *Marchantia polymorpha*, were used to isolate genomic DNA fragments containing actin genes. To this end, oligos with different degrees of degeneration were designed to perform PCR reactions using as template genomic DNA isolated from the two species.

2.4. Comparison of Different Actin Genes from the Different Moss Species *Physcomitrella patens, Funaria Hygrometrica* and *Marchantia polymorpha*

*Physcomitrella patens*

The four different genomic actin sequences isolated from *Physcomitrella patens* are likely to represent the whole functional sequences of the genes including 5'promoter sequence, 5'UTR+5'intron, ORF+internal introns and the 3'UTR and further 3'downstream sequence. In total for Ppact1 5809 bp, for Ppact3 5633 bp, for Ppact5 8653 bp and for Ppact7 6351 bp of genomic sequence was isolated (FIG. 18 A). The coding regions of the isolated *Physcomitrella* actin cDNAs are almost all 1137 bp in length, except Ppact1 which has an ORF of 1134 bp. The corresponding proteins are 378 amino acids in lengths except Ppact1 which has 377 amino acids. On the nucleotide level the coding sequences share homologies between 86.6 and 98.9%. The protein sequences have an identity between 97.1 and 99.7% (DNA STAR, MegAlign Program, Clustal V (weighted) sequence alignment).

For all four *Physcomitrella* actin genes extended genomic DNA sequences 5' of the ATG Start codon could be isolated by iPCR and sequenced: 2973 nt for Ppact1, 3091 nt for Ppact3, 3095 nt for Ppact5 and 3069 nt for Ppact7. For Ppact1, Ppact5 and Ppact7 5'race by using the Gene Racer Kit (Invitrogen), which allows the amplification of only full length cDNAs, was performed to determine the 5'UTRs of the genes. For Ppact3 the 5'UTR was determined by the length of different ESTs from database. By comparing the cDNAs with the genomic iPCR fragments the presence of large 5'introns could be shown. The lengths of the 5'introns which are all located at position −14 to the ATG Start codon are 955 bp, 434 bp, 1006 bp and 1055 bp for Ppact1, Ppact3, Ppact5 and Ppact7 respectively (FIG. 18 A). The positions of the ORF internal introns was determined by comparing the genomic sequences and the derived protein sequences to the cDNA sequences and protein sequences of the actin genes from *Arabidopsis thaliana*. The 5'promoter sequences for the *Physcomitrella* actin genes available are 1824 nt for Ppact1, 2270 nt for Ppact3, 1909 bp for Ppact5 and 1805 bp for Ppact7 (FIG. 18 A).

In total 4 different actin genes from *Funaria hygrometrica* (expression promoting regions: Seq. ID Nos. 9 to 12) and 3 different genes from *Marchantia polymorpha* (expression promoting regions: Seq. ID Nos. 13 to 15) could be identified by degenerated PCR on genomic DNA. As the aim was predominantly to isolate 5'promoter regions of the putative different actin gene homologs from the different moss species, most of the sequences are incomplete at the 3'end to date (FIG. 18 B/C).

*Funaria hygrometrica*

For *Funaria* the identified actin genes were named Fhact1, Fhact4.4, Fhact5 and Fhact5b. 3951 bp of Fhact1, 2417 bp of Fhact4.4, 4432 bp of Fhact5 and 722 bp of Fhact5b of genomic sequence could be isolated by iPCR for the different actin genes. The complete coding cDNA sequence could be isolated for the Fhact1 gene which has a coding sequence of 1134 nucleotides. For the other *Funaria* actin genes partial sequences are available at the moment, lacking the 3'ends: 906 bp for Fhact4.4, 965 bp for Fhact5 and 722 bp for Fhact5b (FIG. 18 B) The isolated coding sequences share homologies in a range of 87.4 and 99.2% on the nucleotide level. The derived protein sequences are 90.8 to 99.2% identical (DNA STAR, MegAlign Program, Clustal V (weighted) sequence alignment).

Except for Fhact5b, 5'sequences upstream of the ATG Start codon could be isolated by iPCR and sequenced. In the case of Fhact1 1824 bp, for Fhact4.4 1333 bp and for Fhact5 3289 bp are available. The length of the different 5'UTRs were determined by 5'race using the Gene Racer Kit (Invitrogen). The intron-exon structure was determined by comparison of the cDNA sequence with the genomic sequences obtained by iPCR and by comparison to the *Physcomitrella* genes. As in the case of the *Physcomitrella* actin genes the identified *Funaria* actin genes contain large 5'introns located at position −14 of the cDNAs, 928 bp, 1015 bp and 656 bp in length for Fhact1, Fhact4.4 and Fhact5 respectively. By now for Fhact1 700 bp, 145 bp for Fhact4.4 and for Fhact5 2515 bp of 5'promoter sequence was isolated and sequenced. For Fhact1 419 bp of the 3'region was isolated. The 5'regions or 3'regions of the *Funaria* actin genes are amplified by PCR on genomic DNA from *Funaria hygrometrica* by using the primers 908 and 909 for the 5' region of Fhact1, 983 and 984 for the 3' region of Fhact1, 1000 and 1001 for the 5'region of Fhact4.4 and 611 and 612 for the 5'region of Fhact5.

*Marchantia polymorpha*

For *Marchantia* the identified actin genes were named Mpact1, Mpact4 and Mpact15. For all three sequences the 3'ends are lacking. So far for Mpact1 2229 bp, for Mpact4 3987 bp and for Mpact15 2174 bp of genomic sequences were isolated and sequenced. The lengths of the coding cDNA sequences isolated are 997 nt, 962 nt and 995 nt for Mpact1, Mpact4 and Mpact15 respectively. (FIG. 18 C). The sequence homologies within the *Marchantia* actin genes are a little bit lower than compared to the other two moss species, in a range between 78.3 and 85.5% on the nucleotide level and between 94.7 and 96.1% on the amino acid level (DNA STAR, MegAlign Program, Clustal V (weighted) sequence alignment). 5'upstream sequence of the ATG for all the three identified different *Marchantia* actin genes were isolated by iPCR and sequenced: 937 bp for Mpact1, 3025 bp for Mpact4 and 910 bp for Mpact15. The 5'regions of the *Marchantia* actin gene homologous are amplified by PCR on genomic DNA from *Marchantia polymorpha* using the primer 950 and 951 for 5'Mpact1, 960 and 961 for Mpact4 and 970 and 971 for Mpact15. The intron-exon structure of the ORF was obtained by comparing the different actin gene sequences from the different moss species. The isolated 5' sequence of Mpact1 shows the consensus sequence for intron splice sites (aggt) at position −14 indicating the presence of a 5'intron as in the case of the other *Physcomitrella* and *Funaria* genes. Within the 5'upstream sequences of Mpact4 and Mpact15 no intron splice site consensus sequence is present, proposing the lack of 5'introns (FIG. 18 C).

Comparison of *P. patens, F. hygrometrica* and *M. polymorpha* Actin Genes

As mentioned above in general the homologies of nucleotide and protein sequences for the different isolated actin genes within one species is very high especially at the protein level. The homologies between the closely related moss species *Physcomitrella patens* and *Funaria hygrometrica* also appear to be very high. On the nucleotide level the actin genes show homologies between 86.9 and 96.3% identity and on the amino acid level the range of homology is 95.5 to 99.7%.

In contrast to that the more distant relation of the liverwort *Marchantia polymorpha* to the other both species is reflected in the lower homologies of the genes on the nucleotide level. The homologies between *Physcomitrella* and *Marchantia* actin genes is in the range of only 75.2% and 78.8% and between *Funaria* and *Marchantia* the homologies are in the range of 75.5% to 80.4%. On the amino acid level the homologies of the *Marchantia* actin genes vary between 93.0% and 96.1% compared to *Physcomitrella* and between 93.4% and 96.7% compared to *Funaria*.

Intron-Exon Structure (FIG. 18 A/B/C)

As indicated before the intron-exon structure of the *Physcomitrella* actin genes to a certain extent are similar to that of higher plants but also with clear differences. All isolated *Physcomitrella* actin genes contain a large 5'intron in the 5'untranslated region, which almost all of the investigated higher plants actins do. Only Ppact1 contains 3 internal introns within the ORF reflecting the situation for example for all isolated actin genes from *Arabidopsis thaliana*. The ORF internal intron positions of Ppact1 are also conserved compared to higher plant actin genes. On the contrary Ppact3, Ppact5 and Ppact7 contain only one internal intron within the ORF.

The same genomic structure can be found in the isolated *Funaria* actin genes with one extended 5'intron within the 5'UTR. Fhact1 has the same conserved intron-exon structure as Ppact1 whereas Fhact4.4 and Fhact5 contain only one internal intron within the ORF sequence. The isolated sequence of Fhact5b is to short to say something clear about the intron-exon structure but at least it does not contain the internal intron2 compared to Fhact1 or Ppact1.

In *Marchantia* the genomic structures of the isolated actin genes seem to be more different. It is important though, to indicate that the number of different actin genes in the three different moss species is not known and it could be that the three isolated actin genes from *Marchantia* do not represent the individual functionally homologous genes. It is likely that there are more than three actin genes present in *Marchantia* and more than four actin genes in *Physcomitrella* and *Funaria*.

However, the intron-exon structure of Mpact1 seems to be the same as in the case of Ppact1 and Fhact1 with a 5'intron within the 5'UTR and the conserved positions of the ORF internal introns 1 and 2. Mpact15 also contains the conserved ORF internal intron1 and intron2 but it does not have a conserved intron splice site at position −14 within the 5'UTR or at position −10 as found for the *Physcomitrella* or for some *Arabidopsis* actin 5'introns respectively, arguing for a lack of a 5'intron. The same situation is found for Mpact4, probably lacking a 5'intron. In addition Mpact4 also does not have the intron1 or the intron2 within the ORF, which is different from all isolated moss actin genes so far.

Putative Homologous Moss Actin Genes

Although the intron-exon structure of the different isolated actin genes from *Physcomitrella* and *Funaria* might propose conclusions about homologous genes between the two species one can not conclude this from the genomic structure. For example Ppact1 and Fhact1 share the same conserved intron-exon structure but it is not clear, as indicated before, whether there are more genes present in the genome of both plants which might have the same genomic structures. To give a statement on homologous genes also expression data would be required to propose functional homologies. Also from the sequence homologies of the proteins or the coding cDNA sequences it is not possible to make any assumptions about corresponding homologous genes between the species as they are too similar in general.

But in the case of *Physcomitrella* and *Funaria* it was interesting to find also very high sequence homologies within the non coding sequences regarding to the UTR sequences, intron sequences and promoter sequences. Therefore high homologies were found between Ppact1 and Fhact1 and between Ppact3 and Fhact5. In both cases the intron sequences showed unusual high conservation. In the case of Ppact1 and Fhact1 the homologies were as follows: 5'intron: 58%; intron1: 64%, intron2: 52% and intron3: 55%. In the case of Ppact3 and Fhact5 the homologies are for the 5'intron 51% and intron1 shows 48% identity.

For both cases also the isolated 5' promoter sequences show high homologies. FIG. 19 A shows a schematic comparison of the isolated promoter regions of Ppact1 and Fhact1. The transcription start is said to be at position 1, the first nt of the 5'promoter region is said to be −1. The isolated 267 bp of 5'promoter region of Fhact1 show an over all homology to the first 267 bp of the Ppact1 5'promoter region of 58%. Within this sequence there are blocks of different homologies observable. The sequence between −267 and −129 shows a homology of 51%. The following 29 bp show 62% identity and within position −100 and −1 the homology is almost 70%. Concerning these high sequence identities between the Ppact1 and Fhact1 intron and promoter sequences it is reasonable to put these two genes as the homologous genes in these two mosses. Another interesting aspect is the observation of the drop of expression observed between the different Ppact1:vegf deletion constructs (FIG. 15). The dramatic drop of expression appears to be between the −237 and the −82 deletion construct. This argues for an important function of the 5'promoter region between −129 and −1 as here the sequence of the promoter regions of Ppact1 and Fhact1 is highly conserved as just mentioned and the −82 deletion construct does not contain all of the highly conserved sequence but the −237 deletion construct does.

Highly conserved regions within the promoters of Ppact3 and Fhact5 can also be observed. In this case the promoter regions for both genes isolated are much longer. Therefore even more regions of homologies are found between the two 5'promoter regions (FIG. 19 B). In this case the promoter regions of Ppact3 from −1 to −2270 and of Fhact5 from −64 to −2325 show some interesting homology features. The difference in the TS position might be due to the fact that the 5'UTR of Fhact5 was determined experimentally and the one of Ppact3 was determined by analysing ESTs from database.

The sequence of Ppact3 between −2270 and −1876 shows only a 29% low homology to the same sequence area of Fhact5 located between −2325 and −1948. Then an expanded region of about 1100 nt is following showing a very high homology of 82%. The next 140 nt of Ppact3 and 152 nt of Fhact5 promoter show "only" 53% homology. The sequence of Ppact3 located between −641 and −463 shows again high conservation of 76% to the region between −705 and −528 of Fhact5. The following about 180 nt show again lower homology of 53%. The last 288 bp of Ppact3 promoter sequence then are again more homolog with 73% to the next 280 bp of Fhact5. These regions of different degrees of homologies between the two homologous genes might indicate the presence of regulative active elements within the 5'promoter region.

As for the case of Ppact1 and Fhact1 also here the expression analysis of the different Ppact3:vegf deletion constructs are interesting in this context (FIG. 17). Here a significant increase of the vegf expression level of the −2210, −995, −821 deletion constructs compared to the −523 deletion construct was observed. The three deletion construct which contain at least parts of the expanded homolog region between −1876 and −779 found in Ppact3 and Fhact5 reached levels about that of the 35 S promoter whereas the −523 deletion construct showed a 2½ fold increase of expression compared to the 35S promoter or the longer deletion constructs. This might argue for the presence of a negative regulator within this region of 82% homology between Ppact3 and Fhact5.

In the case of Marchantia, no comparable sequence homologies could be found between the different actin genes from Physcomitrella and Funaria.

For the Fhact5 gene a construct containing 1157 bp of the 5'untranscribed region fused to the hVEGF cDNA was made and used for transient transformation experiments on Physcomitrella protoplasts. The amount of protein detected in this case was in the same range but slightly higher (up to 2 folds) as with the CaMV 35S promoter. The Fhact5 gene presents the highest homology to the PpAct3 gene, and interestingly both of the promoters showed a similar activity in Physcomitrella protoplasts during the transient assays.

2.5. Stable Transgenic Lines.

The cassettes containing Ppact1, Ppact5 and Ppact7 5' MEPRs driving the expression of the VEGF cDNA were introduced in the genome of Physcomitrella plants. For each of the MEPRs five to ten stably transformed plants were recovered and tested for the expression of rhVEGF. For these three MEPRs tested, expressed and secreted moss derived rhVEGF was detected in the supernatants of the cultures where the plants were growing (standard Knop medium), indicating that the MEPRs promote protein expression under non-inducing conditions (standard conditions) when they are integrated in other parts of the genome. The amount of protein that could be measured in those lines ranged from 7 ngVEGF/mg moss dry weight until 53 ngVEGF/mg moss dry weight, depending on the construct and the stable line.

One transgenic moss strain containing VEGF cDNA under control of Ppact5 was used to perform bioreactor cultures. The amount of moss derived recombinant VEGF in the supernatant of bioreactor cultures measured by ELISA was 40-50 ngVEGF/mg moss dry weight.

Example 3

Cloning and Analysis of *Physcomitrella patens* and *Funaria hygrometrica* Ubiquitin Genes and their Expression Promoting Regions Taking advantage of the presence of several EST sequences corresponding to polyubiquitin genes of Physcomitrella, specific oligos were designed to isolate the corresponding genomic sequences of the most abundantly present EST of the ubiquitin gene homologous sequence in the databases, named Ppubq1. 2146 bp of 5'region of Ppubq1 could be identified by iPCR. A 129 bp transcribed 5'leader is present before the ORF starts, determined by 5'race. The 5'region of Ppubq1 is amplified by PCR on genomic DNA from Physcomitrella patens using the primers 777 and 602.

Vectors carrying different parts of promoter and 5'UTR region driving expression of the hVEGF cDNA, were constructed to analyse the activity of the promoter during transient transformation of Physcomitrella protoplasts.

The results indicated a similar activity for this promoter to the Ppact5 promoter (or even higher). The constructs tested, 1.6 Kb and 1.3 Kb promoter fragments, reached expression levels around 4 times and almost 7 times higher than the CaMV 35S.

The ubiquitin gene from Funaria, Fhubq1, was identified by performing a 5' race PCR on Funaria total RNA with a primer derived from the Ppubq1 coding sequence. The isolated 5'UTR sequence and partial coding sequence was used to design primers for iPCR on genomic ligations of Funaria hygrometrica. This way 5' upstream sequence of the 5'UTR was identified. The 5'region is amplified by PCR on genomic DNA from Funaria hygrometrica using the primers 943 and 944.

Example 4

Cloning and Analysis of *Physcomitrella patens* RBCS Expression Promoting Regions As putative candidates next to the actin, tubulin and ubiquitin genes the ribulose-1,5-bisphosphate carboxylase/oxygenase small subunit (rbcS) genes were taken into consideration. The different rbcS genes are encoded on the nuclear genome. The rbcS genes are members of a gene family. The rbcS genes are expressed basically in all green parts of plants able to fixate $CO_2$. Therefore this gene family is of interest to get 5' and 3' flanking expression promoting regions of different rbcS genes from different mosses. As a first step *Physcomitrella* EST databases were analysed. It was found that the rbcS genes from *Physcomitrella patens* are organised in a gene family, consisting of 12 genes. The most abundantly present ESTs of the rbcS genes, named PprbcS12, was taken as a candidate to find it's 5' and 3' expression promoting sequences. Starting with the EST sequence data, 5' and 3' flanking regions of this gene was identified by iPCR and the cloned 5' and 3' regions were sequenced. The 5'region is amplified by PCR on genomic DNA from *Physcomitrella patens* using the primers 839 and 858. The 3'region is amplified by PCR using the primers 904 and 901.

In the enclosed Sequence Listing, the following sequences are given (Seq. ID. No/name of sequence/5' or 3' region relative to the protein encoding region):

1 Pptub1 5'
2 Pptub1 3'
3 Pptub2 5'
4 Pptub2 3'
5 Pptub3 5'
6 Pptub3 3'
7 Pptub4 5'
8 Pptub4 3'
9 Ppact1 5'
10 Ppact1 3'
11 Ppact3 5'
12 Ppact3 3'
13 Ppact5 5'
14 Ppact5 3'
15 Ppact7 5'
16 Ppact7 3'
17 Fhact1 5'
18 Fhact1 3'
19 Fhact4.4 5'
20 Fhact5 5'
21 Mpact1 5'
22 Mpact4 5'
23 Mpact15 5'
24 Ppubq1 5'
25 Fhubq1 5'
26 PprbcS12 5'
27 PprbcS12 3'

TABLE 1

List of Primers

| Primer No. | SEQUENCE (5'-3') | SEQ ID NO. |
|---|---|---|
| 35 | atccaggagatgttcaggcg | 28 |
| 36 | ccgmacgctgtccatrgtycc | 29 |
| 38 | acattgatgcgctccarctgc | 30 |
| 40 | ggbatggacgagatggagttcac | 31 |
| 67 | agcacatgcacacccaatacgcttgtcgcaattc | 32 |
| 69 | gtcgtcatagacgacaagaccggggatccacagc | 33 |
| 70 | tcagtgctgtccgtgaatctctctctctgcttg | 34 |
| 71 | ctgtgttcggattagactccccgtagcctttgtg | 35 |
| 89 | tcgattggcgagttgcaaggagggcaagg | 36 |
| 90 | tgcctgctcatcttgagtatggcgtgttg | 37 |
| 91 | ctgcaagcaatgcgcactgaaacaagatgg | 38 |
| 95 | gacctggaaacctgcacaatcacgcataga | 39 |
| 113 | tagcataagataaagatgttctctacc | 40 |
| 149 | ctcaccagccaatggctatgc | 41 |
| 203 | ccgtgggacttagttgtcttcacttc | 42 |
| 204 | gatcgaaattgctgcttggcctccac | 43 |
| 205 | tcgaggatgtgtccttagtcgagaa | 44 |
| 206 | aacttcacgcattccacaagccacac | 45 |
| 219 | ttgatactcgagaagtccaaaataatttaatgatac | 46 |
| 223 | catcttcgctaaggatgatctacaacgag | 47 |
| 225 | catcttcagtgtgctctacctcacg | 48 |
| 226 | ctactcgagcacatataatactgccctagtgcc | 49 |
| 291 | gacagatctccttagtcgagaaggcgcgggacgtg | 50 |
| 292 | gacccgtgggacttagttgtcttcacttc | 51 |
| 296 | gctgctcttctcgtgattgtct | 52 |
| 297 | cattcccacccttccttctcttc | 53 |
| 298 | gttttctggctcttccttgg | 54 |
| 299 | atcgttctcgactcttcttcc | 55 |
| 300 | gttacgctcgcaatgcgtact | 56 |
| 320 | aactttctgctgtcttgggtgcattg | 57 |
| 321 | gacctgcaggcactcgagcttgtaatcatggtcatag | 58 |
| 332 | catttcttaataccgacctgcccaacca | 59 |
| 333 | catggagaagaaatacttgcacatcaaaag | 60 |
| 334 | cattatttaatacggacctgcacaacaac | 61 |
| 335 | cattttttagaatgatcctacaggagttc | 62 |
| 336 | agtctggcaagttcccttcg | 63 |
| 337 | gaagagaaggaagggtgggaatg | 64 |

TABLE 1-continued

List of Primers

| Primer No. | SEQUENCE (5'-3') | SEQ ID NO. |
|---|---|---|
| 338 | ggaagaagagtcgagaagcgat | 65 |
| 363 | catcttgtccaactaccgcgacccgaaccc | 66 |
| 364 | aatctcgagtagcataagataaagatgttctctacc | 67 |
| 373 | ggtaaagctctcgagtgcagtagacgacaaaatg | 68 |
| 374 | catcttgctcaagctgtgcgaagctc | 69 |
| 395 | atctcgaggatccattcaacggaggataagt | 70 |
| 408 | caactcgagatcggtctgtaagccctgtatttg | 71 |
| 413 | atttctcgagttgttgaatcatgttaattgccaatggt | 72 |
| 511 | ttactcgagactctactaattgacaagtatg | 73 |
| 547 | gtcaagattggaggttccttgag | 74 |
| 548 | tccatctcgagtacctccgctgtgtgtttcaaag | 75 |
| 549 | gtgcctcgagccacatcccgaccgcc | 76 |
| 550 | agcacctcgagtactgccctagtgccctaatc | 77 |
| 602 | catccttacaggacgtactgg | 78 |
| 611 | atgcatggcaaaacatcccctg | 79 |
| 612 | catggagatgaaatgttctg | 80 |
| 777 | ttaactcgagatacaagagttataaatcatatac | 81 |
| 839 | atatctcgagatgcatgtaagataattccaattaga | 82 |
| 858 | cattgctaaaatctctccacactcgaatc | 83 |
| 901 | atatctgcagtcatgaaactttcattatgtatc | 84 |
| 904 | atatgcggccgcggaacgaatttgtcgagctctct | 85 |
| 908 | ctttcgtgttgcctcaagagtg | 86 |
| 909 | catttcttaatacggacctgcc | 87 |
| 943 | atatctcgaggaattcatttccattaacgagaatatgac | 88 |
| 944 | catcttcacaacgctttatcacttc | 89 |
| 950 | catatgcgtacggagttgtgg | 90 |
| 951 | tttcgcgaagttacctaacc | 91 |
| 960 | tcatgatgttaagcgttttca | 92 |
| 961 | gttaacgaaggaggtgtccg | 93 |
| 970 | aagcttagcaagcagctctcgcag | 94 |
| 971 | atcgacgatagactgcaagcc | 95 |
| 983 | aggagtgttacacatcttttac | 96 |
| 984 | ggctaagacgacgcattctgtg | 97 |
| 1000 | ggatccgagaggaaagagagag | 98 |
| 1001 | cgcttacaatgatcctgcatag | 99 |
| 10R | tcdgtgaatcaatctcgtccat | 100 |
| 8F | cggtacctacaagggcctctcg | 101 |
| 9F | tgggacgtatcagggtacgtct | 102 |
| F7 | tatccggaggttcccgcgacacc | 103 |

REFERENCES

Altschul et al., Nucleic Acids Research 25 (1997), 3389-3402.

Berlin et al., Genetic modification of plant secondary metabolism: Alteration of product levels by overexpression of amino acid decarboxylases, in: Advances in Plant Biology, Studies in Plant Science, Vol. 4, pp 57-81, DdY Ryu and S Furasaki (eds), Elsevier, Amsterdam 1994.

Cove et al. Trends Plant Sci. 2 (1997), 99-105

Engel, Am. J. Bot. 55 (1968), 438-446

EP 1 206 561 A

Frahm "Biologie der Moose" (2001), Spektrum Akad. Verlag

Gorr (1999) Biotechnologische Nutzung von *Physcomitrella patens* (Hedw.) B.S.G. Dissertation, Universität Hamburg.

Grimsley et al., Mol. Gen. Genet. 154 (1977), 97-100

Hiwatashi et al., Plant J. 28(1) (2001), 105-116

Hohe et al., Plant Sci. 163 (2002), 69-74

Holtdorf et al., Plant Cell Rep. 21 (2002), 341-346

Liebich et al., Nucleic Acids Research 30 (2002), 3433-3442.

McElroy et al., Mol. Gen. Genet. 231 (1991), 150-160

Reski et al., Planta 165 (1985), 354-358

Reski et al., Mol. Gen. Genet. 244 (1994), 352-359

Reski, Botanica Acta III (1998), 1-15

Reski, Planta 208 (1999), 301-309

Reutter et al., Plant Tissue Culture and Biotechnology 2 (1996), 142-147

Richter et al., Gene 290 (2002), 95-105

Rothnie et al., Plant Mol Biol. 32 (1996), 43-61.

Rother et al., J. Plant Physiol. 143 (1994), 72-77

Sambrook et al. (1989), Molecular Cloning: A Laboratory Manual, 2nd edn. Cold Spring Harbor, N.Y.: Cold Spring Harbor Laboratory Press Schaefer et al., Mol Gen Genet 226 (1991), 418-424

Schaefer (2001) Principles and protocols for the moss *Physcomitrella patens*. available on the world wide web at unil.ch/lpc/docs/PPprotocols2001.pdf Schaefer, Annu. Rev. Plant Biol. 53 (2002), 477-501

Schlink et al., Plant Mol. Biol. Rep. 20 (2002), 423a-423f

Strepp et al., Proc. Natl. Acad. Sci. USA 95 (1998), 4368-4373

Töpfer et al., NAR 15 (1987), 5890

Watson et al., "Recombinant DNA" (1992), Chapter I.1 and 2

Zeidler et al., J. Plant Physiol. 154 (1999), 641-650

The invention claimed is:

1. An isolated nucleic acid molecule comprising a wild-type, nucleus-derived moss expression promoting region (MEPR) having the sequence of SEQ ID NO: 24 or an expression promoting fragment thereof having an expression promoting activity that is at least equal to the expression promoting activity of cauliflower mosaic virus (CaMV) 35S promoter.

2. The isolated nucleic acid molecule of claim 1, further comprising a coding region for a recombinant polypeptide product under control of the MEPR.

3. The isolated nucleic acid molecule of claim 1, further comprising a selection marker.

4. The isolated nucleic acid molecule of claim 1, further comprising at least one sequence that is homologous to a genomic sequences of a species to be transformed.

5. A method for the expression of a recombinant polypeptide product in an eukaryotic host cell comprising:
    providing a recombinant DNA cloning vehicle comprising an isolated nucleic acid molecule comprising an MEPR of claim 4 and a coding sequence for said recombinant polypeptide product under the control of the MEPR;
    transforming said eukaryotic host cell that does not naturally harbor said coding sequence under the control of said MEPR with the cloning vehicle;
    culturing the transformed eukaryotic host cell in a suitable culture medium;
    allowing expression of said recombinant polypeptide; and isolating the expressed recombinant polypeptide.

6. The method of claim 5, wherein said eukaryotic host cell is a plant cell.

7. The method of claim 6, wherein the plant cell is a moss cell.

8. The method of claim 6, wherein the plant cell is a *Physcomitrella patens* cell.

9. The method of claim 5, wherein said host cell is a protonema moss tissue cell.

10. The method of claim 5, wherein the culture medium is free of added phytohormones.

11. The method of claim 5, wherein the cell is a *Physcomitrella, Funaria, Sphagnum, Ceratodon, Marchantia*, or *Sphaerocarpos* cell.

12. The method of claim 5, wherein the host cell expresses said recombinant polypeptide product transiently.

13. The method of claim 5, wherein the expressed recombinant polypeptide is post-translationally modified.

14. The method of claim 5, wherein the expressed recombinant polypeptide is expressed in vitro.

15. The method of claim 5, wherein the expressed recombinant polypeptide is a metabolism modifying protein.

16. The isolated nucleic acid molecule of claim 1, wherein the MEPR has the sequence of SEQ ID NO: 24.

* * * * *

SEQUENCE LISTING

<160> NUMBER OF SEQ ID NOS: 103

<210> SEQ ID NO 1
<211> LENGTH: 1533
<212> TYPE: DNA
<213> ORGANISM: Physcomitrella patens

<400> SEQUENCE: 1

| | | | | | |
|---|---|---|---|---|---|
| tagcataaga | taaagatgtt | ctctacctaa | tttattttta | tttatcacta | ataactcata | 60 |
| tcaatctaaa | atatataaat | gcctttaaca | atagaagaat | atgattcaac | aaacccaatt | 120 |
| ctatcattaa | aaatatatct | aagattagat | atgataaaaa | tagataataa | tattaataaa | 180 |
| tcattttaag | gttgtaatgc | aactataata | attttaata | ttataacttt | ttagtttttt | 240 |
| aaaataaaaa | taaaatgtta | aaatattata | aaataattat | actttatata | tttatgatca | 300 |
| agttagtaca | ttgatacatt | taaagtccaa | aataatttaa | tgataccaac | ttgcaaaaaa | 360 |
| tttaatatta | ttaaaatatt | ttaaaaagtt | aagagcaaga | aaaattattc | taaatagaat | 420 |
| tcataccatg | gtattataaa | gatacaaaga | atcaatgtgt | atttattat | tttacataca | 480 |
| ttacttgcaa | tatatggttt | atactacaaa | tgactatata | ttgaagatac | taaccacaaa | 540 |
| aataaaaatc | cagcactaga | taattctaaa | aacatgaaat | acaataaaac | attacattac | 600 |
| tagcttatat | ggttactaaa | tattttaa | ttatacaaat | aaaaaataaa | aataaaacaa | 660 |
| aaaaatccta | tagtgacaag | aaataaaata | aaataaaaaa | attataattg | accaatccct | 720 |
| aaaacattaa | tatttaaggg | atattcatat | gacaataaag | ataatttatt | tcatggaacc | 780 |
| ttgattattt | tatcttttaa | aggtggtatt | tttaaaattg | tttaatggta | cttaaaatat | 840 |
| tgtatttata | tagagaaaat | cctccaaaaa | aattctctca | caagggaata | gaattcctca | 900 |
| agtttttctc | ttgactaaat | tgaccaacca | ccaaacaacc | cacgtcatcc | atccatccaa | 960 |
| cccccacaca | acccaattgt | ttctccattg | tagacatcga | caaatgaaaa | tcatccgatg | 1020 |
| acgtatacac | ttcatcctct | ggtccctcca | gggtgccatg | agccacatcc | cgaccgccta | 1080 |
| tttcagatcc | gacggcacag | ggtgacagag | cagcggtctc | agaccacgcc | atttggaact | 1140 |
| cgccagccct | gccccagcta | acagtttcaa | agctgcccgc | cataaccggg | tcctcccagg | 1200 |
| gccgttagat | cgtccatcct | acgggagcac | atataatact | gccctagtgc | cctaatccga | 1260 |
| tgggaacggg | gagtccttta | tctctctcgg | aaagcgactc | attcgccagt | gtgcgcatcg | 1320 |
| cccgtgtccc | aaggcaccgg | gccagactct | cgcatcggct | ctaccacac | tcaccccac | 1380 |
| tcaccctgtg | ttttctctgc | ccccttcgcg | ctcttcgtgt | gtgtgtgttt | tttcacggtc | 1440 |
| gattggcgag | ttgcgaagga | gggcaagggt | gctgtggtgc | agcatcagct | ggtagtaagt | 1500 |
| cagtcagggt | tcgggtcgcg | gtagttggac | aag | | | 1533 |

<210> SEQ ID NO 2
<211> LENGTH: 1539
<212> TYPE: DNA
<213> ORGANISM: Physcomitrella patens

<400> SEQUENCE: 2

| | | | | | |
|---|---|---|---|---|---|
| atgtatttcg | gagcgatttc | gtgtgctgtt | ggtgtctttt | ggttggaagc | gatttaaaca | 60 |
| ggagagtctg | tttggtggct | tagggtaatt | cggtggagcc | tgaaagatat | tgctacgtct | 120 |
| tgaaatacca | tcttgtttca | gtgcgcattg | cttgcaaaag | cattgatagt | tgtagcggga | 180 |
| tatggtgctg | tttatggttg | tatttgagca | tatgtttcgt | gacatctgtg | ttgcttgttg | 240 |

-continued

```
ggcttgccat actggtagtg tcttgttgag tatcatattt actttccaat gtaatattca      300 acatttctc ctagcattac tataccattt ccatctattc ccaatggcgc tatcgtctcc       360
ctgggataca tttaacccat atttgtagtc cagtgcatta aatgcatgtg aaatcgcatt      420
tatagatgcg catatttaat gtcaaattag acatcttcac tcatataata cattttacca     480
aaaaatgaaa tgtacacaca gaatattttc aaactgccga ctatctcaaa acctataca      540 ttatcaatct cattgacata cctcattgaa atactcctca ttgaaatact acataatttt    600
cattgtcaat attgccaaca ttcaaccatg agaagctgat tattatttct tttatactgc     660
ttactctctt aatgcaaatt caccattcct catgagagca gctgtatcta ctcccctgat     720
caatattact actaacttct caggaatagt actcgatatg ttgcgctggt tcagttacgc    780
aattataaag tccatcgtgt aaaccataat cgtcacaact ggatatctga tgccagaatt    840
tcagcaaatt ttagtgccga tccgaccagt tcaatgcaga agaggaatat aactatctag    900
aggttgttca caatcttttt cattacagtg cagccaaagt tctgcaacga agatacattc    960
gcaacttgca tgcaaggtga agacacatat cgcggctaga tcctcagttc gttgttaata    1020
cctgggaaag aaaatcaaca aatcgaattt ttctgcatca aatagccatg acaaagatta    1080
gtacttccag tgcaagtata gtctgcggaa atatatcgca gtcctcgtac tacagcttca    1140
aaatttgggt acatgacgag gatttcgacg cacaagaaca gaattaaccc gatcgtatcg    1200
agcgttacag taaacgagac gaagtgcctg tgtcttcaaa ccggcagatc tctacgaagt    1260
aagaatctac tcagcagtga gagcgagagc atctggtgtg gcagaatcta ctatgattac    1320
aagtgcccta tactgaatgt agaagcctgt atccacctca tataggaaac gaagtaatcc    1380
ataccgacat gttacatatc tccactgaag cagttccgta tgggcataca ggaaatgatg    1440
aagcacaacg cgtataccaa ttttttatca gatacacaat cacccaattc aaaacgcacg    1500
tttatacaac caacacgcca tactcaagat gagcaggca                            1539
```

<210> SEQ ID NO 3
<211> LENGTH: 1197
<212> TYPE: DNA
<213> ORGANISM: Physcomitrella patens

<400> SEQUENCE: 3

```
tccttagtcg agaaggcgcg ggacgtgagt gagctctgaa gataagcttc caatttgcca      60
ctgcaagtgt aacctgctcc atcgggcgcg agtccgtagg gatcatgaac acctcatttc     120
acttggcgtt agtgcactct agcggcattg aagcaatcca tgccctcaga atgagtcgcg    180
gggggcagtg aacgaactag ttaagaaatc cagtaatgac ggcaccacat cggcagatcc    240
agatccattg cagattatcc tcttcagccg gaccgaataa accatgccta ataaccacc     300 ggaatgtgtc ctgtgcggga ctgattgttt tccaaagaaa cactaactaa ttatatccag    360
acagtgggat gtatgcgggt atccgtgaag ccagatatga gatctctgat aaacctgagg    420
aagatgtctt acatggcggc acgggaaaca cgaagaaaag ccgaggagaa ggtattgaaa    480
gctgagcata gccattggct ggtgaggaaa gggcatgcaa caactcatcg aaagcggagt    540
aaactttgaa atcccgtagg cttcatgcga tgttctaaat tcttagcctc gacgacgatt     600
tcaaggtctg attcgaagct tccgagcggg gctccggaac tgtcacttca gtcgactttg    660
aaatgtgaag cgactttgct cacttgtgac acagcaattc aactccacaa tataaaaaaa    720
tcgcgaaaca aaaaaaaaaa aaaaaaatc tactttactc gtcgatgttc cactcgaaga    780
```

```
caaacagctt taaagcgttt acctgtggta gagatagatt tcggcgaagg aattcaaatc    840
cagcaaccct cccactcgta ccgcagacct tgagtttgaa cggttctgtt gctgtttgcg    900
gtgagttcaa aactcgactg acctctctga aaccaaaagt ttaccttgag ctgcccgaga    960
atctccgaac gttcgatata agatccaacg gtctcaagaa attctccctc gaggaacacc    1020
tatgcccagg gcaggggggt tcctttatct ttctccctct gccgcaatcc atttcattgt    1080
gcttgcagga ctgtcatccc tccccttgtt gccagtggta tccggaggtt cccgcgacac    1140
cttctggtgc cggaactaag gtctgttgtt cctttcgtga ggtagagcac actgaag      1197

<210> SEQ ID NO 4
<211> LENGTH: 1012
<212> TYPE: DNA
<213> ORGANISM: Physcomitrella patens

<400> SEQUENCE: 4
atgcgacccg aaggatgagt acacgcgttt tggttttacg ttactgactt ttagctcctc     60
cattcacact gcaggccctg gtttactgtt gaaagcacgg ttataccctc cgtaaactga    120
acattctgtt tcagcgcgtc gtgtcttagt tgtcctttgg ttcactttt agtttggaag     180 caagtcgttg tatagatgat acttagcaca tatagttgct gtcgatttgt tttaagttca    240
gcattccgct gcctgaattt cagtaaatac cttgtccaac ttcgatgcaa tataagttgg    300
cttcagtatc cagtcttgcc ttactccttc attgcaatct tggtggcggt ctggtgcgcc    360
tcgtccactt tcacgatgta cctcgtcagc ttgtttgaac acttcctttc tcctactgag    420
tatggcgttg gcctcttttt ccaagctctg ttgatgtagg tcctaccttg tcaaaacatc    480
acccacagag atttgacgac aatcgtaatt ttaatccgat tgtatggggt tcctgtcata    540
gtcaatatat taacgcccat cctctcactt accaacgtct gttaccaact ggacaataat    600
gcattcacaa ccaaagtgca attttttgtat gagttggaaa tatcgaaaca gttagtgcca    660
gtaattcacg caaatagttg tgtcatggaa acttttttt aactttctgt tgtccaatca    720
tcgtgctgaa acatttagaa atgtggcaga cagttgcatt tgatgtatca actgctgtgg    780
tagtaacact tgttgaaact gtaagataga catgccaact ttctggtgct atgtgctaat    840 tgttatatc ttcctgaaga atggtacaat tcaaatgaaa gtgggtggga gaattgatat    900
cattgatagt ggaataggtt attgcaatca gtgagtcctt ttttcagggt agctaatatt    960
ccttactgat tatccattga ccaccagtgt ggcttgtgga atgcgtgaag tt           1012

<210> SEQ ID NO 5
<211> LENGTH: 1386
<212> TYPE: DNA
<213> ORGANISM: Physcomitrella patens

<400> SEQUENCE: 5
ccgtgggact tagttgtctt cacttcatta ggaaatctgt ttgagcctct ttccattcca     60
atcttctcga caaaataggt ttttcagtg actcataact tattgtgctt tgcaaaattc    120
ccactaatcc gaaatgtatg gtgtgatcac cgagctttta aattgattgt gtttgggcag    180
tctacgaaaa atccagacgt ggagccttcg aggaacaggt tgttcgcgca ccgctacttc    240
tgaacttcac aacgccgcgt ctatgtcgct ctaactcaga ggctataaca caagttagcg    300
atgtccatcc ctctagtctt catatttgca acattaggag gaggcacacg ctggtcgaga    360
tgcccgtgga actcttccag attgctacca tcaatgcact cgtagacaga tccaaaagtc    420
attccacatt attcaacatt aagggatccc caactgacca accaagagca ggtgctatga    480
```

```
gtggaacttg ttattttcca aatgagcgtc gactacatat gcccaggcag aaggatatgc      540
cgaggtatct ggggggggcag gcatgtgttt tgtgtaaagt accccgagg taagaacttt      600 taagcggcgg cactggattc agaaacagtg gacagatata tccattgcca atgtattgat      660
tggctggcga agaactgttg caaccacga ccagccgtag gggcgtaaaa tttgaatcca      720
ctgtttaaat ttcaaatttc aaacctcgac ggagtttcct ttagcttttc agatgggcgc      780
agaacggtta ggaaactgtc ccgtcgcccg aatttgaatt taaaaaataa atcaaaacgc      840
tagagcttcg attagtatgg gcttttttca ctcttctgtc caattctttt tgttttttac      900
ctcatgcaag gcggtcggct aaagtgactt acagggagga atattactga gagcaagagt      960
tttaccacgt tgtaggatct ggagaaatcc aacgatgcta ggcctacgca acgagtgtga     1020
ttcaacgcca gctataatct cattcgtgcc gtcgatcccg ccatccaacg gcgcagacgc     1080
tttgcgtggg aattgtacct tgcctacgat tggaatttga ctggcagctc ttgagctgga     1140
atttacttgt ctgcctgaga aagttgaagc gtaagatgct cgatccaacg atgggcagaa     1200
agtgttcgtg ggcaggaacc aaagccctag ggcgggctcc tccttttatc tatctctctg     1260
gcatatctct tctcagtgtg cccccaggga cgtcttcttc tctccttttg ttcagcgtct     1320
cagtgctcga gggacggttt gccgtctttg tttcttcgtt ctcgttgtag atcatcctta     1380
gcgaag                                                                1386

<210> SEQ ID NO 6
<211> LENGTH: 997
<212> TYPE: DNA
<213> ORGANISM: Physcomitrella patens

<400> SEQUENCE: 6
ttgtgacctc tcctctcgtt atcattacgt agcacgctac gaacaggaca ttctgtttca       60
gcgtctaggg tctttcattc agcatttaga accaaatcat tgtatagatt tcacccagca      120
taccaagtag ctattgattt gttgtgagtt cagcatgctg ctgtctgatc cgaagattat      180
ttgtaattga ctgttatatt tgagcatttc tgttcaatca tgtggtgtgg gtttgaattt      240
taattagcag gcactgagtt ccgtgacccg aaaagaattt tctgagaata gccaggtgag      300
ttgcttcctc ttttgctgtc ggggatattt cttccgaaat atgggttatc cagcgctcta      360
tccgcttctg ctctgtgcta tgtgaacatg aatgcaattg atattcttcc aacatccata      420
taactaatgc atacttcata agaaagcaga ccgtcacgga taatgggaga acatttttcc      480
agtcatctcc gtgtccacat ttctctcaca cgctaaccat gttagtaaac cgcaaggact      540
gttattaagc aatgaatatg tctgaaaatc gtatgtgatc tgttgtcaaa gtgtcatagt      600
acccgtcatc gccgcattgt gcactgctgt cagatccgca gtaaatacc gctaacgaaa       660 ggaagagaaa gatgagagaa gatgagattg tcaccgggag agaatcagac gcagtcatca      720
gtgatactat tcgacggacc taacctcgtc cgtaaaatgc aagaatttaa cgaggcagta      780
aaatcagctt aaaccctccc cgcacgctta acgtaaccat ggctgtgcta acatccacc       840 aagagaggaa acaccgcaca tgaacaactc ttctgaacta cacgtgaagc agagattgag      900
gcgaaaagaa agccacagat cgctgctcct caagtggtga atttatttc ccttggaaca      960 aaaatggagg tgtggaggcc aagcagcaat ttcgatc                               997

<210> SEQ ID NO 7
<211> LENGTH: 624
<212> TYPE: DNA
```

<213> ORGANISM: Physcomitrella patens

<400> SEQUENCE: 7

| | | | | | |
|---|---|---|---|---|---|
| ctcgagtgca | gtagacgaca | aaatggaagg | atgcgaccag | ggatgaacgg | gaagagtatc | 60 |
| attaatgcga | gacccttgga | gttgaaggcc | acgagtggga | cagcgatgcc | gagaaaaatt | 120 |
| tgaaaatcgc | tcatcccaga | caaaatatct | gtgggccagc | cagggtttcc | cagccagctg | 180 |
| ctctgccgtg | ccagccgtag | atctgctcat | ccgacggcca | ctgcgcccca | tcctggactt | 240 |
| gtaccctccg | gcatttggaa | agtgtcagcc | tctccctgac | gaacatttca | cctcggctgc | 300 |
| ccgggaggcc | aggagcgtca | gatggagat | ctgacgcgg | ggcggaggag | agacctgaac | 360 |
| cggcgggcag | gggaacgatg | tcgttgcttg | ttcttctggc | tgaggcgtcc | atccccttta | 420 |
| cctccgctgt | gtgtttcaaa | ggccgatatc | tgcgcttccc | ttgcggaccg | agctctgtcc | 480 |
| cgctcgctta | cttctctccc | accgagcttc | cgaggttggg | cattcccacc | cttccttctc | 540 |
| ttctcctctc | cttctctgct | cttcttctct | gttgtctgcg | gattaggtct | tgtggtcttt | 600 |
| cgagcttcgc | acagcttgag | caag | | | 624 |

<210> SEQ ID NO 8
<211> LENGTH: 1146
<212> TYPE: DNA
<213> ORGANISM: Physcomitrella patens

<400> SEQUENCE: 8

| | | | | | |
|---|---|---|---|---|---|
| gcgcgcggtt | ggctggaaga | agagtcgaga | agcgatgtgc | ggcagcggca | gcagcaggag | 60 |
| gggcaggcag | tcaggtgcag | cacgtcgctg | gggtgatgcg | gagggacttt | gccggttggc | 120 |
| tggggtacag | aagcgagggg | taaatatagt | aagattacgc | gcggcggaag | gacgcgatgg | 180 |
| ccaacgaggt | ggagggggttg | gggcggtttt | acgtgtacag | tatgagactg | acactgacgt | 240 |
| tgatcctgcg | cgaaccaccg | gggctagcgg | tagtagatag | ttggagcgag | agttcgggag | 300 |
| cgttgttgcg | gataagctcc | ggcgtttgac | cccagggtgc | aaccgtagtt | gcatggggggt | 360 |
| ggtgggggga | ttgaaattgg | aaccggactt | ggagttgaga | agttcgggtt | gttttttggag | 420 |
| gcagttgaaa | gacgttttta | agaagtttga | gctgttggaa | atacattgtt | accctgagct | 480 |
| taagcagtgt | gtagtggcga | tgtgtttaat | tgtctgattc | ctgtatgttg | gtgtgtgcga | 540 |
| ggcgtgtgag | tgcgtggttg | tgtgcttgac | gtggcggtta | tgggccgtgc | tgtcggaatg | 600 |
| atttactgga | ttatttggtc | cattggtttc | gtggactgga | gacggtggat | gtttgtagtg | 660 |
| cttgtgtgaa | caaggcgggc | atgcagatga | tgggctcgca | ataaagacag | ggtcatgtcg | 720 |
| ggtattgccc | agatgaaagt | ctcttttggt | gatgccgata | cggaaaatgg | aagttggtac | 780 |
| agtcgcacgt | tcaggcgtca | tgggttgcct | tggaagtttg | cattggaaga | gagagttgag | 840 |
| ggtgtcctgg | atgatgtcca | cgaggtggtg | tttgaatcga | tgttgtgcga | agtagacctg | 900 |
| agcaccgatg | tgtgacaccg | gaatggtgag | tttgtgtcaa | tgaactgtga | gcgttttgat | 960 |
| tgaggcagac | attccaaggg | gatggttttt | cggttttgtc | ttttaaggct | ggcgcctgcc | 1020 |
| tagcctcctt | tgtccttcag | cgcatgtttg | cttgtgacgt | ttgcgttggg | attgttagta | 1080 |
| ttggtctgga | tggaaatttt | atcgtttcta | tcggcagcaa | ctaagtgcgt | cttgtcattc | 1140 |
| ccatgg | | | | | 1146 |

<210> SEQ ID NO 9
<211> LENGTH: 2973
<212> TYPE: DNA
<213> ORGANISM: Physcomitrella patens -continued

<400> SEQUENCE: 9

```
ggatccattc aacggaggat aagtatgtag ggtgatactt aggctcattc attcattcaa        60
ggcgtattta attaactact aaagaaaaaa aggggttaa ttggggtgat tgggttatgg        120
aatgaataaa tgaataaatg ggtccccccc ctccccttcc tttcccttcc ctgcattaca       180
tatatatata tatatatggc atgcggtgct gagggtgtgc atgtgggggg ggggtgtgt        240
tgagagtgtc aacggtgcca gccacactct ccggacccct tcccattttc ctttcctttc       300
ctgccctgtt ccctgtccct gctcccaccc actttccatg cccttgaaca cttcctgata       360
aaggccctcc atccctccct ttccttctc aacccattta attctatggc ttaaacatct        420
aaatcattac attcttatgt actaaaattt tatttataga ttgataattt tcttttaatg       480
aattaagttt gaattttatc tatgttttag ttccacaaga tttgttttat ttattacatg       540
aaacttcaaa agggatttga atatattaaa aatttccatt tataaatgaa tattcgagtg       600
agtttaatta aaattatttt tagcgtatat atatatatat atatagatat ggataaaata       660
caattgaatt aacctaggtt taattttat aacaatgttg aagtgacctt catgtagtgt        720
gagtgcaagg atgtatttgg atatggatgt acttcaaaaa aacatgata aataattgca        780
tagtattaaa gtttatgcaa taagaagct agaaatgact aaaaattatc acaagcttat        840
taactcacaa acaaatcaat gatatttcat atcaagtgaa actgttaaca aaagaaagaa       900
ttacgtgtat atttcatgat catattcttt tgataattaa tggtagggta acactatgaa       960
cataaaatta ttgctctcta caatttatca aaagtataat aaaacaaaaa taaaacagaa      1020
atcataattt atgagtctct acagggattc actgtcaaat attgtaagta aagtgtgtac      1080
tattaattga ggggattgtg gtatgccatt ggaatacgtg gatcaaaagc tgaaacacaa      1140
gaattttgaa actcaaaatt acattaaaat gtttgaaaaa taaacacaaa atacaatttc      1200
ttcagaaaaa aaaaaaaaaa accatcgtca ataatgacag tcaacaaagt cagcatgcat      1260
gacgagctca ttgtatttcc tccaaaaaaa aaaaaaaaa gaagaaaaag tgggccctca       1320
gttaaatcag agaatgccac atggtgatag gagaagagcc gatcataggt gatacgtggt      1380
catgggatca tcgtttccat gcgcggaaat agatcgaacc cctctcagtg tctgacgggt      1440
caacacgggt gatcgggtgg acccaccctg accagcccaa caaaacgcag ggaggaagag      1500
gtggcaagta agtaagtccc acgtggattc gagacaaaac gttgtacgaa taatatacga      1560
agtgagaaaa aaccacagag cgggtggcag tcacgaagtc gcagacacaa accgggctgc      1620
ttgacacggc gacccgttcc ctgttctgcc gcccgttccg tcgccatctt tgtctcattc      1680
gcacaaggtt cctttttccag tgccttctgc gcggtccca ccctctccat ctgacccggc      1740
ccgggctaac ccgttccgga gcagatgatg atcgacccgt ctcgcaggct ccttttgtgc      1800
accgcgtggc ttcgtgattg ggccattgtt gctgtttgct gtttgttgct ctgctttctg      1860
tgtccgggcg gcattcctga gaggcgattt gcatgcgcag gctcgttgta gagcagcagc      1920
agcgctgagg gtctcgtcta ggcttagtct gcttctatcc ttcgctgctg tcgcctctgc      1980
ttcatcgtcg ccgtctcttc tcaggttaga gcactttcaa gtgttggcca ggactgagta      2040
taggaaggag ggtttatta tttatttatt tatttattta ttttttctgtt attttttattg      2100
ctggctgatg tccatcttcc gacgcgatcg tcgtttttttt tttttgttt gtttgtttca      2160
ttgtgttgga ggagtgtaag atttaatcgg atgcataggt tgtgtgtttt gcatgcgttt      2220
agagcgttta catgtgcgat gcacgagctc tggtgtcgtt tagaggccac tgatttagta      2280
```

-continued

```
gtttcttgtg cgaggggat tagatcttgt accgcaagat gttgctccgg ggttgtggtg      2340
gcgatggcgt tttataatta acatatagtt caatggtgat gatttaatta gcagtggtgc      2400
atgagttagg tacgatcgg gcgattgtgg atccggactc gtgttcaaca ataggctgga      2460
ttctcttcta ttgcgattgg ccagttctta catgcaatcg ggtacacgat cgctgaagta      2520
gaacaaatta aactcatcga ctgaattttt gccgtctcct gaactgtcga aatagagctt      2580
gaaaatttga ttgatagtga ttgtttagtt ctctgcgaaa tcgttctaca taatctttaa      2640
attctgaatt aatctcaatg tattttgaca tcagctgatc gcttgtccgc tcgctcagtt      2700
caattcgatt gagtattgcc tgcagatttt tcagaaaaat ttaagtaatt tgatagtaag      2760
aacttgactt cctgtggatt ttaaacagta tagcatatga agtgccaggt tttctgaatc      2820
ctccatttct tctaatcgct atttccgaag acttctatac agtatggagg gcgttctgta      2880
ctgtcctgat tgcgagacat gttttacgac gaaaatttac tgctccttag aactaaaatc      2940
ttctgaaatg gttgggcagg tcggtattaa gaa                                    2973

<210> SEQ ID NO 10
<211> LENGTH: 1128
<212> TYPE: DNA
<213> ORGANISM: Physcomitrella patens

<400> SEQUENCE: 10
agcagtgcga cacatctttt gctttttca gcacgtctct tagctcggct tattgaactt        60
cgattgctaa cgtttgtggc caccgaatta ggcctgctag cgtagatcaa ttagaggtcc       120
atgttgcaga aagcttttgt ttgtaaaaat agctgatatc tggacgcata cgactggctg       180
atataattca gtgccattca cattatttgt taacaggtcc agggttgttt gtagagtcgg       240
acagcatttc tcgtcggaat gttggcgccg ttttgtgaaa tgaaaggtga ttatgggtaa       300
aatgcataca tagtcctgtt gactatggct gagtggataa gatatatttc catcacaggt       360
tagatttcct gcggagtgtg aactgtgacg taaaatcaca gagtgcgtcg tcttagccct       420
agcccccgaa tcatccttta cgatggatgc atgttcggat gttataattt gattttttt       480 ttttttcgtt gtttacggat ttttgaccag tttaccattt gttgtttcag ttgtgatggt       540
ttggttctgc gtagataagt ttgagttgag tatatttcgt gagacgtcct acgccactgg       600
atatgtatcg ctgaagcaga atactgagta ttgtaattgt atgttccaga cgtttcagta       660
gttagtgaca gtggaatgaa gcaacttggt ttttctcttc tatggtcttg ccaatcgttt       720
ccgtcgcgag attgagcgta cctggtcaag ttgtgttatt ggtgagctca atgtgcttgt       780
gattggtcaa tttccatata taagtgaagc gccattttca aggagacaag gagctctatt       840
ctaggcattc accagtcctc ggctccaggg gcactcggga gatgaggtca agtctcattg       900
ctagagtcgg ttggtgacca ctctgaggtg gctcattact tgggatatat tccatggcga       960
ggtttggttt tgcatgctat cgacgaagcg gctagaactc tgggaatcta attattttgt     1020
ctaatccgtt gcaggacgat cagccgtgaa acagatacct atattttaag aatgtttatt     1080
cttgtgtgcc atgtgtttgt tattgaagaa taatcttcgg tgacggtg                 1128

<210> SEQ ID NO 11
<211> LENGTH: 3035
<212> TYPE: DNA
<213> ORGANISM: Physcomitrella patens

<400> SEQUENCE: 11
cgagatcggt ctgtaagccc tgtatttggc atggaatatc ttttaacaaa gaagatccat       60
```

-continued

```
cttttagttt ctcataatgt tgaacaacgt acttaaggat ttagaaagtg tgtttcgttg        120
cttctcttgt tagaatggcg ttatgagcct gtgctgtgtt cttcttttta gctggatgaa        180
ctgtacaatg tttcacaact gtagcctagt tgatcgtgca tatttgcgtc atgactcccg        240
gcaagttgat gtgttttttt cttgcttttg aatcccttca acctgtattt ggtggctcgg        300
acagtaactg ctacgatata cgtcagtctt tagtaagtaa tatgttcctt tttctctcgc        360
ctcacgtatg tcatatttcc tgagatagtt ttttaatttt cgctctgtgg tttcttgtag        420
tcctttcact gcgtgccgct atcacagctt ggtcatagag gaggccacat ttccagcgga        480
ccaacttgag gttacagcat ggactgagga cgggcttgtg atgggagtcc gtcacaaagt        540
ctacaagcac attcaaggag tgcaatttca tcctgagagc atccgaactc aaaacgggat        600
gcagatcgtc ggaaactttc ttaagatttt agatagaaag gagacggctg acaagaagga        660
gttgaaacac aaattttgga gagtgtttga gtgatgagtg atactgggat cctttttat         720 gggaaagatt gccagcagca gtaagcttgc ttttgttaga ttcctctccc tacagcgtgt        780
acctcctcga atatgcactc aagcaagcct agaggttgct gctatagatt tctcggtaag        840
acagggtatt attgaggcat tttttgcgct tccagatgga gctactacca caagtatcta        900
tcctattatt atctttaact tcgatggatt tgccatgatc actgaggtac gtcgaagttg        960
tgattggact tgtagtgatc acttccagag cgagctatca aactggtgcc tagaggagca       1020
acgcaaggag tgctgaatta ttctaatgat ctcatttagc ctaagttttc cgtcaaacat       1080
agtgatgttt ttaagttcat ctcgttagtg aaacatctca aagaaggtac accattaaat       1140
tattgcaggg gttgtgatga ctttatttaa tagttgacct cttcaattga gaacgcgttg       1200
ctctcctttt gtatagtttc aatcatatca aagctctatt tgttctctgt accttaagcc       1260
ttgtgtaagg catttaaata atctcttcca cgattaagat ggtagttatg tcgccggttg       1320
caacttccaa gatgtcctaa tgctatagtt ctcattcaca actcaggagg tttgttgttt       1380 tatgttttg aaagtgacga aggaaattgt ttacttttcg ctttgtgtct gtgtattta         1440 gaatagtacc ttaacttctt acacaatggt gtctaatttg ttattcttgt gtatcacgag       1500
cgttaatcgg tttggacgtc ggaccctttt aaccaatctc aattgcttct gttctaatcc       1560
acgcgtccca cgaatggcag gtcaaatacc gattattgcc cgactctaat cgtgacagtc       1620
actgagacta ataacgggag gtcactatct tgtgacgttc tcgttatttt aaaatctgta       1680
taatggcaat ccctttctgc accacggcga actcatgatg attcttatcg agtcctgctc       1740
accaacttta tcacaagacc ctacggatct aactatgatg accaaaagct tgttctacgc       1800
atgcatgagt cccttcgttt gggagatttt agaattctta ggaactcaca cgttgtccat       1860
aaattttaac caccgggcaa cataggatgt tgacatgtag tcacaaattt agaaaaaccg       1920
acttcaaaag gttgcccacg tagacaaaac aactcgaacg cagaaatcca ggcgaccggt       1980
gaaattggaa cattcacaac aaagcgagaa gaggttcaaa aaaaccgcag agtaaaccct       2040
atgcgccaga ggggaatggg agatccacgg gattcggaga tgaaaaggca tcgcgcgagt       2100
aaaaacaaag agtgcgggga gcaagggcat ccagaagagt ttcactgaga tctacagtgt       2160
aactcagaaa gggagccact ggtacaaatg ccagctttgc aacgcagaac gaacgcggga       2220
gagctaacag atccgggctc aaaatctcct tcttctacct ctcaagccgt ccacaaccct       2280
cattctccat tctcgcacta ttctcctcaa accagttgca tctgcggttc cctccatctc       2340
caaccctacg gctttcgtgc gagcttattt gttgcctata ctaaggttaa acccactcac       2400
```

```
tttgttgcct atactttgct ttgctatttg gttgctttcg tcttcgcttt tgttctttgg    2460
tttatctcaa gtgcacatgt tctcgcgacg ctgtgccgct gtaggggctg gtgggcttat    2520
agacctgagc accgaggcgt gggtttgctt cgactggctg tggttgttag caaggtgttc    2580
tcgtaaggta gttgtgttca gagctagatc ttgtgacggt gatgcgaaaa atgcgttcat    2640
cagagttaag tgatagaggg cttttcgtg agatctgctt ctgtgatgga tctgctgtga     2700
aagcggtccg cgttctcctt tatcttcagc tctgtgtctg atgtttggga aatgcatcct    2760
ttggatacgg tgcgattcag gctgtatatt gaatccccga gttttggaaa tctttatgac    2820
ctcacttaat ccgaaagcta atgggctgta ttgagtgagg ctaatacaca tctctccata    2880
ccgcgcttcg gtttcgactc gtcttaccga ccacattgat tcacatgcgg agacatcagt    2940
gttggatcac ttacagtctg acctaaatag cacgtgtgct acacatagtt tcaatgccag    3000
taacagtctt tgatgtgca gagtatttct tctcc                                3035

<210> SEQ ID NO 12
<211> LENGTH: 1221
<212> TYPE: DNA
<213> ORGANISM: Physcomitrella patens

<400> SEQUENCE: 12
gctagtgcat acctgtctcc tgaaatgcta tcacaccttg tcaggtgggg ttatggagtt      60
tatttgtagt agctaagcag ctcgaagagg ccagtgagag actgattttt caggggttgc     120
aagggaatgg ttactcgagt aaagagccag cgctgtcgag accttcttgg tgcaattcca     180
tctttgaaag tatgcatcac aagttagatt cgtggctttt gagcttgtcc tcattatttt     240
gcctaccatt tatgttttg tggatttagc atccgcggcg tttaagtttt tgttttaaca     300
ttctttcttg taggttcgga tagaatgttg gggacatttt atgcttgaag agcgtcttgc     360
actgtcggac tgtaatgcaa tgcttgtgga cctcagcctg cctgcaata cttgtatatt      420 cgtgaaaaca atcatagcga ctctgtgtta ttcttcccat gtcattcact ggctctcgaa     480
ctttgtcgaa tacatctgat gggcacgcgt gcagaagccg ttctttaacc tcgatgggat     540
ggattagtac gatttgctgt catttaaaac tatttgctat ccgtatttgt cttctgttcg     600
gaaatttgtg tagcttgtta ttttatggta tgttgtagga aatcagcttt ggtgagaaat     660
ttgtttcata acgacacaat ggaatgatga attaaattgt tgccagacca atatcgtatg     720
tgtcaatctg attcctcaat gcagatatgg ttgtggagcg tctgctgtac ctccttgttt     780
taaccgccgt atctgaacca actcgaacgt agtttgaaaa atgcactaaa tgatgcatat     840
tcaatcggtc aagtcatatt aaacacgcgg ttttgaaagg tagcaggtgt atataatata     900
aacatgtata tcgcaaaggc ccattcctga cattggatgt gctaattaa gatctaatga     960 accgttcctg gcaatgtatc tatcaagcaa actgaagaca caatgaatcg ttgagtgtat    1020
gtagaaacac aaaacgatct tgtatttcct tttcatgtgc cagagtgagc ctcatcgatg    1080
tacactgata ggactcaact ttgatatttt ttgaagattc ttatgcctga ataaggtact    1140
tggaatcata gttctttgtc tcatggctta acttgattaa gatttgggga tttggaacct    1200
ttgtaaggag gcaatgaatt c                                              1221

<210> SEQ ID NO 13
<211> LENGTH: 3060
<212> TYPE: DNA
<213> ORGANISM: Physcomitrella patens
<220> FEATURE:
<221> NAME/KEY: modified_base
```

```
<222> LOCATION: (849)..(3060)
<223> OTHER INFORMATION: n = a, c, g or t/u

<400> SEQUENCE: 13
agactctact aattgacaag tatgtgacta caaaaggcca caagactctc tctgcactat      60
aactataagg ctcatatttt tgtccatgt  agcttgtata tatatatata tatatatata     120
tgtatattta aatcaaaata tttttattca aaaacaaaat acaataaaaa accaaaaaat     180
attttaaaaa taaataaaaa attattaata cttttatgaa gctattattc aaatttattt     240
ttaatttcta atttaagatt tattattttt tcttaaattt attaaacttt ggaatttatt     300
tttaaaataa ataacaataa aataatttat agtgttttta ttgataagta aaattaagag     360
ctaaatttgg atcattatta caaagttata atacttaaat atttattgag atatatttaa     420
atttaattaa tatttttttat taagttatat atatatatat atacacatat tatgaaatta    480
tttaaaagaa gttagtagac ttttaaatat tttttaccat gttttaattc tagtacaatg     540
tatttaaatt atcttattaa gttatggaaa agaagttagt aggttattaa atgttttgtt     600
agattggttg taaaggtttt atgataatct tgtatgataa ggttgtttag catagtttat     660
tttgcttaat taaaaaaaat tacatcttgt tacatttaaa tttaaaaaat acatactata     720
cacatatctg tatttagatt gcttttacaa tttttatctt tttgttttt  gcatatttca     780
aagaaagccc agcatgtgta taataatttg tataacccctt agaaattaat aatatttaag    840
taaataatnc ttatttataa ataaaattact gtttggtttt taatncaaga atttaaaaga    900
cccaattgtt tattccaaag taatagtagc ncattaataa aaatccttca aaaatgaaac     960
taaacaaacc aatgcatctc aaatgaaaag gagaagaatg atcttacata gacanccaca    1020
aggagggaca tgacaactta attagactat gggtttagga acatcaacca ttccctacta    1080
ccaaaaaagc ttacatgatt ttaaataaca caatattcct tgtgactttt gtgcattatt    1140
gaggatatcc atctatctag attttggaca atgttttact gcccaaattt caataagaac    1200
cattcacata ttttgaaaca catttgatac actctacatt catgtctaga gtatagggac    1260
ttgggtttaa gattagggtt tcagattagg gcttgcaggg ttacagttaa aagttaggat    1320
taaagattta gatggagtct tggttcagag agaaaaaagg atttggggta aagttttat    1380
gaaagagaat catcgcccaa acaagtagcg ggactgctga atgccttttg caatgaatga    1440
aaatttatca acgtccgtca atatgtacaa gaccatcaca taatggcccc cctgaccaca    1500
atttgaaaaa cacacacttc ctgcctggaa ccagtaatac aagtcattgt aggggagaga    1560
gagagaggga gagagagctg tagctgcgta taataagggc ctcgcagatt cagtgctacg    1620
tcgtatggat acaccgtatc acttctggtg tacaggttac taaatactac tcgacacggg    1680
gcgggccgat ctgcggaacg cgccggggcc atgtcccagg gccctaggcc cgccatattt    1740
ctctcgtcca cccgggccta cgcaaacttt cccttctcac tttcccagct cacgctctct    1800
gttcaacgca caacaacgcg tagccgagac gggttcggag cacaaagtca cccagcccgg    1860
cccgacccgt gccgtctgg  cgcctatctc tctccgcctc tgggcccgtt tcgctcctgt    1920
ccttgtgtgc tctgtctggc ccttcaccgc gcttcattgc ttcttcgacc gagagcctct    1980
tagctccgtc ttgttcacca ctgccgcggc actccgaccc cttgcatact ctcttctgcg    2040
gtgcctgctt ctccccatct cctgcatcgg tgccctgttg tgtttttttt taaaggtcag    2100
tccctctatc acgtcagtgt ttcgcatttc cgtgaagtgc tcaggttttt ttttgctgcg    2160
aactgtcggt ggagatgtgc ttttgtcgt  gtttgatgtg tgtgcggtgc agcgatggtg    2220
```

```
ggtttcttgg aggaggaggg agagtcttat tttagtcttg ttgcccggtg tgctcggggc     2280
gcgaatgtgg gtttatggta ncgcacaggt ctgcgtttgc gatatgtgtg tagaaccctg     2340
tgccgagcga tcatcataat agtagtttct cgtttcggag gggctgggct tgtcaagtgg     2400
aacgcagagt cgtagttttg agagttccag acgcgcatcg cgcagctgta gtgagatgta     2460
gcttctcggt gtgtttagtc aaggtttcgc ttttccgatc tcggatcatg tttacgtccg     2520
tcctttaagc tggatctctt gttctttaca gaacttgttc atcgccctga ctaagttgct     2580
ccagtgttgg tctgaagacg acaagcctct tctttcttg aatagtaaga agaggaattt      2640
aatctgaagg cttgttttgt acagtagttg gtcgtttatt ctttgatgtt taacttagcg     2700
tttcgttgta cttctactaa tgtactcttt agcttggtcc gaggctatta tttaatgagt     2760
catgccctga agtcgggaac agcgggttgc acctacaatc atatggatat gaggattcgg     2820
gtcgagtatt aacttgtagt cctttgttca ttgtttttga ttgcggggtt tagctggtgc     2880
aactgcctga atagcacgca ctgctttccc tgcgttcgaa tcgtcatcaa cattactatt     2940
gtgtaatcca catggctaca gctgctgtaa ggttctgcgt caagggcgtt cttcaagaaa     3000
taacctatgt cttccttgaa attaaatatt ggtggttgtt gtgcaggtcc gtattaaata     3060

<210> SEQ ID NO 14
<211> LENGTH: 4124
<212> TYPE: DNA
<213> ORGANISM: Physcomitrella patens

<400> SEQUENCE: 14
attgtccatg tgcactacta acattttttc agcacactcc cttccccggg attgagctct       60
tgctgtgtag aactctcgtt gcaagtatca gtgattgcag actttgactg gtgagcacag      120
attcaacaga ggtttatttc gcagatgact atggtttgta aaaatagcag atatctgggc      180
tcaattctaa cggctggtat atgtcagtac ctataaactt aactgtttgt agctctagat      240
cggtgtggta aagtccggta ccaattcttg tcccttttcg tattaaataa agggtatttt      300
atttcatata tcgtcttttc cttttgtcat cacatctcta tcctgtgcat atcatggttg      360
tattctcagt cgtaatggtc tttcaagtgg aatgatggct ttgatgatgt gcacctggtt      420
gtgtctctgg gcgtcatggg cttcacatga gctgcggtta cagatcacgt ccagcctcac      480
acaattaact aggcatgctt tccatttcct tctgacgtaa atgacaggct ctgacaacaa      540
tgcctggcac ttcctgacgt gggacccgtc gattggtgcc gaagtcgagc aaaattctaa      600
cctccacaac tggtatcgtg aatattctag cctcttcctg agaacagtgc cggtcgatct      660
cgaattacct cgtaatagtc gtcaggcatg tatgtatgtt taaaaatact ccatgcggct      720
aaattatttt ttaaaattta tctttggatt tgaaatgaat ttctaccttt ttttactttta     780 agttacgagc tgcgattcca actaatgaag ttttacatac taatcagaag aatgtcgttt      840
tttgaaatta acaggttaag tgttttgaag aattaaagta tgatgattcg tctttttttat     900 atcaaatgag ttttgaatga ttcgtcgttg cattttttaa atcttggaat gaattgcgtg      960
tatgtgacgt gtatgcaaag atacaaatct catgtagtcg agtacaagac aattacacct     1020
cttatgttta tggttcattt gtacatagtc tacgttagct taaggtcatc gtgtgtgagt     1080
atagtatatc tcattaccta atttgaagtc cagtaaatgt tagttatgtt accatcgacc     1140
agttatcacc gatgttgctg agaagcaatg tgaatcttag gaaacgagtg atatttgaac     1200
tggatattaa ttcatccgta atctataaac agacatgctc tactagcgtt aaaacataag     1260
ctacagcaca aaatgatcta aaaaaatgtc atcaatcata agctgtgtat aatacatccc     1320
```

```
atgaatatca acagtatgag tttgggtgtt tgtgcacacg taaaaacgaa ccctcgaatc    1380
gaaatgtgta ttactgaatt cacatgcaaa tgaattgttt ggatcattta ctgattaggt    1440
ctgtactcta ttaatgaaac atataataga tttaagactg tccagtcagt tttgaattaa    1500
gccttgggat ttgtggtctc ttcctcttcg gccactaaaa gtttaattca cattgatgtg    1560
aaagaaaaag tcacaactca gccttcgctg tgttagaaaa gctgcacgtg tgaggacttc    1620
tcaggcagcc tttccttttt cagttgagtg tcgaagtagg agcacacgtc gtcggtaacc    1680
ggctacagga ggtgtgcact gtccctttac cggatgtggg aagtcaccct atcctgagta    1740
tggctcacac ccaacgttgc tactccatcg cacagacagt tccacatgat agactgctcc    1800
gcgagaagcg tcactctcgt gcggtctcac ggcttctgtt gcggccgatt cagtgcaggg    1860
agtcgttttc gagcttgcga agtggctctc ttgtcattcc cctgcttctt ccggcggcca    1920
ttttgatgca gaattgcgaa ttctgcagaa tatgttgaga actcgtcttg ggggttttcg    1980
gatgaggagc taaacccta gagggacgga caattctgtg gagcttgctt gtaatcctgc     2040
agtacaatag aataatagag cgacatgtcg acgctttcga ctcatgctcg cgtgtcgtca    2100
ctgtcatcag tgtcgacagc gtcgaatgtg gtggcaaatg tggctgtgag gccgtgtatg    2160
atagtatctc ttctgccggt tgcgagaggg ttgtgctcta ggaagggggtt gatgtcgcgt   2220
ggacctctcc gaagacattc ttgtatgaag agtgtttcag taatgccgag agcttctctc    2280
ggtcaactgc ctgaccctga acaggtggac ttgtacatta atgcgttgtc ccagacgccg    2340
gacgccctgc agggattgct ttcgcggacc gaggggctct ttttcacatt ggcggatgtt    2400
gctgtggcga ctgatcccag ccaggtcacc gacgctgtag tgcagaaaca ggacggaggc    2460
tggcttggag gtgtctcgaa ttctcttgag atagctctta ccgtaagctc tttttatttt    2520
tattttata tatttttgtt ctttttttga actgtgaatt gtgtatattg ttttcctctg     2580
aaattttctt tcagaatcta ggtggtaaaa cattctgata cttatgctta ttgcacggtt    2640
tatctaattt actaagattt agtgtgaatg tgatgatata attttactaa aatttaagat    2700
ttttctaaaa tttaattgca gctagtgtta tctttcgagt cgatgctaaa acattcctgt    2760
tgacacgatg atcatgaaag ttagatgtgg cttaataaca aatgcaggaa ttaatgaatt    2820
ttatttattt atttattttt gcagtttttg aaggatacca ttgctaagct aggcatacct    2880
tattcgtatg gtttcgcaat tattctttta actatttag tgaaggcagc tacttatcct     2940
cttacaaaaa agcaggtttg ttgttctact gattttctta ttttgtgctt tctttctttc    3000
acttttttgcg tacaaatcat ttttgtgata tactaattta ttgtgtaaaa ctaaaagaat   3060
tactatattt ttcagctaaa tatctgtcga tgtcctgtat ttactcataa gttttatggg    3120
tttaagatag tacccagaca ggactgagtt ccattggtag gtcagtactc ctgttagatt    3180
agggaggctt ctattgttgt atatctaatt gaaagtggtt atgtttaaca ggtagaatca    3240
actttagcta tgcaaaactt acaacctaag ataaaagcta ttcagactcg ctatcagggg    3300
gatcaagagc gcattcaatt agagactgca agattgtata agcaggctgg agtcaaccct    3360
ctcgcaggtg caattttgtc gaagtcctcg aagcattaat gttaagaatg cttgcagatc    3420
actttccggt ttttgacgga cacaaaatac agtcgaaggg actaatactc aataacttgg    3480
ttctgtatgg tagctcataa gggttgtggt ttatgatttt acagggtgtc tgcctactct    3540
cgcaacccta ccagtatgga ttggattgta tcgtgctcta tcaaatgttg ctaatgaggt    3600
attgcatcat gaactggagt gcttgaaaca gttgtccttg tgcggcatgt tgttccacct    3660
```

-continued

```
tagtttattg tgaaacatag gcgtcattag acaatccaca tttagagtaa tacaggaagg   3720
tcttaccata tattcatttc aaagaggttc aacagacatc gtaatgcaaa gttctgtaca   3780
ttttctcttg acttcaacgg gagaatatct attcttaaat gagatatttt ctgtggtact   3840
ggtattcaag tatgaatgta tgtaactatg atttacttat gcagttctgg cttttgcaggg  3900 gctcttgact gaggggttct tctggattcc atccttggca ggccctacaa cgattgctgc   3960
tcgttccagt gggagtggca tttcgtggct atttcccttt gtggttagtt agtcccttca   4020
gatgcttgtc ttcgttattt ttttttccata tcaaatgtaa tgatgctggt catacagtaa   4080
catatagtga atttgttgat caaaatggtt gtccatggaa gctt                    4124
```

<210> SEQ ID NO 15
<211> LENGTH: 3053
<212> TYPE: DNA
<213> ORGANISM: Physcomitrella patens

<400> SEQUENCE: 15

```
ttgttgaatc atgttaattg ccaatggtta ttaatgacca tcatattgta cctggaatgc     60
attggaaaag taatgttcca ctaaataaaa gttgatccac caaatattgt tgtctagtca    120
tatcgacaaa tagattcaaa ataaattaaa attaaaattg aaaatgtata aacattggca    180
tgaaaatgat attaatttaa aacaattcaa aacttataca attatttaaa atacattagt    240
caccgggtta aaggagacag actgacagaa ttggattgcg gcaatcagta gcactgcaca    300
aataaattta acatgaaaac attatgattg ctaatactct gtttgcatgc acttctacaa    360
caacaaaaac aaaaaataca atcaaacaaa acaagcaaac aataaatgat tttagatttt    420
gcatgataca agcaccagag ataattatga ccatgtgata aatacaattt ggaccattta    480
tatcctacaa aaaaagaaa aagaaaaaa gaaaagtttt tgtttgtatt tgatatcttt      540
attttgttac caaaattaga taattgcaag ccttgtattg tctgagatgg aatgtatatg    600
taacacattt gagcaaaaaa ttaaattaaa ttaaattaaa taagattttt ttatatatag    660
taaattgtaa aattgaccca acatttact aaatcaaccc acccattcta accatcataa     720
gaagaattcc gctatcaaat ccaggttggt tgaaaaccaa tgaaaaaatg gttggcttct    780
caaccaatga taatggatgg gttaatttaa taaattcatg ggtcaattta aaaattccat    840
atatataatt aaaaatcaat tgcaaaaaat attttgacac aatcacacgt gttttgaaaa    900
tcatacatgg acaaaaatac aaagagattt tttaaccaat attttggaaa cacatttagc    960
aaggtgtcca atgcccttcg atacccacaa gaacacacct tactttgccc atatttaccg   1020
atatatgctg cagtcagtta gggttgaatc cctgagggag gggggctccc gtgtgaacaa   1080
agtccaatgt ggggccgccc aggattaggg caccaggtgt gaacgaggct ccacccgagc   1140
gagagccagg aatttgaaac tggcatggga aaggggggttg gttccacctg atggcacctg  1200
cccaccacca ctagtaaaga ttcaatgccc accacactgg ttttttgaata taggatcttc   1260 cttctccttc taattcttct cttgatggat gaataatata accgatgaat gagtgggcac    1320
atggacgggc ctcgcccct ctctactctc tgcaatacat tacaaaatac atacatgtat     1380
acatagggat ttgatgactt caatacatac acactacaaa accgggtcag gagggggta    1440 taaccaggca agcccgagtg gcgggcagta acaaatacac accccaaat cgtatgggcc     1500 ggacacgtct gagcgacacg cgggtgccct gccctcctgc cccttccctc gccccttttc   1560
tctcgaccgc ctgtcgccgg cccggcccag actcctgcca acctgggaac caaccccct    1620 ttttggtgag tgctcttcac ttccctcgca ctcgctgctc aagttgaggg agggagggag   1680
```

-continued

```
taggagtagt cactcacccg gcctggcccg gtccggttcc ggtccgcggg ggctgcgttg    1740
cgcgacccgt tctcgtgggg ttatctctgg ttctctatcg ctcgctcttg tgcatcgtac    1800
tgctcctact ttttcccatt gttgctatgc tcgctgccct gcgctgcttg gccgtccgtt    1860
gtgcccctcg ctcgtcaacc aagcactgca gttcgctccc gcattccttt ctgcagcacg    1920
gtgtatctct ctctctctct ctctctctcc tcatctgttt agcgctggtg ccggttctct    1980
taaggtgaga gcttctgttc tatcggtgtt ctcggttttg gtatgtgtgg tgaccgacga    2040
tcggtttgtt gtgcacggtc gctggatgta tggtcgtctt tgttcttgtt tagttctgtg    2100
tggcgattaa cgtgttcttg gaggagtatt tttggccttt gtctgctgat gcgctcagca    2160
gcgttgcgtt agtgtaggct tgtgcttcac atgagcgtgc cgcgcgtcta ggcgtggtgt    2220
ttgagttgaa tcttttgccg aatgactata gttattgatt tcttgttatc tgaagatctt    2280
gtgctgagat atgtggtgta gggattcgag aagtgctatc cccttgttgt gatgaacagt    2340
tttcatttga tgtggttatc atactttgga gccttgcatt ccggatcgtc attagcttca    2400
tctacgtggc tggattttc cgtcaaccgt aggctgaagt gccttaaggg gttacatgtg    2460
ctgagttgac tacatgtaac aatggcatgc aaactgattg cgtgcacttc atacttgtat    2520
tcagttcgtt gtagagtccg ggatatatgt taggtagaat aaagaatctt atctctcggc    2580
attcgaataa aaatttcatc cttttgaat gcaccttgtt tgaaaggtcg ccccatgccc    2640
acggttgact gagaacaatg tctgcgcatc agttactgat ggtcgcacct gttgtcacta    2700
atttgagtga ttaaggtttc ctaccggctt tttcttttcc actgatttag tttattcttc    2760
atcaagttta caaatattgc tctgtatatc acggttttg ttagtctttg atgtaatcat    2820
attacctggg tttattatct agtgaactat gactgatatg ctggcgcata ttctcctact    2880
taatttgacc ttattagaag atgttcgtac ttagagtacc ttttacttaa tgtaactgaa    2940
tctatcattg ctttcgttct taatcgtgct acaaaattta actcattctc tcgttaacta    3000 atgttttga gcacttgcac tgttttgaa ctcctgtagg atcattctaa aaa            3053
```

<210> SEQ ID NO 16
<211> LENGTH: 1879
<212> TYPE: DNA
<213> ORGANISM: Physcomitrella patens

<400> SEQUENCE: 16

```
atctgtactg cacagtttta cattttcag gcttgcattt tgctgggatt gagttcttgt      60
tttgatagaa ctctggacgc aaatgtcttt gactgcttag ttgggctggc gagcacacag    120
taagaagtgg tacatgttgc cgaaactatg gatttgtaaa aatgaaacgt atctgggcgc    180
ataacgaact gcttatatat gtcgctgtct gttaacttca atctctacat gtccagatcg    240
atgcggtaga acccgaccat ttttgatcg atgtttgaac cttttatgt taaataaaag      300 gtaccatgtt ttcagcgcat taatcatatt tattttggtc actatggact tgatgtacac    360
cggatgttac agctcagttc tacttcacag ttattcactg acttgccctg aaaaagtcgg    420
agtgcagatc tcgttgtgtt ttggtaatct ggttggccag tctcagagct ctattttttg    480
atgaatccag ttgattggca ctcaatgttt ttttattt tttactttta tcatagtgtc      540
aaggttgcta cgccaggaat gctgtgaggc acattctacc cgtatgaatt tcctcgttcg    600
caatagctgc aagctcaatt taggttttc tgagcaagtt gtagaactat cgtgtactct     660
caccagattt cagcctctca gtgctgagtg ctttcgtcac gttaactaat tgtggaagat    720
```

-continued

```
ttggaatcat ggttgcatcc cttagtttga cagaattcac agtcgttagt tgacctctct      780
atcttggtcc accatatgtc aacctgttca agagggctgt gctcggttag gtaatcactc      840
agaagtttct tcctacagaa aacttgtttt gtgggcatca tctacgtgga agaattgttt      900
gagcattaaa tcattcaaca ccttcagtta catgaagtag gttggaagca gtgccttgaa      960
gagatcctc acagaaagcc tctcaattct catgaagtct gcatctaact tcttttgaag     1020
tttgtacacg tgtgggcaga attgaagttg gttttgtgtt gtttgaaaca actgtaattt     1080
aataaatccc aaacaagact aaggccatct aacgttttca catgttttaa aaaattacat     1140
tgaactttgg gctaccgtag ttttagacag atgcaattaa aaataaaaag aaaaaaatga     1200
aaagaaaaaa gtcttgtttg ttttagttgt ctgttttgta cagttttgtg acctatttta     1260
gagtgtcatg tatcgaacat ttgactcaca attataaggt tttatatttt aaatgagtct     1320
tgttgtcttt tattttattt tgttctacat tctgtaatat taaaacttct attgaaaaca     1380
caacaaacat ttaatttcaa gttttcaaa tttatatg catattttgt atgtaaattg        1440
tacaaatgtt cataatgcaa attgaaatat ttaatgtaag attatagcac ttaaacctga     1500
tccaaaagat aataattttg ggcaaataat taaaattatg atagacaaag tttagaatgt     1560
tgtaataaaa atttatggta agtgctaaag tatgtaaaac aaatttcata aagaattgct     1620
tgtagcattt tcaagagaaa aaaataaata cttacgacta ttttttaaaat gacacaaata     1680
gtaaataaca atatattgat gaggatatat atataatc aaaattaacc attagtgatt        1740
tttaacctgc atagtattaa tgtatgggac cgcaaggtag acacctacct ctactggata     1800
gcacctctca tatacacaat aaaacttta ccttgctaaa agtccaaggg aatttacaaa       1860
agaaattctt ttaaaaact                                                   1879
```

<210> SEQ ID NO 17
<211> LENGTH: 1823
<212> TYPE: DNA
<213> ORGANISM: Funaria hygrometrica

<400> SEQUENCE: 17

```
ctttcgtgtt gcctcaagag tgcctcgcga agaaagaagg ttccagcaac aactagagaa       60
tgggtacagc attcataaaa ctacagataa ttatccttca aataagtaag aaaaaagaag      120
gaaggaattg ataaataagc aagaaattaa gcaaagcagc cactcggcta gacaaaagag      180
actgcacacg ggtggccaag gaaagcgccg gtcatagggg atatgcggtc atggggtcac      240
tgtttccggc agccggaatc gattgcaccc tcgcagtggc tgacgagtca gaaccgggtg      300
ccaagtggac ccagctcagt cgcgggcagg ccgaggtggc accgaagcct ggtcaacgtg      360
gaatggatac gaatgtactg gatacgagat acgaatacga tacagtagag aaagaacgcg      420
gcgagggtgg cacgaattcg cagacacaac cgagtcggcc tgacaaggcg ccccgcctgt      480
tctgccgccc cttccatcac ccgctttgtc tcattcatcc acggctcctt tttagtgtct      540
ctgcgcgggt cccacccct ctcactggac tcgagatgcc gccctgcgct gcctgactcc       600
acctggcccg gccgacccg ccccgaccg ttccatggca gatgttgatc gccccgtctc        660
gcagctcctt ttgtgcaccg cgtggcttcg tacttggcca ttgttgctgt tgctgttgcc     720
ggtgctctgc tctgtcttcg cgaggcactc ttgaggcgat tttttttgta gtagcgcaag     780
ctcgttgtgg agccgcgccc agtaaatcat ctaggcttag tctgtatcca ctaccctccg     840
ctgcgatcac ccctgcttcg ttgtcggcgt ctatttctca ggttcgagtg tttctgagtg     900
ttggcgagga ttgagtgtag gagcgggagg ggtttgctgt tgttttgtc gctggcggat       960
```

```
gtcgatcttt cgacgcgatc gcattttct  tttgattgtt ctgttttgga gaacggaatc    1020
ttttgattgg atatatagat tgtgtgtttt gcatgcgttt agaacgttta cacgggcgat    1080
gcatgagtcc tggtgtcgtt tggaggccac ggatttagta gtttcttgtg caaggtggct    1140
tagatcttgt actacgagat gtttctccat gattgtggtg gcgatgactt tgtatacttg    1200
acgtgtagtt aatggtgat  gattcaatta tcagtggtgc atgattttgt tacgatcgg     1260 atgatcctgg atccctgatg attctttttc aagtaggttt aattctctgc aagcgcgaac    1320
ggttggtcgt ctcattctaa tggtggcatg atcgcttatt aaattacgtc gactgaattt    1380
tctccgtctc ctgaattgtt ggagtagcgc ctggaaattt gttagatgga gattttcca     1440 ttatccggga aattattcta ttaattcttt tagactcact cgctcataac gcatattgaa    1500
ataaaccaca gatgattgct tgatcactta ttcatttgaa tttgacagaa tacttcccct    1560
tcctgtttcg gtgaattaaa ttatttcgat atttagaatt taatttaata ttattttttac   1620 acagtacaac gaatgcaaag tggaggagtt gtcaggacaa ctgaatccct cagttttct     1680 agtctatatt tctgaagact tccacacaat atagtagacg ttctgtgcta tcctgactgc    1740
aagacaaaat ttacgacgca agtaacatc  tcctttttta atctgagatc tcttcaaatg    1800
gttgggcagg tccgtattaa gaa                                            1823

<210> SEQ ID NO 18
<211> LENGTH: 419
<212> TYPE: DNA
<213> ORGANISM: Funaria hygrometrica

<400> SEQUENCE: 18
aggagtgtta cacatctttt acttttttca gcacgcctct tcgctcggct tattgaactt     60
cgattacaaa cttgtgtggg taccgaacta ggccggctag cgtagatcga gtagaggtcc    120
ttgttgcagg aagttttcgt ttgtaaaaat agctgatatc tggacacata cgagtggctg    180
attggattca gtgacattca cattatttgt taacaggtcc agggttgttc gtagagtctg    240
gccccatttc tcgtcggaat gttggcgccg ttttgtgtga atgatggtg  attatggtta    300 aaatgcatgc gtagtcctgt tgactatggc tgaatggata agatatattt ccatcatagg    360
ttagatttca gcggagcgt  gaactgtgac gctcaatcac agaatgcgtc gtcttagcc     419

<210> SEQ ID NO 19
<211> LENGTH: 1333
<212> TYPE: DNA
<213> ORGANISM: Funaria hygrometrica

<400> SEQUENCE: 19
ggatccgaga ggaaagagag agaagaggga gcgactcatc tagccaggcc cggtccggtc     60
ctctgccctg cctggcgcga cccgttctcg tgcctatctg tggttctcta tcgctcttgt    120
gcctcgccct gcacctcctt tcccattgt  tgctgctttc tgccctgtgc tgcttggccg    180
ttcgttgtgc ccctcacctg tacactctcg cagccaagca ctgcagtggc agttcgcctc    240
cgcattcctt tcgtggccgc gtatccccc  cgtcatcttt tcgtcggtg  acagttcttt    300 gaaggttaga gcctctgtcc tgctgccgtt ctcgctgtgc ttgtgttgtg gccgacgatc    360
gggtttgttg tgcaaggtcg ctgtgcgcat cgtccttgttt agtattgtat gtcgattact    420
gtgttgtagg agcagtggct aagcttgtc  cgctgatgtg gcacccaacg gcgtcgctca    480
agtgtaggct ttttctttac acgagcttgg tccgcgttta tggtgtttgg atgttacttt    540
```

-continued

```
tttcccgaat gacgatatgt tgtgatttct ttacaacaag agattttgtg acgtgaactg    600
tagtttgtgg attcgaaaag tgttgttttcc tcgttttttga tggacattac ttatgccttt    660
```

```
tttcccgaat gacgatatgt tgtgatttct ttacaacaag agattttgtg acgtgaactg    600
tagtttgtgg attcgaaaag tgttgttcc tcgttttga tggacattac ttatgccttt      660
tagttgtcac ggttggtggc tttgcattct tggtcgtcat tagtttcatc cgatgctgga    720
cattcgctac catcccaagc tgaagtgctg aagttgattt catatgttca gtttgctgtg    780
tgcaccagta tgagtcaaaa ctgattggat gtccttcaca acttcattct cttcatctta    840
aagtcgagta caaatcaata ggtacaggac tcctatattt tggtgttccg ccatagttat    900
cgtctttcgt caaaattacc ttattgagag gacttttcct tgcaaaggtc tcatcgagac    960
caatctctca gagtcagata cctatggtcg cagcagaaat ctctagtcaa tgtttctaag   1020
ctctcctaag gattttcgct ctttcatcag atgtattcta ccaactcca agttcgcaac    1080
aatttcttca tacatcattg tcttctggtc tttctgttct gatactgcac cgattcattt    1140
taggatctta taatccgtgc ttgatgtgcg gatatgtgaa ttccctgagt gttcacctca   1200
acgtactcaa agttgttcta ctttcagcat ctttcagcca atgcggcaga tgcgatcact   1260
tccgaggact ttaaaattct gtactgtttc tttaaaacgc ctttttcgat tctatgcagg   1320
atcattgtaa gcg                                                     1333

<210> SEQ ID NO 20
<211> LENGTH: 3289
<212> TYPE: DNA
<213> ORGANISM: Funaria hygrometrica

<400> SEQUENCE: 20
atgcatggca aaacatcccc tgtcttccat gatgagaaag gcgaacctgg actgcttgat    60
ggtcttccca ggtatctcat tgtgcttcgg tagttgttga cgtcttcact tctgcttctt   120
tcgcttcctc ttcttcttct tcttcttctt ctttctctct ctctctctct ctctcccaaa   180
ccttccttct gtcttcccttc ctcttatttt cctatgtcaa tgaagtttag cacctcctaa   240
aatttttgga tgctgttttt taaatagaag ggacgggatc aaaggacgag tgagtgtcgg   300
cttttgcatt gcttccgttt tataacaacc tattaaggac gtagatcgtg tctgtaaagt   360
catctcttat agccttttat agtctttta agagagaaga gccacctctg agtttcttat   420
agattcggac aagagatgtg acgacttagg aagtgtcttt cggaattttt cttgtgataa   480
tggcgttgca tttcttgtcc tgtcttattt ttaactgaac agtatgtacc atttttccgt   540
atagtcctta ctttataata tgtcctcttt tctttcgcct cacgttcatc atattctttg   600
atatgtacta ttaactttcg ctatctgttt tcttgtagtc ctttcaccgc gtgccgctat   660
cacagcttgg tcatagagga ggcctcattt ccagctgacc aactcgagat tacagcatgg   720
actgaggacg ggcttgtgat gggggttcgt cacaaagtct acaagcacat ccaaggagtg   780
caatttcatc ctgagagcat ccggactcaa aatgggatgc agatcgttgg aaattttctc   840
aagatttag atagaaaaga gcggctgac aaggaaggag ctgaaatgaa attttggag     900
agtgtttgag tgatgagttg tactggtata tcttttcttg tgcaagattg ccagcatttg    960
tcagcttgct tttgttagag tcctgacccc cagcgtataa ctccttgagt atatgcccaa   1020
gcaggcctag atgctgctgc aataaccttc tcggtgagac agggtagttt tgaggtatt    1080
tttgcacttc cagatggagc tactactaca aatatctatc cttatcttac gttaaactac   1140
gatggaattg ccatgatcac tcaggtacgt ttaagttgtg attggacttt tagtgattac   1200
tttcagagcg agctatcaaa ctggtgcttg gaggagcaac gcaaggaatg ctgaattttt   1260
ctaatgatct aattcagctt aagttttttcg tcaaacttag tgatattttg aagttcatct   1320
```

```
cgttagtgaa acatctcaaa gaagtacgcc attaaattat tgcagggctt gtgatgacat    1380
tatttgatag tttacctctt aaactgagaa cgcattgctc tcctttgtat agttccagtc    1440
atttgaaagc tctatttgct ctctgtaact taagccttgt tcaaggcatt taaattccct    1500
cttccacgat aaaaatggta gttatgttgc tggttggaac tttcaagata ccataacatt    1560
gtggttctca ttcacaacgc aggaagtttg ttgacctata tttttgaaag tggcgagtga    1620
aattgtttac tcatcacttt atgtgtgttt ctagtatgtc acttcaattc cttcctcaac    1680
tgtgcctaat ttttcatctc tgtgtgtcac gagcgtaatt tggcttagac gttggaacat    1740
tctaaggttc cagtaaccag ttttcattta ttattttaa attcacagcg cctcaagtaa    1800
tgaaaggaca aacgccgatc attgcgcaac tctaattgtg acggtcttca agacaactaa    1860
cggcaggtca ctctcttgtg atgttctcgt tgttgtcaaa cctgtataat ggcaattcat    1920
ttcgacatca cggcaaactc atgatggttt taacgtgat ttgctcacca cctttcattc    1980
aaagttatca ccgacaccct atgggtttaa ccatgttatc tgaaagcttt ctctacgtat    2040
gtatgaatct gctcattagg gtgaatttgg aacttaaaga atctcacacg atgtccatga    2100
attttgttac tggacaacat atactgttga ccacatagat atgcatgttt agaactgcaa    2160
aaaagtttgt tcacgaagac agaacgacta gaacgcagaa tacctgcgat cggtggaatg    2220
ggatcatttg cagtaaagct agtaaaggat cgaaatagac gcagagtaaa cccgatgcgt    2280
tagagggaa tgggagatcc acaggactcg gagagaaaat gcaaccctgc gggtaaaaat    2340
agagaacgcg aggaggaagg gtagccgaaa gagtttcacc gggatctaca gtataagccg    2400
caaagggagc cacgggtact agtgccagct ttgcagcaga gagcgaacgc gagggagcga    2460
acagatccgg gccccaaatc cccttcttct atctctcaag ccgtccacag ccttcattct    2520
ccatcctcgc actattctcc tcacagcagt tgcatttgtg gttctctcca tcttcaaccc    2580
ttcgactttg gtgcaagccc gcttgttatc tatcccaagg tttcacgcac tccccccttc    2640
gctgtgtgtt tcgttgcaat attttttggct ttagttttta ggtttataca tagtgcacat    2700
gctctcgcaa aaccgtgccg cttcagggga tcgtggttct gtagacttga gcacagagat    2760
gcgggtgaac tcttagtggt cgccgctgca tccccagagt agttatgcta cctaaagaag    2820
cgtgctcgta cggtcgatat gtttagagat ggatatttag acgatggtgc gtgtcctgcg    2880
gtcatcagag taggtgaagg gattttcgt aagatctgct tttgtgacgg atctgcaatg    2940
caggaggtct gcgtctttct ttttcttcag cttcgtgccc aatgcgtcaa atgcgcaccc    3000
attgcacaga gtgctattaa ggcggcttca tgaagctccc agttttgtga atcatgttaa    3060
cttgtccact gatcagaacg ttcgggctgg catacgtgaa gcgaatacac attttctac    3120
agcatgttcc ttattttagt cttcatactc actgcttcga ttgccggagg gcctccatgt    3180
tcgaccacat cttcacacgg ggcttatcat ctgacctaaa tcgcacgtgg cctctgtatt    3240
gtgtcaatgc cagtaacagt cttttgatg cgcagaacat ttcatctcc                 3289
```

<210> SEQ ID NO 21
<211> LENGTH: 937
<212> TYPE: DNA
<213> ORGANISM: Marchantia polymorpha

<400> SEQUENCE: 21

```
catatgcgta cggagttgtg gtccccgatc gccgtagttg ctgttggtgt ctggtcacag      60
aggattcttt gcttcgcttc ctaatgtagg tggccagggg tggatcgtct tcctcctacg     120
```

-continued

```
cttcgtttgg acacatacat ctggatcttg agaggaacac gtgaattaga gttacatgcg      180
gtattgcgtc atctttgcga ggtaacggcc gcgccgcaga cctagcggtt gcttctgcgc      240
gactcaagga atcttccctc tcctgctcca tcactggaat gagagttgca gtctgatctt      300
tgggaaatct ttcatcttgt tgaccatcga ctctgtcctc tcgatgaggt ctgggatgat      360
tctgcatgtg atactagcgc agtcttcatg attgtcacat gcatccagat gcgcatctg       420 gcgcgctttg tgcttggtca tagccgcctt cttttatctt gatttgccta atgagcccca      480
tttccagacg tggacggcag atcggtcata aggtccaaga gcaggaaatg ctatgaggcc      540
gtttgcgtgg tctacctctg ctggcctgcg aaaagactgc ctgtccgact caatatctt      600 taaacattag gctcttcagt tgtctcgctc agaccattat tatgagttat tgttaccgta      660
gtgtgttgct atgtcagccc gtgtagtctc gtcaatttct ggagggtaat gcgaacttgt      720
tcatgacggc acgtatctcg tcgccccgaa gatcacccct tgtgagaagg atttcatgcg      780
tctgcgtcct cgttcatgtt gacatgaatg atagaagccg ttctgaagac acgaaatgtg      840
gttgacatat acattgtgat gctcatgtct tttgtcgagt caccaagatc cgcaaccatc      900
tcatcttctt tcattttggt taggtaactt cgcgaaa                               937
```

<210> SEQ ID NO 22
<211> LENGTH: 3025
<212> TYPE: DNA
<213> ORGANISM: Marchantia polymorpha

<400> SEQUENCE: 22

```
tcatgatgtt aagcgttttc ataatccaaa gaggttttgt atatagataa aatttacttt      60
ctgaatatgc aagcatcata ttctaaattt aatcgaacat aattttttct gagctttctc      120 tttcttttc tttaaattaa atttccttca ctgcaatttt tttattacga ctcccacgag       180
gagtattttc cgactataga tcttagggta taactatata tcacgctc gttctaaaca        240 ttttttctaa ttttatgaaa agagataaat atattaataa tataggttat ttagattatt      300
gaaattcaca gaaaatacca ttttttgtctc attcgtatg ttctagatgt gtgtgcgtat      360
atggtcatat acttgggata ttttaaattt gtgaatacaa gattataaca aagttatcat      420
tgcaaaatac taaagataag ttatcttttgg tgagaagaca tgatataccca tctgcatatt    480 acttattcac caattgacca aagatttaca atctaccttg atgaaccata aatttgagaa      540
ttttatatgc agatatttgc ggatcttttcc aatcattatc tagctcttgt ttacattttt     600
gctttcacaa aaatgcaata atgtgaaagt tgatgcaata atccctttag gtttttttgac    660 tcataacaat tttctctcca aagcattgag attcaatgtg gacgtgatac ataaattcac      720
atcttgatta gttacatata aatgtggaac tgccgtattt gtcggaaagt tcatacaatt      780 tttttttgttc atttgaagat cataagatag ctgcatatat caccattagt gatgatatga    840
tatatgacat gagaaaaata taacttaata tgaaggaagt cttgatatgc cttgctatcc      900
ctaggttggg gtaggtcttt ctttcatttg cgattattat tactgtgagg aatattcggt      960
agaatggatt ccttggaagt gttgtatttt tgacctctca taattaagca cagattaatc     1020
ccttcatttg tggtctatca atcaagtggt ctacgaatga ctctaattttt aagattatttt   1080 ttgtagttgt gtggtgtttt agtagttacc aatcttatac ttgaaagaaa atgaaagcaa     1140
tgattactca tactactcaa tgccaagatc ggaggctaaa tccaatgtat acaagtatag     1200
aaatttgtaa agagttaagc tctttctttg ttcatgtagc tttgaggctt tgtaaaaata     1260
tggacattga ttcggatata gaggtgagtt gtgcacaaga gatgaccata cttggtgtca     1320
```

```
aggtgtagca ttttttttcag attatttata agaaaataat caggaaagga aaataagtag    1380
tattcatcct agatataaca tttgtcgaga atctacgag ataaacattt tttcagacga      1440
gaacaattct tcaaattttc agatgcaagg gtacgcattt agcattgcgc tgatattaga    1500
gctagtctcc tattgcatgt ttgatttcat acatgtacca cccattcttg ttactgcagt    1560
gtgtgaaact tgttgaataa gaagttccgc aattatttca aattattgag agtcttctta    1620
cataattttt acttatccaa aattcttaag aaccccacaa taaattcagt gatacgcttt    1680
gaatggctca ccagttactg gactgccaca attcgcagca ttggagactt ggccaactca    1740
accagagaag ggaccacgtc gaacgatcta cctccctccc agtgagtgag tgagtcttcg    1800
ggtgcagtat tgtccaagtc ctggaatgtc gatccagccg caggaccagg aagatcgggc    1860
cgggtacagt aaagttgcca taacaatccg gcaacgaacc acagatccgg gacgatctag    1920 cggaagttg aagtccaagg ctcggggcac atctccctgg tagaattaga atccatagcc     1980
agaattctat ctcgaaacct tgtttcgcca gcgttatgat tataatcaag cgtccccgtt    2040
aatctgattc ctgtgaaagt tagttagtaa cttcatacccc cagcattatg attataatca   2100
agtgtctcag ttagtctgat tcctgtgaat gttagttagt aagttcaggc cttctcgtaa    2160
tagcttcttg cgtataatct gaactgttga taatggttaa actcttgaat tacgacatat    2220
cagtcccggg agattaatct gcttccgcta agctcgagga tgcacagcag taattttggg    2280
tcgtttggga tttgataaaa cggacgggaa tatgcgtcgc gagttccgag taggagtgag    2340
gaggaatgca aaccagcgga ccacgtaaag aggcccacga cagtccagca gcccagctgt    2400
gagacacaag ggggacgaaa gggaccgccc aggccgacca cctgatgtca gggggagctg    2460
gtgcgagcgg cgacggacat ggatcggcgt ttggttgcgg tccagaagcg ggcgaggagg    2520
gatccgcatg agtgacacag tgggggcaga attgggagaa gatcgtgggg gtaattgaga    2580
ggggagattc gggttggggc cgagacaggt aaggaacacc gatgatgctg aggaaaaatat  2640 gaggaattcg tgagaatgcg acagggcgag agcactgtgg ggcagaatgg aaggggggcc    2700
agcgatattc gagcaataaa ataagagcgg gggacattcg aaaagaggcc ccatataaag    2760
ccgatcttcc attctgtttt cacagagctc ttcgtcgaac agagcctctc aaactcgctt    2820
tgtgctccca gtgcttctgt ctcggatctg ctctgctcgg cttcgcgctt gttgttcttg    2880
tgaccatcac cgccttcagg acgctcacgc ccaacgcaag aatttcgagt cgaagtaagc    2940
gagcagctca atcgcttcgt taacgcgttt gcggagatct tcgaggtttc gcgttcgaag    3000
ttcttcggac acctccttcg ttaac                                          3025
```

<210> SEQ ID NO 23
<211> LENGTH: 909
<212> TYPE: DNA
<213> ORGANISM: Marchantia polymorpha

<400> SEQUENCE: 23

```
aagcttagca agcagctctc gcagcggatc tgcttcttctg ctgctccctc tgcttcctcg    60
tgctacacgg tcttcgtcct cgcttcctcc acgcttcctc gcgctctctc caggtactcg    120
tcgcctcgcg ctctttcttc ttcctagttc gtccgttcct cgtaccggga tagggcggtc    180
gcgggtctcg tgagggtttt ttcgagcaag gtgcgtgagc aagttcatat cggtgggcaa    240
tgcatggggc gaacctggtc gggcccttt ccgaggccgc cggagagcct agtctccaag    300
ctgtagtatc ggtgttctcg aagatcggtc ggtgtctgca tctctccatc tcgattcgtt    360
```

-continued

```
tcgtctgagc tgatccgccg gtcgattttg acgatgtcgt gtcctcacct acgcaagttt      420
ggttccgagg attagttttg aagatgctgt caatgggaag tttagctctt ggttcgtgat      480
tagtttggac acggtcacat gaatcgtagg gacccaggtg tcgggcggaa tcttcagcag      540
tcatttcggt ttccgtaacg ctggatttaa gctgaaaacg ttcatcgatg gattgcggat      600
accatgacct aatggatcgt ccagcttatt cttctggaag tatagacgtg tgatggctgt      660
ggcctgtggt agggttggac acgcccgcag tggtctctcc gaatttgaat gtcgcaatgg      720
tcgatgtgct ctgccgattt ggggaatcga agtggcaaac cggtcgttcg gactgtcgag      780
tgtatgcctg ctgcttgtgc gatgtagtgt ggattttcc tccgatgttt tccaaacgtg       840
gtcgggattg cagttcttca atctaccagc ggagctaatt tcgtctttgg cttgcagtct      900
atcgtcgat                                                              909
```

<210> SEQ ID NO 24
<211> LENGTH: 2146
<212> TYPE: DNA
<213> ORGANISM: Physcomitrella patens

<400> SEQUENCE: 24

```
atacaagagt tataaatcat atacaatgat tactttcata taattgttga atattattgt       60
tacaacctaa gtaacaataa cattcaatta aacattcatt gtggttttca agcatattaa     120
tcattctttc ttctctaccc tatagtgatg ggaaattatc ccaaactcaa tgtcatactc      180
caggcaattc agaaatatag tgagatgaat accaggaata tttattcaca tcgaccccta     240
tcgccgggca atgccactcc caccgcggaa tgagaaactc cttgaaaaaa caagtccctt      300
cccagctgcc cgaaatcggc cgcctggtca gcacggcacg acactgccca cgtgcaatcc     360
tgacgtggcc tctacgtccg gaaggcggcg ccgttagcga tgtcctccta tgcaagttcc      420
tcttgtggcg gggcagtgtg cccgccaact tcaccgtcac cctccacccc aacaagtggc      480
ccaaattact caggggcagc ccagcttcga aattttaagc ggtgaccgcc ccttctcatc      540
gtcacgcgtt acttctttt cactcaatcg agtctgttta ttattggccg ctaggaaatt      600
gcagcttcca actccgcatc accgcgtgca gtacagtgga gatcttcaag agtgtcctca      660
ccaggaattt gcaacttgct ccttgcaatt tgtaataaat ggacagagaa gcctagattc      720
cgcatccaca gtgatgggtc acgtatcaat aagcgaagct gcgttggcaa ctatggcaat      780
tggtttggtg tcttcgttcc tgtcaagttt gaaaagaaga gggagatctg atttcttaat      840
aagtgtcgac ttgtctgggt agtggattgc gtggggcgtg tcgtagtgcg acgcgatcgc      900
atcaaattca tcgcctcaaa atttgtcacg ttgttgggtc aattgcaacg aactgcgatt      960
gaaggattct tctcggtggc cttcaaattt gctttagtat gacagaagtt ttgcagctgt     1020
actcggcgtt tggaaggagt ggaagtgagg tggatcacca cgcaccggag ttggtgaatt     1080
gtttactgca gaaaaaaatg ctttgatca catcagaatg attgatgttt cagcttgaat      1140
ttcacctcaa gatgtgttct catcatgaaa ttttattgg gccaggatgt actttcattg     1200
ttttgaaaga atatttaag acgcttgtgt tttacaacct ttcggaagat gcgtccttga     1260
ttgaaagtgg ttaatgtttt gtacatcatt actggatatg aaaataccaa taaaatgaaa     1320
tacaataaaa tattttttg aaatgaaaat tggtttaaat aagcatgtaa ataatagacg     1380
gtggagtaaa gaaaaggtaa taaaaaaaaa agtatgaatt ctattactct tcaatataaa     1440
agtaagaggt gtccgtttgc aagcaataaa aattcagtaa ttgctagata aattcaaaag    1500
ccaaccaata cacaccattg ttttgctgca aagctagggt ttctaaggcc acaattcaat     1560
```

-continued

```
gactagtgac ttacatatta cttccaaacc gaagcaaagc aagggtactc cacgattgta    1620
tatatactca cttgtttatt tttaaaccat ctgaaatcac acaaaaatgt tgtgaccctg    1680
cttcattatg ataattaagt gacgttttaa tctcattaaa tttaatgcca ccgtaggtta    1740
tggacggaaa tggatggatg taaatggaaa gatcggcggc aaaaagacca aattccatac    1800
tactgcccga gtccgataaa gacggaaaca atgcgataaa agtaaaagtg agcagaagaa    1860
agtgcacggt cgaaggcggc gtttgtttac atttacttca ccaaaaccga gcaggatatc    1920
gggcacacgg tcaggaagaa attgttcatg acggtcagaa cattctggat ggttggcgtg    1980
cttgctataa gaacactgct cctccgatct aaacctcgga ttgtgcgctt ctagatactg    2040
aatttgtttc gaccctgcct tgttgagtgg ccgtagaggc tcgacagtta ggatcagtgt    2100
gccgttgaat ttagtgattg tgtagcgacc agtacgtcct gtaagg                  2146
```

<210> SEQ ID NO 25
<211> LENGTH: 524
<212> TYPE: DNA
<213> ORGANISM: Funaria hygrometrica

<400> SEQUENCE: 25

```
gaattcattt ccattaacga gaatatgaca gtgggaagag cttccacgtc atccaaactc      60
aaagtatccg acgtggtcaa tccaagtgcc agtgccacct cagctccttc accagtccat     120
ctcgcggata agggtgacag caaggcgcgg tattactgga taagagaagc ggccaaggcg     180
gcagccactg tggtccactt tgctgcgtca ctacctactg cgattgtaat gacgagcggc     240
agcgtcgtgt gacaggcttg aaccgaccgc tgcttcagcc gcaggcagac tagaaaagtt     300
tactcgctgt cccactcgtt ttctgggtgt gcatccgaag tttctggatg gttgcccgtc     360
gttcaataaa ttgtcgcgcg tcgagctagc ggacactttt gtcaccgttc ttctctgttt     420
attctggacc agaggtgctg ttagcttttgt tgtgtgtgag tccttgggga aatccctgcg     480
cgtcacgaga gtttattgca gggaagtgat aaagcgttgt gaag                      524
```

<210> SEQ ID NO 26
<211> LENGTH: 2088
<212> TYPE: DNA
<213> ORGANISM: Physcomitrella patens

<400> SEQUENCE: 26

```
atgcatgtaa gataattcca attagaatct ataaatttct tattataatt ttttaaaaac      60
aaagtaccaa aatattatta ttttaatatc ctctaagtta aatccatata ttaagtagaa     120
acaattattc taataaataa tgataaaaat tagacatctt gcaataaaat ttcttttttaa    180 aaatagatac ataacatgaa aaatatccca taaatagcta acaccatcaa acatttgac     240 caaatatgca cttttagatg tgtcaagaca aaaagaaata tttgcaagat tttggagtat    300
ctaaactaat gtttgtcctc tttgcactat gagtaggatt tcttttatttt tgtttagtga    360 aaagatacat tgcaatttgt tttcataata aaaactatac taatgaaata gtgctaaaaa    420
ataacaagat taaaaaaaca taacccttct tacaaccttta atccttcta attagactac    480 ctcaaagttg tgccatttag cacaaaaacc attcttttaa atctacttaa ccctccaatt    540
tccaatgagc ttcatgtgca tacacaagca tgctttcttt ctttctttct tgaagaaaac    600
ttatctgaac aaacgttaat actctacttg ttgatgaaag tggaactttg accacataca    660
ggcttggtga tgtacttttgt atatctcctc acagttagtc tggtgcaatc caaccatgca    720
```

-continued

```
catagaatat gaatggggac atgcttccag ccactcgggt gtgcagaaaa cttgacaagc    780
gagattcaag caacggcgac tacgacgccg atcacgcaat acaaagcatt gttagtatgt    840
gataaaccag agaaagagat cgagtatgtg cacacaaaaa cacacagatc cacaggtatt    900
gtctacggcg ccaccaccat ccgtcaaagc taccatctcg tcgaggaaga atggtatttc    960
taaaactagc aatacaaccg ctgatggaaa caaccgaaag ctatgtcatt ggagagggcg   1020
cacgagttca tggaatacac agtgagaaga gataaagaaa taaataata taaaatacaa   1080 gtgtgcatca gcaagacatg gccgaaatct aacaactgtc tgcacatgct gtggtgggtt   1140
gtatccacgc gctggaggaa gtaactttcc tacatgcaca gaaaaacatt ttcagattag   1200
aaagctcttc tgttctagct aatctctagt accaagctca gacgtgtagc cgacgaagcc   1260
aatagcagct gggtatgcta gtcactgatt ctgaagcggc cggtgtgtcg attgcgatgt   1320
atctcagttc ggcgaaggcc tgtgtctgga acatgggaag agggtcttct tgcactcgtc   1380
aatctctcac agcaactggg cagggttgta tccgaacgtg gaaaacgcag caaccgttgt   1440
tgaaccaaag gatggtattt ttctccgaga aaaacgccgt ggcttatctg gtgtagacga   1500
tccctaatcc ggacatgacc gccgctgtgc aggtgttggg aaaccacaat gcgcaagaga   1560
tgcgagagat ggaggagtgc aagaagtacg actgcgaagc tacatgcttc atcgagcaat   1620
gaagtctggg ttttctccaa cttccgcatg cacacacttt tctcgacgac atccgtttca   1680
aggtacgcat cgggaaactg acgattctct gcactggtgt tcagactctc cggagaggcg   1740
gtgtcatgtt ctgagctctt tttcgataag gtgctgttga agtccagaat aatgggtct    1800 ggattatcct ctggacggct ccgcttctgg tcgaaaaaat ttcatcccaa aaaaggactt   1860
atctgttgac tgaaaatgtt taattgtggt gaggattgca tgcagcgacg tcgtaaagat   1920
agggtgacaa ggagcgttcc agagctcagc tcggggcatg ccccggcact ccctagcata   1980
taaacatacc gggtggaatt tgtacccacc aggtcttgct cggtgtcccc tgtgcccaag   2040
ctgttggctg cattgccctt gcgattcgag tgtggagaga ttttagca             2088
```

<210> SEQ ID NO 27
<211> LENGTH: 500
<212> TYPE: DNA
<213> ORGANISM: Physcomitrella patens

<400> SEQUENCE: 27

```
ggaacgaatt tgtcgagctc tctggttctg ggtcgggtag cagtagcttt gatggtgagg     60
cactgacagt cagtcgctca cacggcaaag tagcctggat gtgcttcgca acgaactctt    120
gaatttgagt atgtgagttc actttgaaca tcccagaagc aaaagaatgg gttttttcat    180
gtttgaattt tattttgtat agttgtgttg agccgcgatt tctatctgtc acttggcttg    240
atattctgag tttctccgat acgaatagcg aagtccactt gaacatctgt aacggcagca    300
attgcgtcag gtcaatcctc tcagattctt tcggtgcttt tgtcgtaaac tagcttgatt    360
gttgtccatt aagcttggtt gcttttcgtg agaaagcatg aaacttctat gacgaaaccc    420
ggttgattgt aatgtaacta gtttgattgt agtttgaatt tggtaattgc gttgtatgat    480
acataatgaa agtttcatga                                               500
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 28
atccaggaga tgttcaggcg                                              20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
ccgmacgctg tccatrgtyc c                                            21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
acattgatgc gctccarctg c                                            21

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
ggbatggacg agatggagtt cac                                          23

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
agcacatgca cacccaatac gcttgtcgca attc                              34

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
gtcgtcatag acgacaagac cggggatcca cagc                              34

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 34
tcagtgctgt ccgtgaatct ctctctctgc ttg                                    33

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
ctgtgttcgg attagactcc ccgtagcctt tgtg                                   34

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
tcgattggcg agttgcaagg agggcaagg                                         29

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
tgcctgctca tcttgagtat ggcgtgttg                                         29

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
ctgcaagcaa tgcgcactga aacaagatgg                                        30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
gacctggaaa cctgcacaat cacgcataga                                        30

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 40
tagcataaga taaagatgtt ctctacc                                         27

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
ctcaccagcc aatggctatg c                                               21

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
ccgtgggact tagttgtctt cacttc                                          26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
gatcgaaatt gctgcttggc ctccac                                          26

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
tcgaggatgt gtccttagtc gagaa                                           25

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
aacttcacgc attccacaag ccacac                                          26

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
```
ttgatactcg agaagtccaa aataatttaa tgatac        36

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
catcttcgct aaggatgatc tacaacgag        29

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
catcttcagt gtgctctacc tcacg        25

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
ctactcgagc acatataata ctgccctagt gcc        33

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
gacagatctc cttagtcgag aaggcgcggg acgtg        35

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
gacccgtggg acttagttgt cttcacttc        29

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52

```
gctgctcttc tcgtgattgt ct                                              22
```

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53

```
cattcccacc cttccttctc ttc                                             23
```

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54

```
gttttctggc tcttccttgg                                                 20
```

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55

```
atcgttctcg actcttcttc c                                               21
```

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56

```
gttacgctcg caatgcgtac t                                               21
```

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57

```
aactttctgc tgtcttgggt gcattg                                          26
```

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58

```
gacctgcagg cactcgagct tgtaatcatg gtcatag                              37
```

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59
catttcttaa taccgacctg cccaacca                                    28

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
catggagaag aaatacttgc acatcaaaag                                  30

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 61
cattatttaa tacggacctg cacaacaac                                   29

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 62
cattttttag aatgatccta caggagttc                                   29

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 63
agtctggcaa gttcccttcg                                             20

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 64
gaagagaagg aagggtggga atg                                         23

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 65
ggaagaagag tcgagaagcg at                                              22

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic Primer

<400> SEQUENCE: 66
catcttgtcc aactaccgcg acccgaaccc                                      30

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic Primer

<400> SEQUENCE: 67
aatctcgagt agcataagat aaagatgttc tctacc                               36

<210> SEQ ID NO 68
<211> LENGTH: 34
<212> TYPE: DNA
<213> ORGANISM: Artificial Sequence
<220> FEATURE:
<223> OTHER INFORMATION: Description of Artificial Sequence: Synthetic Primer

<400> SEQUENCE: 68
ggtaaagctc tcgagtgcag tagacgacaa aatg                                 34

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic Primer

<400> SEQUENCE: 69
catcttgctc aagctgtgcg aagctc                                          26

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic Primer

<400> SEQUENCE: 70
atctcgagga tccattcaac ggaggataag t                                    31

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 71
caactcgaga tcggtctgta agccctgtat ttg                                   33

<210> SEQ ID NO 72
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 72
atttctcgag ttgttgaatc atgttaattg ccaatggt                              38

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 73
ttactcgaga ctctactaat tgacaagtat g                                     31

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 74
gtcaagattg gaggttcctt gag                                              23

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 75
tccatctcga gtacctccgc tgtgtgtttc aaag                                  34

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 76
gtgcctcgag ccacatcccg accgcc                                           26

<210> SEQ ID NO 77

```
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 77
agcacctcga gtactgccct agtgccctaa tc                                    32

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 78
catccttaca ggacgtactg g                                                21

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 79
atgcatggca aaacatcccc tg                                               22

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 80
catggagatg aaatgttctg                                                  20

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 81
ttaactcgag atacaagagt tataaatcat atac                                  34

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 82
atatctcgag atgcatgtaa gataattcca attaga                                36

<210> SEQ ID NO 83
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 83
cattgctaaa atctctccac actcgaatc                                     29

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 84
atatctgcag tcatgaaact ttcattatgt atc                                33

<210> SEQ ID NO 85
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 85
atatgcggcc gcggaacgaa tttgtcgagc tctct                              35

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 86
ctttcgtgtt gcctcaagag tg                                            22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 87
catttcttaa tacggacctg cc                                            22

<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 88
atatctcgag gaattcattt ccattaacga gaatatgac                          39

<210> SEQ ID NO 89
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 89
catcttcaca acgctttatc acttc                                            25

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 90
catatgcgta cggagttgtg g                                                21

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 91
tttcgcgaag ttacctaacc                                                  20

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 92
tcatgatgtt aagcgttttc a                                                21

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 93
gttaacgaag gaggtgtccg                                                  20

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 94
aagcttagca agcagctctc gcag                                             24

<210> SEQ ID NO 95
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 95
atcgacgata gactgcaagc c                                                 21

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 96
aggagtgtta cacatctttt ac                                                22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 97
ggctaagacg acgcattctg tg                                                22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 98
ggatccgaga ggaaagagag ag                                                22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 99
cgcttacaat gatcctgcat ag                                                22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 100
tcdgtgaatc aatctcgtcc at                                                22

<210> SEQ ID NO 101
<211> LENGTH: 22
<212> TYPE: DNA
<213> ORGANISM: Artificial Sequence
<220> FEATURE:
```

-continued

```
<223> OTHER INFORMATION: Description of Artificial Sequence:  Synthetic
      Primer

<400> SEQUENCE: 101
cggtacctac aagggcctct cg                                                  22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 102
tgggacgtat cagggtacgt ct                                                  22

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 103
tatccggagg ttcccgcgac acc                                                 23
```